United States Patent
Fram et al.

(10) Patent No.: US 11,679,275 B1
(45) Date of Patent: Jun. 20, 2023

(54) RADIOACTIVE IMPLANT PLANNING SYSTEM AND PLACEMENT GUIDE SYSTEM

(71) Applicant: GT MEDICAL TECHNOLOGIES, INC., Tempe, AZ (US)

(72) Inventors: Evan K. Fram, Phoenix, AZ (US); David Brachman, Phoenix, AZ (US)

(73) Assignee: GT MEDICAL TECHNOLOGIES, INC., Tempe, AZ (US)

( * ) Notice: Subject to any disclaimer, the term of this patent is extended or adjusted under 35 U.S.C. 154(b) by 112 days.

(21) Appl. No.: 16/779,932

(22) Filed: Feb. 3, 2020

Related U.S. Application Data

(63) Continuation of application No. 15/791,962, filed on Oct. 24, 2017, now Pat. No. 10,583,310, which is a
(Continued)

(51) Int. Cl.
*G16H 50/20* (2018.01)
*A61N 5/10* (2006.01)

(52) U.S. Cl.
CPC ........... *A61N 5/1039* (2013.01); *A61N 5/103* (2013.01); *A61N 2005/1024* (2013.01); *A61N 2005/1059* (2013.01); *A61N 2005/1074* (2013.01)

(58) Field of Classification Search
CPC .................. A61N 5/1039; A61N 5/103; A61N 2005/1024; A61N 2005/1059;
(Continued)

(56) References Cited

U.S. PATENT DOCUMENTS

D244,393 S   5/1977  Collica et al.
4,509,506 A  4/1985  Windorski et al.
(Continued)

FOREIGN PATENT DOCUMENTS

BR   11 2013 027841 2   4/2012
CA       2835065        2/2018
(Continued)

OTHER PUBLICATIONS

Cole, P.D., et al., "A comparative long-term assessment of four soft tissue supplements". Anesthetic Surg J. 31 (6). 674-681, 2011.
(Continued)

*Primary Examiner* — Mark Holcomb
(74) *Attorney, Agent, or Firm* — Knobbe, Martens, Olson & Bear, LLP

(57) ABSTRACT

An implant planning system aids delivery of radiation to tumor sites of a patient. The system allows a user to test various combinations of virtual implants, each associated with a corresponding physical implant (e.g., a carrier with an embedded radioactive seed), and to view the dosage area of the virtual implants so that adjustments to the virtual implants may be made until a prescribed dose of radiation to a treatment area is achieved. A treatment plan developed based on the virtual implants may then be used in surgical implantation of the corresponding physical implants. For example, the implant configuration of the treatment plan may be projected onto a treatment surface of a patient, such as in a surgical room, so that physical implants may be placed according to the projected image of the virtual implants.

26 Claims, 41 Drawing Sheets

Related U.S. Application Data continuation of application No. 15/017,461, filed on Feb. 5, 2016, now Pat. No. 9,821,174.

(60) Provisional application No. 62/113,252, filed on Feb. 6, 2015, provisional application No. 62/205,172, filed on Aug. 14, 2015.

(58) Field of Classification Search
CPC .......... A61N 2005/1074; G16H 20/40; G16H 10/60; G16H 50/20; G16H 40/63
USPC ....................................................... 705/2–4
See application file for complete search history.

(56) References Cited

U.S. PATENT DOCUMENTS

| | | |
|---|---|---|
| 4,706,652 A | 11/1987 | Horowitz |
| 4,754,745 A | 7/1988 | Horowitz |
| 4,946,435 A | 8/1990 | Suthanthiran et al. |
| 5,030,195 A | 7/1991 | Nardi |
| D381,080 S | 7/1997 | Ohata |
| 5,772,574 A | 6/1998 | Nanko |
| 5,803,895 A | 9/1998 | Kronholz et al. |
| 5,840,008 A | 11/1998 | Klein et al. |
| 5,871,708 A | 2/1999 | Park et al. |
| D408,957 S | 4/1999 | Sandor |
| 5,967,966 A | 10/1999 | Kronholz et al. |
| 5,997,842 A | 12/1999 | Chen |
| 6,017,482 A | 1/2000 | Anders et al. |
| D420,452 S | 2/2000 | Cardy |
| D420,745 S | 2/2000 | Cardy |
| D420,746 S | 2/2000 | Cardy |
| 6,066,302 A | 5/2000 | Bray |
| 6,129,670 A | 10/2000 | Burdette et al. |
| D443,061 S | 5/2001 | Bergstrom et al. |
| 6,248,057 B1 | 6/2001 | Mavity et al. |
| 6,327,490 B1 | 12/2001 | Spetz |
| 6,352,500 B1 | 3/2002 | Halpern |
| 6,358,195 B1 | 3/2002 | Green et al. |
| 6,360,116 B1 * | 3/2002 | Jackson, Jr. .......... A61N 5/1027 600/427 |
| 6,385,477 B1 | 5/2002 | Werner et al. |
| 6,450,937 B1 | 9/2002 | Mercereau et al. |
| 6,471,631 B1 | 10/2002 | Slater et al. |
| 6,512,943 B1 | 1/2003 | Kelcz |
| 6,539,247 B2 | 3/2003 | Spetz |
| 6,547,816 B1 | 4/2003 | O'Foghludha |
| 6,572,526 B1 | 6/2003 | Ford |
| 6,666,811 B1 | 12/2003 | Good |
| 6,679,824 B1 | 1/2004 | Reed et al. |
| 6,712,508 B2 | 3/2004 | Nilsson et al. |
| 6,712,782 B2 | 3/2004 | Ford |
| D488,864 S | 4/2004 | Fago et al. |
| 6,770,021 B2 | 8/2004 | Halpern |
| 6,787,042 B2 | 9/2004 | Bond et al. |
| 6,790,170 B2 | 9/2004 | Moody et al. |
| 6,846,282 B1 | 1/2005 | Ford |
| 6,994,688 B2 | 2/2006 | Brauckman et al. |
| 7,011,619 B1 | 3/2006 | Lewis |
| 7,070,554 B2 | 7/2006 | White et al. |
| 7,118,729 B1 | 10/2006 | O'Foghludha |
| 7,190,895 B1 | 3/2007 | Groves et al. |
| D561,896 S | 2/2008 | Jones |
| 7,410,458 B2 | 8/2008 | Bray et al. |
| D580,056 S | 11/2008 | Orthner |
| D580,057 S | 11/2008 | Ramadani |
| 7,686,756 B2 | 3/2010 | Black et al. |
| 7,736,293 B2 | 6/2010 | Lamoureux et al. |
| 7,749,151 B2 | 7/2010 | Ferguson |
| 7,776,310 B2 | 8/2010 | Kaplan |
| 7,972,261 B2 | 7/2011 | Lamoureux et al. |
| 8,012,455 B2 | 9/2011 | O'Foghludha |
| 8,021,291 B2 | 9/2011 | Lamoureux et al. |
| 8,039,790 B2 | 10/2011 | Cho et al. |
| 8,097,236 B2 | 1/2012 | Aston et al. |
| 8,114,007 B2 | 2/2012 | Lamoureux et al. |
| D657,474 S | 4/2012 | Dona |
| 8,187,159 B2 | 5/2012 | Lamoureux et al. |
| 8,192,345 B2 | 6/2012 | Lamoureux et al. |
| 8,226,539 B2 | 7/2012 | Cutrer |
| 8,293,630 B2 | 10/2012 | Dunkley et al. |
| 8,323,172 B2 | 12/2012 | Black et al. |
| 8,366,598 B2 | 2/2013 | Lamoureux et al. |
| D680,649 S | 4/2013 | Jagger et al. |
| D681,210 S | 4/2013 | Beiriger et al. |
| D681,812 S | 5/2013 | Farris et al. |
| D681,813 S | 5/2013 | Jagger et al. |
| 8,454,489 B2 | 6/2013 | Drobnik et al. |
| D686,341 S | 7/2013 | Nakaji et al. |
| D686,744 S | 7/2013 | Nakaji et al. |
| D686,745 S | 7/2013 | Nakaji et al. |
| D686,746 S | 7/2013 | Nakaji et al. |
| D686,747 S | 7/2013 | Nakaji et al. |
| D686,748 S | 7/2013 | Nakaji et al. |
| D687,568 S | 8/2013 | Nakaji et al. |
| D687,966 S | 8/2013 | Nakaji et al. |
| D687,967 S | 8/2013 | Nakaji et al. |
| 8,600,130 B2 | 12/2013 | Eriksson Järliden |
| 8,605,966 B2 | 12/2013 | Eriksson Järliden |
| 8,647,603 B2 | 2/2014 | Aston et al. |
| 8,771,162 B2 | 7/2014 | Lamoureux et al. |
| 8,790,235 B2 | 7/2014 | Lamoureux et al. |
| 8,795,146 B2 | 8/2014 | Lamoureux et al. |
| 8,825,136 B2 | 9/2014 | Giller et al. |
| 8,827,884 B2 | 9/2014 | Ribbing et al. |
| 8,834,837 B2 | 9/2014 | Kelson et al. |
| 8,876,684 B1 | 11/2014 | Nakaji et al. |
| 8,878,464 B2 | 11/2014 | Clayton et al. |
| 8,894,969 B2 | 11/2014 | Kelson et al. |
| 8,915,834 B1 | 12/2014 | Lamoureux et al. |
| 8,939,881 B2 | 1/2015 | Nakaji et al. |
| 8,974,364 B1 | 3/2015 | Nakaji et al. |
| 9,022,914 B2 | 5/2015 | Clayton et al. |
| 9,022,915 B2 | 5/2015 | Nakaji et al. |
| 9,180,310 B2 | 11/2015 | Black et al. |
| 9,358,377 B2 | 6/2016 | Black et al. |
| 9,403,033 B1 | 8/2016 | Brachman |
| 9,409,038 B2 | 8/2016 | Nakaji et al. |
| 9,492,683 B2 | 11/2016 | Brachman et al. |
| 9,526,463 B2 | 12/2016 | Brachman et al. |
| 9,545,525 B2 | 1/2017 | Nakaji et al. |
| 9,642,999 B2 | 5/2017 | Sutton et al. |
| 9,788,909 B2 | 10/2017 | Larkin et al. |
| 9,789,608 B2 | 10/2017 | Itkowitz et al. |
| 9,808,650 B2 | 11/2017 | White et al. |
| 9,821,174 B1 | 11/2017 | Fram et al. |
| 10,058,713 B2 | 8/2018 | Kelson et al. |
| 10,080,909 B2 | 9/2018 | Brachman et al. |
| 10,085,699 B2 | 10/2018 | Brachman et al. |
| 10,265,542 B2 | 4/2019 | Brachman et al. |
| 10,328,278 B2 | 6/2019 | Krachon et al. |
| 10,350,431 B2 | 7/2019 | Nakaji et al. |
| 10,449,386 B2 | 10/2019 | Bask et al. |
| 10,646,724 B2 | 5/2020 | Hoedl et al. |
| 10,888,710 B1 | 1/2021 | Brachman et al. |
| 10,981,018 B2 | 4/2021 | Baker et al. |
| 11,278,736 B2 | 3/2022 | Brachman et al. |
| 11,298,846 B1 | 4/2022 | Hanberg et al. |
| 2001/0044567 A1 | 11/2001 | Zamora et al. |
| 2002/0055666 A1 | 5/2002 | Hunter |
| 2002/0058854 A1 | 5/2002 | Creed et al. |
| 2002/0120174 A1 | 8/2002 | Steele, Sr. et al. |
| 2003/0045769 A1 | 3/2003 | Kalas et al. |
| 2003/0088141 A1 | 5/2003 | Terwilliger et al. |
| 2003/0109769 A1 | 6/2003 | Lowery et al. |
| 2003/0113359 A1 | 6/2003 | Iyer et al. |
| 2003/0130573 A1 | 7/2003 | Yu et al. |
| 2003/0149329 A1 | 8/2003 | O'Foghludha |
| 2003/0208096 A1 | 11/2003 | Tam |
| 2004/0091421 A1 | 5/2004 | Aston et al. |
| 2004/0109823 A1 | 6/2004 | Kaplan |
| 2004/0116767 A1 | 6/2004 | Lebovic et al. |
| 2004/0225176 A1 | 11/2004 | Flanagan et al. |
| 2004/0242953 A1 | 12/2004 | Good |

(56) References Cited

U.S. PATENT DOCUMENTS

| | | | |
|---|---|---|---|
| 2005/0035310 A1 | 2/2005 | Drobnik et al. | |
| 2005/0111621 A1* | 5/2005 | Riker | G16H 20/40 378/65 |
| 2005/0244045 A1 | 11/2005 | Eriksson | |
| 2005/0267319 A1 | 12/2005 | White et al. | |
| 2006/0015030 A1* | 1/2006 | Poulin | A61B 34/20 600/424 |
| 2006/0063962 A1 | 3/2006 | Drobnik et al. | |
| 2006/0173236 A1 | 8/2006 | White et al. | |
| 2006/0235365 A1 | 10/2006 | Terwilliger | |
| 2006/0253048 A1 | 11/2006 | Jones | |
| 2007/0135673 A1 | 6/2007 | Elliott et al. | |
| 2007/0167665 A1 | 7/2007 | Hermann et al. | |
| 2007/0190761 A1 | 8/2007 | Dunkley et al. | |
| 2007/0225544 A1 | 9/2007 | Vance et al. | |
| 2008/0004714 A1 | 1/2008 | Lieberman | |
| 2008/0009661 A1 | 1/2008 | Lamoureux et al. | |
| 2008/0055580 A1 | 3/2008 | Black et al. | |
| 2008/0146861 A1 | 6/2008 | Murphy et al. | |
| 2008/0221384 A1 | 9/2008 | Chi Sing et al. | |
| 2009/0012347 A1 | 1/2009 | Helle | |
| 2009/0069625 A1 | 3/2009 | Helle et al. | |
| 2009/0131735 A1 | 5/2009 | Drobnik et al. | |
| 2009/0136422 A1 | 5/2009 | Kelson et al. | |
| 2009/0156880 A1 | 6/2009 | Allan et al. | |
| 2009/0253950 A1 | 10/2009 | Rapach et al. | |
| 2009/0271715 A1 | 10/2009 | Tumuluri | |
| 2009/0275793 A1 | 11/2009 | Black et al. | |
| 2010/0015042 A1 | 1/2010 | Keisari et al. | |
| 2010/0056908 A1 | 3/2010 | Giller et al. | |
| 2010/0200778 A1 | 8/2010 | Drobnik et al. | |
| 2010/0228074 A1 | 9/2010 | Drobnik et al. | |
| 2010/0268015 A1 | 10/2010 | Drobnik et al. | |
| 2010/0288916 A1 | 11/2010 | Cho et al. | |
| 2010/0324353 A1 | 12/2010 | Helle | |
| 2011/0013818 A1 | 1/2011 | Eriksson Järliden | |
| 2011/0206252 A1 | 8/2011 | Eriksson Järliden | |
| 2012/0108882 A1 | 5/2012 | Hoedl | |
| 2012/0165957 A1 | 6/2012 | Everland et al. | |
| 2013/0102832 A1 | 4/2013 | Hoedl et al. | |
| 2013/0102891 A1* | 4/2013 | Binnekamp | A61N 5/1048 600/424 |
| 2013/0131434 A1 | 5/2013 | Nakaji et al. | |
| 2013/0209965 A1* | 8/2013 | Fisker | A61C 9/0046 433/220 |
| 2013/0338423 A1 | 12/2013 | Nakaji et al. | |
| 2014/0275715 A1 | 9/2014 | Brachman et al. | |
| 2014/0296612 A1 | 10/2014 | Schwartz | |
| 2014/0316187 A1 | 10/2014 | Nakaji et al. | |
| 2015/0057487 A1 | 2/2015 | Nakaji et al. | |
| 2015/0105605 A1 | 4/2015 | Finger et al. | |
| 2015/0140535 A1 | 5/2015 | Geri et al. | |
| 2015/0157879 A1* | 6/2015 | Wu | A61N 5/1067 378/8 |
| 2015/0196778 A1 | 7/2015 | Nakaji et al. | |
| 2015/0321024 A1 | 11/2015 | Nakaji et al. | |
| 2015/0367144 A1 | 12/2015 | Flynn et al. | |
| 2016/0242855 A1 | 8/2016 | Fichtinger et al. | |
| 2016/0367709 A1 | 12/2016 | Aston et al. | |
| 2017/0021191 A1 | 1/2017 | Brachman et al. | |
| 2017/0120073 A1 | 5/2017 | Brachman et al. | |
| 2017/0215824 A1 | 8/2017 | Brachman et al. | |
| 2017/0252575 A1 | 9/2017 | Nakaji et al. | |
| 2018/0333509 A1 | 11/2018 | Aston et al. | |
| 2018/0345038 A1 | 12/2018 | Kelson et al. | |
| 2019/0240504 A1 | 8/2019 | Brachman et al. | |
| 2020/0047001 A1 | 2/2020 | Nakaji et al. | |
| 2020/0206372 A1 | 7/2020 | Aston et al. | |
| 2020/0261740 A1 | 8/2020 | Baker et al. | |
| 2020/0261741 A1 | 8/2020 | Herskovic | |
| 2020/0406059 A1 | 12/2020 | Kelson et al. | |
| 2021/0008233 A1 | 1/2021 | Kelson et al. | |
| 2021/0128945 A1 | 5/2021 | Schmidt et al. | |
| 2021/0154340 A1 | 5/2021 | Kelson et al. | |
| 2021/0183492 A1 | 6/2021 | Park | |
| 2021/0236850 A1 | 8/2021 | Baker et al. | |
| 2021/0353960 A1 | 11/2021 | Sienko et al. | |
| 2021/0370083 A1 | 12/2021 | Giladi et al. | |
| 2021/0379096 A1 | 12/2021 | Dornankevich et al. | |
| 2022/0096854 A1 | 3/2022 | Carlson | |
| 2022/0184418 A1 | 6/2022 | Arazi et al. | |
| 2022/0212035 A1 | 7/2022 | Kelson et al. | |

FOREIGN PATENT DOCUMENTS

| | | |
|---|---|---|
| CA | 2834559 | 11/2018 |
| CA | 3017174 | 1/2020 |
| DE | 613 528 | 5/1935 |
| EP | 0 292 630 B1 | 8/1995 |
| EP | 0 906 769 A2 | 4/1999 |
| EP | 2701803 B1 | 8/2018 |
| EP | 3456384 | 3/2019 |
| JP | S52-9424 | 7/1975 |
| JP | H09-028810 | 4/1997 |
| JP | 2001-266903 | 9/2001 |
| JP | 3095304 | 7/2003 |
| JP | 2007-512112 | 5/2007 |
| JP | 2009-515603 | 4/2009 |
| JP | 2010-536529 | 12/2010 |
| JP | 6365983 | 7/2018 |
| WO | WO 2007/106531 A1 | 9/2007 |
| WO | WO 2012/100206 A2 | 7/2012 |
| WO | WO 2012/149580 A1 | 11/2012 |
| WO | WO 2016/171961 | 10/2016 |
| WO | WO 2016/179420 | 11/2016 |

OTHER PUBLICATIONS

International Search Report; International Application No. PCT/US2012/035907, dated Sep. 26, 2012; 3 pages.

International Search Report; International Application No. PCT/US2012/035909, dated Aug. 30, 2012; 3 pages.

Crepeau, R.H., et al., "Image Processing of Imperfect Protein Arrays: Sectioned Crystals and Tubulin Sheets and Rings". Elec. Microsc. Soc. Amer. Proc. 40:84-87, 1982.

Crepeau, R.H., et al., "Reconstruction of imperfectly ordered zinc-induced tubulin sheets using cross-correlation and real space averaging". Ultramicroscopy, 6, 7-18, 1981.

Dagnew, E., et al., "Management of newly diagnosed single brain metastasis using resection and permanent iodine-125 seeds without initial whole-brain radiotherapy: a two institution experience". Neurosurg Focus. 15; 22(3):E3, 2007.

Delaney, T.F., et al., "Intraoperative dural irradiation by customized 192 iridium and 90 Yttrium brachytherapy plaques". Int. J. Radiat Oncol Biol Phys. 57(1): 239-245, 2003.

Ewersten, et al., "Biopsy Guided by Real-Time Sonography Fused with MRI: A Phantom Study", American Journal of Roentgenology. 2008; 190: 1672-1674. 10.2214/AJR.07.2587.

Gutin, P.H., et al., "A coaxial catheter system for after loading radioactive sources for the interstitial irradiation of brain tumors. Technical note". J. Neurosurg 56: 734-735, 1982.

Gutin, P.H., et al., "Brachytherapy of recurrent tumors of the skull base and spine with iodine-125 sources". Neurosurgery 20:938-945, 1987.

Hamilton, A.J., et al., "The use of gold foil wrapping for radiation protection of the spinal cord for recurrent tumor therapy". Int. J. Radiat Oncol Biol Phys. 32(2):507-511, 1995.

Hilaris, B.S., et al., "Interstitial irradiation for unresectable carcinoma of the lung". Ann Thoracic Surg; 20:491-500, 1975.

Hilaris, B.S., et al., "Intraoperative radiotherapy in stage I and II lung cancer". Semin Surg Oncol. 3:22-32, 1987.

Huang, K., et al., "Surgical resection and permanent iodine-125 brachytherapy for brain metastases". J. Neurooncol. 91:83-93, 2009.

Jenkins, H.P., et al., "Clinical and experimental observations on the use of a gelatin sponge or foam". Surg 20:124-132, 1946.

Kneschaurek, P. et al.: "Die Flabmethode Zur Intraoperativen Bestrahlung. Öthe Flab-Method for Intraoperative Radiation Therapy",

(56) References Cited

OTHER PUBLICATIONS

Strahlentherapie und Oknologie, Urban Und Vogel, Muenchen, DE, vol. 171, No. 2; Feb. 1, 1995, pp. 61-69, XP000610565, ISSN:0179-7158, x-abstract.

Marchese, M.J., et al., "A versatile permanent planar implant technique utilizing iodine-125 seeds imbedded in gelfoam". Int J Radiat Oncol Biol Phys 10:747-751, 1984.

Miller, S., et al., "Advances in the virtual reality interstitial brachytherapy system." Engineering Solutions for the Next Millenium. 1999 IEEE Canadian Conference on Electrical and Computer Engineering (Cat. No. 99TH8411). vol. 1. IEEE, 1999.

Murphy, M.K., et al., "Evaluation of the new cesium-131 seed for use in low-energy x-ray brachytherapy". Med Phy 31(6): 1529-1538, Jun. 2004.

Nori, D., et al., "Intraoperative brachytherapy using Gelfoam radioactive plaque implants for resected stage III non-small-cell lung cancer with positive margin: A pilot study". J Surg Oncol. 60:257-261, 1995.

Parashar, B., et al., "Cesium-131 permanent seed brachytherapy: Dosimetric evaluation and radiation exposure to surgeons, radiation oncologists, and staff". Brachytherapy. 10:508-511, 2011.

Patel, S., et al., "Permanent iodine-125 interstitial implants for the treatment of recurrent Glioblastoma Multiforme". Neurosurgery 46 (5) 1123-1128, 2000.

Rivard, M.J., "Brachytherapy dosimetry parameters calculated for a 131 Cs source". Med Phys. 34(2): 754-765, 2007.

Rogers, C.L., et al., "Surgery and permanent 125-1 seed paraspinal brachytherapy for malignant tumors with spinal cord compression". Int. J. Radial Oncol Biol Phys. 54(2): 505-513, 2002.

Wernicke, A.G., et al., "Feasibility and safety of Gliasite brachytherapy in the treatment of CNS tumors following neurosurgical resection". J. Cancer Res Ther. 6(1), 65-74, Jan.-Mar. 2010.

CivaSheet; "Precision Therapy Without the Beam"; CivaTech Oncology Inc.; CivaTech; https://civatechoncology.com/professionals/civasheet/2 pages; Accessed on Oct. 2018.

CivaSheet; "Precision Therapy Without the Beam"; CivaTech Oncology Inc.; CivaTech; https://civatechoncology.com/products-2/products/; 5 pages; Accessed on Oct. 2018.

Aima, Manik et al.; "Dosimetric Characterization of a New Directional Low-Dose Rate Brachytherapy Source"; Department of Medical Physics; Mar. 11, 2018; 32 pages;.

Rivard, Mark J.; "A Directional Pd Brachytherapy Device: Dosimetric Characterization and Practical Aspects for Clinical Use"; Department of Radiation Oncology; Brachytherapy 16 (2017) pp. 421-432.

Office Action dated Apr. 2, 2015; European Patent Application No. 12724426.7; 5 pages.

Office Action dated Oct. 30, 2015; European Patent Application No. 12724426.7; 4 pages.

Office Action dated Feb. 9, 2016; Japanese Application No. 2014-508190; 7 pages including english translation.

International Search Report; International Application No. PCT/US2016/031035; filed May 5, 2016; 15 pages; dated Aug. 5, 2016.

International Search Report and Written Opinion; International Application No. PCT/US2016/027143, filed Apr. 12, 2016; dated Aug. 25, 2016; 7 pages.

Decision of Rejection dated Feb. 4, 2016, Japanese Patent Application No. 2014-508190 with English Translation; 4 pages.

Search and Examination Report; Application No. P1140/13; Filed on Oct. 24, 2013 (PCT dated Apr. 30, 2012); 10 pages.

Summons to Attend Oral Proceedings dated Aug. 18, 2017; European Application No. 12724426.7; 5 pages.

Office Action dated Nov. 2, 2017; European Patent Application No. 12724427.5; 4 pages.

Extended European Search Report; Application No. 18186392.9; dated Jan. 7, 2019; 7 pages.

\* cited by examiner

RADIOACTIVE IMPLANT PLANNING SYSTEM AND PLACEMENT GUIDE SYSTEM

CROSS-REFERENCE TO RELATED APPLICATIONS

This application is a continuation of U.S. application Ser. No. 15/791,962, filed on Oct. 24, 2017, which is a continuation of U.S. application Ser. No. 15/017,461, filed on Feb. 5, 2016, now U.S. Pat. No. 9,821,174, which is a nonprovisional of and claims the benefit of U.S. Provisional Application No. 62/113,252, filed on Feb. 6, 2015, and U.S. Provisional Application No. 62/205,172, filed on Aug. 14, 2015 the entirety of which is hereby incorporated herein by reference.

BACKGROUND

Implants have been developed that emit radiation or chemicals and can be placed within or on a patient's body, for example for the purpose of treating disease or improving health. For example, implants may contain radioactive material to treat adjacent cancer. In another example, implants may emit chemical agents that could for example, treat disease, or promote tissue healing.

SUMMARY

There is a need for systems and methods that make the planning of implant type, number, strength, location, and/or configuration efficient, intuitive, and accurate. In addition, once a plan for implants has been created, there is a need for ways of guiding the user, for example the surgeon, in accurately and efficiently placing the physical implants in or on the body.

Multiple features will be discussed herein that address these needs. First, in one embodiment an implant planning system provides novel user interfaces to allow the user to create a plan for implants in a way that is efficient, intuitive, and accurate. Second, an implant placement guide system makes it simple, intuitive, and accurate for the surgeon to place physical implants based on the implant plan. In some embodiments the implant placement guide system may even control medical equipment, such as robotic surgical equipment, to place implants into a patient, such as with limited or no input from the surgeon.

Various features of these improvements are discussed below, and may be used together in various combinations or independently. For example, the implant placement guide system (also referred to herein as the "implant placement system" or simply "the system") could be used to aid a surgeon in placing physical implants based on an implant plan developed with software systems other than those disclosed herein with reference to the implant planning system. Similarly, an implant plan developed by the system may be implemented using other implantation systems.

While the examples shown use radioactive implants placed on the brain for the purposes of treating cancer, the systems and methods described herein may be used in many other applications.

In the examples shown, a photographic image of the brain is used for the purposes of planning implant placement. However, the planning image may be any two-dimensional (2D) image or three-dimensional (3D) surface, for example created using 3D surface rendering of information acquired using Magnetic resonance imaging (MRI), computed tomography (CT), ultrasound, or optical imaging.

In one embodiment, a computing system for developing a treatment plan for placement of radioactive implants on a treatment surface of a patient comprises a computer processor and a computer readable storage medium storing program instructions configured for execution by the computer processor. In one embodiment, the program instructions cause the computing system to generate a planning user interface including at least a display frame for viewing anatomical images, and a virtual implant toolbar including at least a first selectable tool configured to allow adding of virtual implants to the display frame, and to display the planning user interface on a display device of the computing system. In some embodiments, the instructions further cause the computing system to receive, from a user of the computing system, identification of a first medical image as a planning image, the first medical image depicting a treatment surface of a patient, display the planning image in the display frame of the planning user interface, receive, from the user of the computing system, selection of first virtual implant characteristics for a first virtual implant to be added to a treatment plan for the patient, the first virtual implant characteristics including at least a first virtual implant shape, a first virtual implant size, and a first radiation characteristic of a first seed associated with the first virtual implant. In some embodiments, the instructions further cause the computing system to receive, from the user of the computing system, selection of second virtual implant characteristics for a second virtual implant to be added to a treatment plan for the patient, the second virtual implant characteristics including at least a second virtual implant shape, a second virtual implant size, and a second radiation characteristic of a second seed associated with the second virtual implant. In some embodiments, the instructions further cause the computing system to display the first virtual implant and the second virtual implant in the display frame, wherein the first and second virtual implants are at least partially transparent such that a portion of the planning image whereupon the first and second virtual implants are placed is visible through the at least partially transparent first and second virtual implants. In some embodiments, the instructions further cause the computing system to receive, from the user of the computing system, selection of a second selectable tool of the virtual implant toolbar configured to initiate movement of a selected one or more virtual implants within the display frame, receive movement inputs associated with the first virtual implant causing the first virtual implant to contact the second virtual implant, and apply a physics algorithm, and based on the movement of the first virtual implant into the second virtual implant, to determine a movement of the second virtual implant in response to a virtual force exerted by the first virtual implant. In some embodiments, the instructions further cause the computing system to calculate a radiation isodose plan indicative of an expected radiation dosage from combination of first radiation from the first virtual implant and second radiation from the second virtual implant, wherein the radiation isodose plan includes a plurality of isodose curves each indicative of a particular radiation level along the respective isodose curve and a plurality of fill patterns between adjacent isodose curves, wherein each fill pattern represents a radiation range between adjacent isodose curves and depict the radiation isodose plan in the display frame, wherein the radiation isodose plan has a transparency of less than one hundred percent, such that at least a portion of the first and second virtual implants and the planning image underneath the radiation isodose plan are visible. In some embodiments, the instructions further cause the computing system to, in response to a treatment plan generation command from the user of the computing system, generate treatment plan data usable to procure a first physical implant associated with the first virtual implant and a second physical implant associated with the second virtual implant, the treatment plan data including at least some of the first virtual implant characteristics and at least some of the second virtual implant characteristics.

In some embodiments, the instructions further cause the computing system to transmit the treatment plan data to an implant provider with a requested delivery date and location for delivery of physical implants associated with each of the virtual implants indicated in the treatment plan.

In some embodiments, the treatment plan data is automatically transmitted via an electronic communication to the implant provider.

In some embodiments, the program instructions are further configured to cause the computing system to receive, from the user of the computing system, selection of a second selectable tool of the virtual implant toolbar configured to initiate movement of a selected one or more virtual implants within the display frame, wherein the virtual carriers are configured to interact with one another in a manner similar to interactions between corresponding physical implants.

In some embodiments, the program instructions are further configured to cause the computing system to receive, from the user of the computing system, a request to update the planning image to a second medical image of the patient, wherein the medical image of the patient and the second medical image of the patient depict a common plane of the patient's anatomy.

In some embodiments, the program instructions are further configured to cause the computing system to receive, from the user of the computing system, a request to replace the planning image with a live video feed of the treatment surface.

In some embodiments, the program instructions are further configured to cause the computing system to execute a registration process to align anatomical features of the second medical image with those of the medical image such that each particular anatomical feature in the second medical image will be rendered at a same location in the display frame as the particular anatomical feature is rendered in the medical image displayed in the display frame.

In some embodiments, the program instructions are further configured to cause the computing system to replace the medical image with the second medical image in the display frame, while maintaining display of the first virtual implant, the second virtual implant, and the radiation isodose graph.

In some embodiments, the planning user interface further includes an isodose level user interface control selectable by the user to adjust a plane parallel to the treatment surface in the planning image at which the isodose curves are calculated, wherein adjustment of the plane initiates real-time updating and display of the radiation isodose plan at the updated plane.

In some embodiments, the planning user interface further includes an isodose transparency user interface control selectable by the user to adjust transparency of the radiation isodose plan.

In some embodiments, the isodose transparency user control includes a first transparency button that, when selected, adjusts transparency of the radiation isodose plan to fifty percent and a second transparency button that, when selected, adjusts transparency of the radiation isodose plan to seventy-five percent.

In some embodiments, the virtual implant toolbar further includes a seed strength user interface control selectable by the user to adjust seed strength of a selected virtual implant.

In some embodiments, seed strengths that are available for selection in the seed strength user interface control are limited to seed strengths that are available for use at a determine implantation time.

In some embodiments, the first virtual implant characteristics indicate a position of the first seed between a top and bottom surface of the first virtual implant, wherein the position has a default at a location wherein the first seed is closer to the top surface such that more radiation is emitted from a top surface of a corresponding physical implant than a bottom surface of the corresponding physical implant, wherein the virtual implant toolbar further includes a flip control. In some embodiments, in response to the user selecting the flip control and selecting the first virtual implant the position of the first seed between the top and bottom surfaces of the first virtual implant is updated so that the position of the first seed is closer to the bottom surface such that more radiation is emitted from the bottom surface of the corresponding physical implant than the top surface of the corresponding physical implant, and the radiation isodose plan is updated to reflect any changes to the calculated dosage at the isodose level.

In some embodiments, the virtual implant toolbar further includes a composite implant control configured to create an association between the first virtual implant and the second virtual implant, wherein in response to the user selecting the composite implant control a positional relation between the first virtual implant and the second virtual implant is determined and a composite implant comprising the first and second virtual implant in the determined positional relationship is defined, wherein the composite implant is moveable by movement of either of the first or second virtual implant.

In some embodiments, the virtual implant toolbar further includes a composite implant control configured to create a composite implant including two or more virtual implants each having common implant characteristics, wherein the composite implant is displayed in the display frame and is moveable in response to movement of any of the two or more virtual implants.

In some embodiments, the virtual implant toolbar further includes a flip control and, in response to the user selecting the flip control and selecting the first virtual implant of the composite implant, the first virtual implant is disassociated from the composite implant such that a position of a first seed in the first virtual implant is updated, but a position of the second seed in the second virtual implant is not updated.

In another embodiment, a computing system comprises a computer processor, and a computer readable storage medium storing program instructions configured for execution by the computer processor. In some embodiments, the computing system generates a planning user interface including at least a display frame for viewing anatomical images, and a virtual implant toolbar including at least a first selectable tool configured to allow adding of virtual implants to the display frame, and displays the planning user interface on a display device of the computing system. In some embodiments, the instructions further cause the computing system to receive, from a user of the computing system, identification of a first medical image as a planning image, the first medical image depicting a treatment surface of a patient, and display the planning image in the display frame of the planning user interface. In some embodiments, the instructions further cause the computing system to receive, from the user of the computing system, selection of first virtual implant characteristics for a first virtual implant to be added to a treatment plan for the patient, the first virtual implant characteristics including at least a first virtual implant shape, a first virtual implant size, and a first radiation characteristic of a first seed associated with the first virtual implant, receive, from the user of the computing system, selection of second virtual implant characteristics for a second virtual implant to be added to a treatment plan for the patient, the second virtual implant characteristics including at least a second virtual implant shape, a second virtual implant size, and a second radiation characteristic of a second seed associated with the second virtual implant, and display the first virtual implant and the second virtual implant in the display frame. In some embodiments, the instructions further cause the computing system to determine a radiation range prescribed for treatment of the patient, receive, from the user of the computing system, drawing inputs indicating a treatment area of the planning image, and depict at least an outline of the treatment area on the treatment image. In some embodiments, the instructions further cause the computing system to calculate for each of a plurality of subregions within the treatment area an expected radiation level based on first radiation from the first virtual implant and second radiation from the second virtual implant, and depict on the treatment area one or more of: a first color or visual indication of any subregions having expected radiation levels below the prescribed radiation range, a second color or visual indication of any subregions having expected radiation levels above the prescribed radiation range, or a third color or visual indication of any subregions having expected radiation levels within the prescribed radiation range, wherein all subregions of the treatment area are associated with one of the first, second, or third color or visual indication.

In some embodiments, the first color or visual indication is a yellow color, the second color or visual indication is a red color, and the third color or visual indication is a green color.

In some embodiments, the drawing inputs are provided via movement of a finger or stylus on a touch-sensitive display or input device, or movement of a mouse, to draw the treatment area.

DETAILED DESCRIPTION

Definitions

Figure 1:
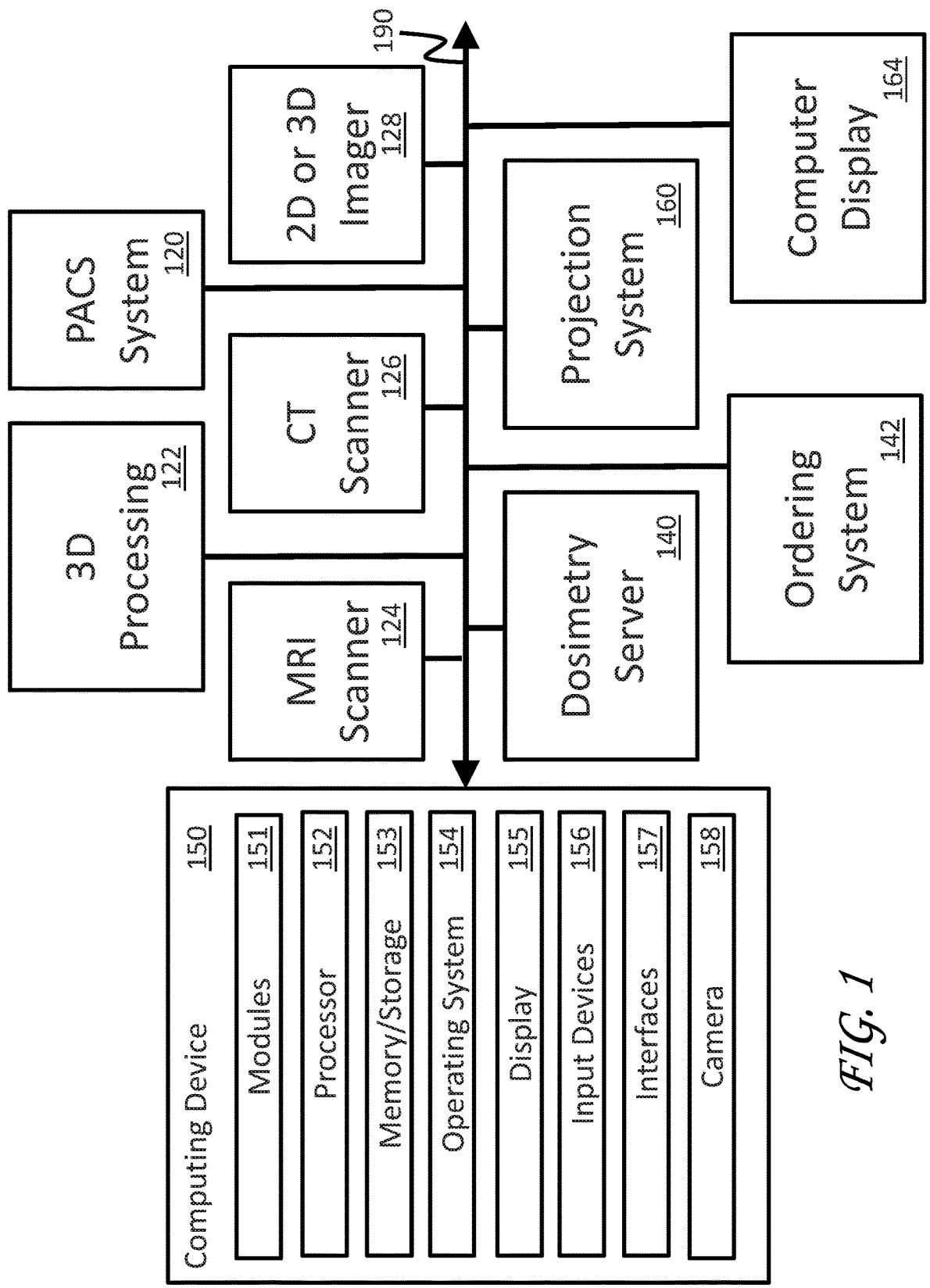
FIG. 1 Illustrates an example system that may be used to implement the inventions described herein.

In order to facilitate an understanding of the systems and methods discussed herein, a number of terms are defined below. The terms defined below, as well as other terms used herein, should be construed to include the provided definitions, the ordinary and customary meaning of the terms, and/or any other implied meaning for the respective terms. Thus, the definitions below do not limit the meaning of these terms, but only provide exemplary definitions.

Implant planning system (also referred to herein as a "planning system"): One or more computing systems that executes planning software in order to generate a planning system user interface in which a user can efficiently, intuitively, and accurately create a treatment plan by manipulating virtual implants as if they are physical objects. For example, virtual implants may be manipulated to change an expected output/consequence of associated physical implants, such as radiation dose levels, drug concentrations, etc., in order to achieve a desired prescribed dosage.

Implant placement guide system (else referred to herein as a "guide system" or an "implant guide system): One or more computing systems that aids a user and/or other system (e.g., a robotic surgical instrument) in implementing a treatment plan developed by the implant planning system (or other planning system), such as by executing implant guidance software. In some embodiments, the implant guidance software displays (e.g., on a display device in an operating room) the locations, types, strengths, and/or configuration of virtual implants simultaneously with imaging of the anatomy at the time of implantation to guide the surgeon, or other user, in placing the implants. In some embodiments, the implant guidance software is in communication with a projection device (e.g., a high definition video projector in an operating room) and transmits portions of the treatment plan (e.g., the locations, types, strengths, and/or configurations of virtual implants) for projection onto a treatment surface of the patient.

In some embodiments, an "implant planning system" includes both the implant planning software and the implant guidance software. Thus, references to an implant planning system herein may refer to a system that provides one or both of the implant planning software and/or the implant guidance software.

Tumor: an abnormal growth of tissue resulting from uncontrolled, progressive multiplication of cells. Tumors can be benign or malignant.

Tumor bed: an anatomical area of a patient (e.g., a human or other mammal) where a tumor exists (pre-operative tumor bed) and/or an area surrounding a surgically removed tumor (post-operative tumor bed), such as a cranial cavity from which a tumor was surgically removed. Even after surgical removal of a tumor, the remaining tumor bed of the patient may include tumor cells.

Treatment area: an anatomical area that is targeted for delivery of radiation, such as from one or more radiation delivery devices (e.g., the implants discussed below). A treatment area may include tissue below and/or around a location where the radiation delivery devices are positioned, such as an anatomical area of a tumor, a tumor bed, or some other area where radiation treatment is desired.

Treatment surface: an anatomical surface of a patient where a radiation (or other treatment) delivery device is to be placed to deliver radiation to a treatment area, such as the treatment surface itself and/or tissue below and/or around the treatment surface. A treatment surface may be a portion of a tumor bed or any other anatomical surface. For example, if a tumor bed is surgically created, such as a cranial cavity that is created after removal of a brain tumor, the treatment surface may include some or all of an exposed surface of the post-operative tumor bed and/or some portion of tissue surrounding the cavity.

Brachytherapy: radiation treatment in which the radiation delivery device is placed directly on and/or close to a treatment surface of the body, such as directly on the surface of the body, within the body, or in a tumor bed. For example, brachytherapy may be intracavitary, such as in cranial or gynecologic malignancies; intraluminal, such as in esophageal or lung cancers; external, such as in cancers of the skin; and/or interstitial, such as in treatment of various central nervous system tumors as well as extracranial tumors of the head, neck, lung, soft tissue, gynecologic sites, rectum, liver, prostate, and penis. In the embodiments discussed herein, the implants are placed on the treatment surface, rather than being embedded within tissue (such as by a syringe injecting a radioactive seed below an exposed surface of a surgical cavity). However, the treatment planning software may be used in planning of placement of any type of implant, including the surface mounted implants discussed herein as well as other types of implants such as shallow or deep tissue implants.

Seed: a radioactive material that is configured for delivery of radiation to a treatment area. A seed may be in various shapes and sizes, such as cylinder, cone, sphere, pyramid, cube, prism, rectangular prism, triangular prism, and/or any combination of these or other shapes. While seeds are generally referred to herein as cylindrical, any other shape or size of seed may alternatively be used in the various systems and methods discussed herein. Seeds may comprise any combination of one or more of multiple radioactive components, such as Cs 131, Ir 192, 1125, Pd 103, for example. Seeds may include a protective outer shell that partially or fully encases the radioactive material.

Carrier: a substrate that holds or contains a radioactive seed. A carrier that contains one or more seeds is a radiation delivery device. Carriers may be configured for permanent implantation into a tumor bed, such as to provide radioactive energy to a treatment surface surrounding an area where a tumor has been removed in order to treat any remaining malignant tissue. Carriers can be composed of various materials and take on various shapes and sizes. Examples carriers, such as carriers having various sizes, shapes, configurations, etc., are included in the following patent and patent application, each of which is hereby incorporated by reference in its entirety and for all purposes: U.S. patent application Ser. No. 13/460,792, titled "Dosimetrically Customizable Brachytherapy Carriers And Methods Thereof In The Treatment Of Tumors," and U.S. patent application Ser. No. 14/216,723, titled "Dosimetrically Customizable Brachytherapy Carriers And Methods Thereof In The Treatment Of Tumors."

Implant (also referred to as a "physical implant"): A device that is placed in or on the patient (e.g., human or animal) for the purpose of treating the patient. Implants may emit various types of energy or chemical agents. For example, implants may contain radioactive material that emits radiation for the purpose of treating tumors. In another example, implants may emit chemicals, such as chemotherapeutic agents used to treat cancer or other agents used, for example, to promote soft tissue or bone healing or regeneration. For ease of description, examples of the planning and placement system discussed herein are primarily discussed with reference to implants comprising a carrier that contains one or more radioactive seeds. However, any other implants are compatible with the systems and methods discussed herein.

Planning image: An image of the anatomy, such as a treatment surface, that is viewed by the user to plan therapy through the placement of virtual implants on the planning image. A planning image may be a single image or a set of images that describe the anatomy from various views or in 3D, for example a series of MRI or CT scans through the anatomy of interest.

Treatment plan (also referred to herein as a "plan"): Indications of treatment to be provided to a patient, such as might be developed by the implant planning system. As discussed in further detail below, a radiation treatment plan may be developed based on one or more planning images and a technician (e.g., a radiologist, oncologist, dosimetrist, etc.) using the planning system to determine the appropriate locations and characteristics of virtual implants (and/or the implant planning system automatically determining locations and characteristics of implants based on a provided dosage prescription, for example) based on interactions with virtual implants. In some embodiments, a radiation oncologist may define a patient's critical organs and tumor (or other treatment area) and a dosimetrist may provide target doses and importance factors for each. With these planning inputs, the implant planning system may execute and, in cooperation with inputs from the user in some embodiments, develop a treatment plan which best matches all the input criteria.

Virtual Implant: A user interface element representing a physical implant that can be placed by the user of the implant planning system into an implant planning user interface to see the expected dose to tissue that will result from the corresponding physical implants. Using the implant planning system described herein, the user may add, modify, remove, and move virtual implants utilizing the planning system user interface displayed on a computing device and in close to real time (or real time) see the resulting dosage changes to the anatomy (e.g., the treatment area and/or surrounding area depicting in the planning image), allowing the user to interactively plan the types, strengths, configuration, and/or locations of virtual implants in a simulation before generating a treatment plan for use in placing the actual physical implants in a patient.

Calculated Dose: An amount of radiation or chemicals that will reach the tissues as a result of the placement of physical implants. For example, in the case of radiation implants, the (calculated) dose to tissue may be calculated using equations that account for the strength of each implant, its distance from the position for which the dose is calculated, and the intervening tissues, where the dose calculation may account for distance, radiation scatter, radiation absorption, and/or any other relevant factor. In the case of implants that release chemical agents, the calculated dose in different locations may be calculated based on factors such as the rate of release of the agent from the implant, tissue metabolism, solubility, diffusion, tissue perfusion, and/or any other relevant factor.

Isodose curve (also referred to herein as an "isodose line"): a graphical indication, such as a line, indicating points of equal dose about a radiation source, such as a radioactive seed. Multiple isodose curves may be drawn around a radiation source at regular intervals of absorbed dose, or other intervals. In some implementations, isodose curves indicate percentages of a dose that are absorbed along the isodose curve.

Isodose plan (also referred to herein as an "isodose plot" or "isodose plan"): A graphical representation of the calculated dose(s) across an area of tissues. An isodose plan may include a group of isodose curves each associated with a different calculated dose. An isodose plan may include various patterns and/or fills between adjacent isodose curves, such as varying colors, shading, patterns, and/or other visual indicators that represent corresponding dose ranges between adjacent isodose curves. In certain examples shown in the figures, varying densities of dot patterns are used between isodose curves to represent dose ranges between the respective isodose curves. In some implementations, dosage ranges may be represented by different colors to provide a more distinct separation between isodose curves. For example, certain of the figures generally use varying pattern densities as show below that may correspond to the indicated colors in certain implementations of the planning software:

red (dense dot pattern) highest dosage range
   orange
   yellow
   green
   light blue (moderately dense dot pattern): median dosage range
   light-intermediate blue
   intermediate blue
   dark blue
   transparent or no color (least dense dot pattern): lowest dosage range Depending on the embodiment, other color values or visual indications may be used as an alternative to this color scheme in order to indicate a calculated dose or dose range.

Overview of Certain Features

In certain examples shown, the user may use the planning system to plan the number, type, and/or location of various implants in order to achieve a desired clinical result. For example, in the example of tumor treatment, the user may desire to place implants in locations that provide radiation to regions that contain or contained tumor, while minimizing radiation to normal tissues.

In certain examples shown, a graphical representation of the amount of radiation that will be delivered to the tissues (dosimetry) by the radioactive implant(s) is shown as an isodose plan, where various colors indicate various ranges of radiation delivered to the corresponding tissue. In other embodiments, similar or different graphical plots could be utilized to display, for example, various amounts of a drug that would be delivered to tissues as a result of emission of the drug from the implants.

Advantageously, the planning system allows the user to easily and intuitively add virtual implants of various types to positions in the planning image and instantly (or almost instantly) see the estimated amount of radiation that would be delivered to the corresponding tissues if that treatment plan was implemented. In addition, the user may easily move the virtual implants, for example by dragging them with a mouse cursor or with a finger on a touch screen and almost instantly see the new isodose curves that result from the new treatment plan.

In addition, the implant planning system may allow the user to select from a variety of different implant types (e.g., virtual implant types each having a corresponding physical implant type) to add to a plan, including implants that do not contain radioactive seeds, and therefore serve as physical spacers in a plan. For example, various shapes and sizes of virtual implants (e.g., so long as corresponding physical implants may be created) may be used in a treatment plan. In some embodiments, virtual implants may be moved as physics objects, such that the virtual implant simulate real world physical interactions. For example, a virtual implant that is moved towards and into a series of virtual implants may push the virtual implants apart in a similar manner as moving a domino on a tabletop would displace a series of other dominos on the tabletop. The physical attributes of implants may be modified in various implementations and/ or may be modified by a user for a particular treatment plan or even for particular implants (e.g., a virtual implant placed on a center of a tumor bed may be "glued" to that position so that it does not move based on simulated physical forces of adjacent implants, but the other implants may exhibit simulated real world physical interactions.

In addition, the implant planning system may allow the user to delete virtual implants or change the configuration of virtual implants, for example by flipping them in the case of virtual implants where the radioactive seed within a virtual implant is asymmetrically positioned with respect to the virtual implant surfaces. In this way, the user may rapidly and intuitively create a treatment plan including the number, type, and/or location of actual physical implants using virtual implants that may be adjusted and manipulated in the various manners discussed herein to achieve the desired treatment goals.

Example System Architecture

FIG. 1 illustrates one example of an implant planning system 150, which may also be referred to herein as simply the "computing device 150" or "the device 150." In this embodiment, the computing device 150 includes software modules 151, one or more processors 152, memory and storage 153, an operating system 154, a display 155, input devices 156, such as a mouse keyboard or touchscreen, interfaces 157, and optional camera 158.

A number of different technologies could be utilized to obtain planning images, for example MRI scanner 124, CT scanner 126, or a 2-D or 3-D imaging device 128, for example using 2D or 3D optical or ultrasonic imaging. In some embodiments, 3D information, for example acquired using MRI, CT, ultrasound, or optical imaging may be processed to form a 2D or 3D surface for planning, for example utilizing 3D processor 122 and techniques such as surface rendering, volume rendering, or multiplanar reconstruction (MPR).

PACS system 120 may be used to manage, store, and transmit images and other medical information, including information used by and produced by systems and methods described herein, including the planning image and the treatment plan, which may include implant types, configurations, and locations as well as dosimetry or other calculations.

Optional planning server 140 may serve a variety of optional functions in various embodiments. For example, the planning server 140 may store prior dosimetry or other treatment information that a patient has received which may be made available to the user of the system, as prior therapy in various spatial locations may influence the planning of additional therapy to be delivered by implants. In some embodiments, the planning server 140 may perform dose calculations, rather than performing the calculations on computing device 150. The planning server may store information regarding various types, configurations, and strengths of implants available for use, which may be represented as virtual implants in the planning system UI during the treatment planning process.

In some embodiments, the planning system described herein may transmit a treatment plan, or a portion of a treatment plan, to an ordering system 142 so that the physical implants included in the treatment plan can be created and shipped to the user in advance of the operation in which they are to be implanted. For example, some radioactive implants emit radiation over a relatively short period of time and need to be ordered from a supplier in advance of the surgery where they are to be implanted. Using systems and methods described herein, a user may create a plan in advance of surgery, for example using a planning image obtained preoperatively, for example using MRI, and the number and type of implants used in the plan may be transmitted to Ordering System 142, instructing the company that produces the implants to deliver the needed implants to the user in advance of surgery.

For example, in one embodiment the planning system may generate an email (or other data package, such as a comma separate values (CSV) file or text file) including physical implant information (based on the final virtual implants of a treatment plan) and automatically (or after user review in some embodiments) transmit the information via email to an ordering system. As an example, the data package (e.g., body of an email to the ordering system) may include information in a format such as below, which indicates the physical implant shape (e.g., "TILE"), strength (e.g., maximum radiation emitted from the radioactive seed), and the planned anatomical position of the physical tile at the treatment area (e.g., in x, y, z coordinate with reference to an absolute position, such as a lower left corner of the planning image):

9 sources
[1] TILE strength=3.7 at (6.443, 5.100, 0.300)
[2] TILE strength=3.7 at (4.823, 7.242, 0.300)
[3] TILE strength=3.7 at (6.286, 7.300, 0.300)
[4] TILE strength=3.7 at (7.486, 6.314, 0.300)
[5] TILE strength=3.7 at (5.529, 5.971, 0.300)
[6] TILE strength=3.7 at (3.943, 5.329, 0.300)
[7] TILE strength=3.7 at (3.514, 6.414, 0.300)
[8] TILE strength=3.7 at (3.992, 7.858, 0.300)
[9] TILE strength=3.7 at (7.614, 7.971, 0.300)

The data package may also include an image of the treatment plan, such as a screen shot or image export of the display frame 410 (or the entire user interface 400). As noted elsewhere, the data package sent to an ordering system may include various other information in various formats and the information may be transmitted using methods other than email, for example via a secure web service.

As described further below with reference to the implant placement guide system, that system may guide the user, for example the surgeon, in placing physical implants in or on the patient's body, based on a developed treatment plan. In one embodiment described below, information from the plan may be projected on to the patient's body, for example using Projection System 160.

In some embodiments, a real time image of the anatomy (e.g., the treatment surface of the patient) may be acquired, for example, using Camera 158 and/or 2D or 3D imager 128, and the treatment plan (e.g., locations, types and/or configurations of the virtual implants) are graphically superimposed on this real time image to guide the surgeon in placing actual implants in the locations of the virtual implants in the plan.

Example Planning and Placement System(s)

Figure 2:
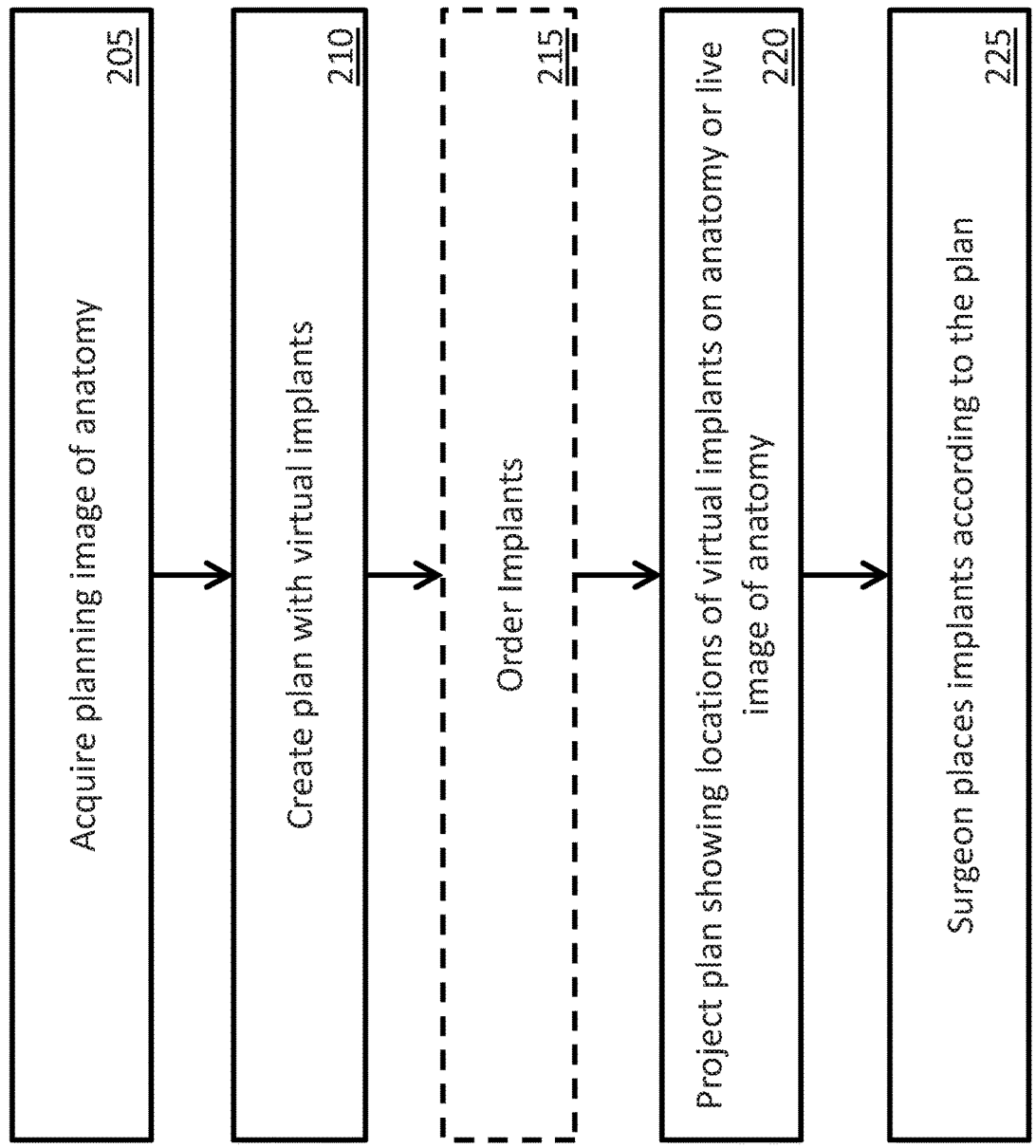
FIG. 2 is a flowchart illustrating one embodiment of a method of planning placement of implants and guiding placement of the implants.

In one embodiment, development of a treatment plan using virtual implants and guiding of surgical implant placement based on the treatment plan may be performed by the computing device 150. In other embodiments, separate computing devices, such as an implant planning system and an implant placement guide system, respectively, control the processes of developing treatment plans (e.g., a radiation oncologist or other doctor at a remote location to a hospital may perform the planning) and guiding the surgeon in placing the implants according to the plan. Additionally, as noted above, in some embodiments the implant planning process may be performed entirely independent of the actual surgical implant process, such that other surgical implant guide methods may be used in order to implement a treatment plan developed using the implant planning system discussed herein. Similarly, an implant treatment plan developed using other methods (e.g., manually or using other software applications) may be used by the implant placement guide system in order to guide a surgeon in implementing the developed plan. The implant planning system, implant placement guide system, and/or other systems and computing devices discussed herein may each include some or all of the same or similar components discussed with reference to device 150 of FIG. 1. Depending on the embodiment, the method of FIG. 2 may include fewer or additional blocks and/or the blocks may be performed in an order different than is illustrated.

Figure 3:
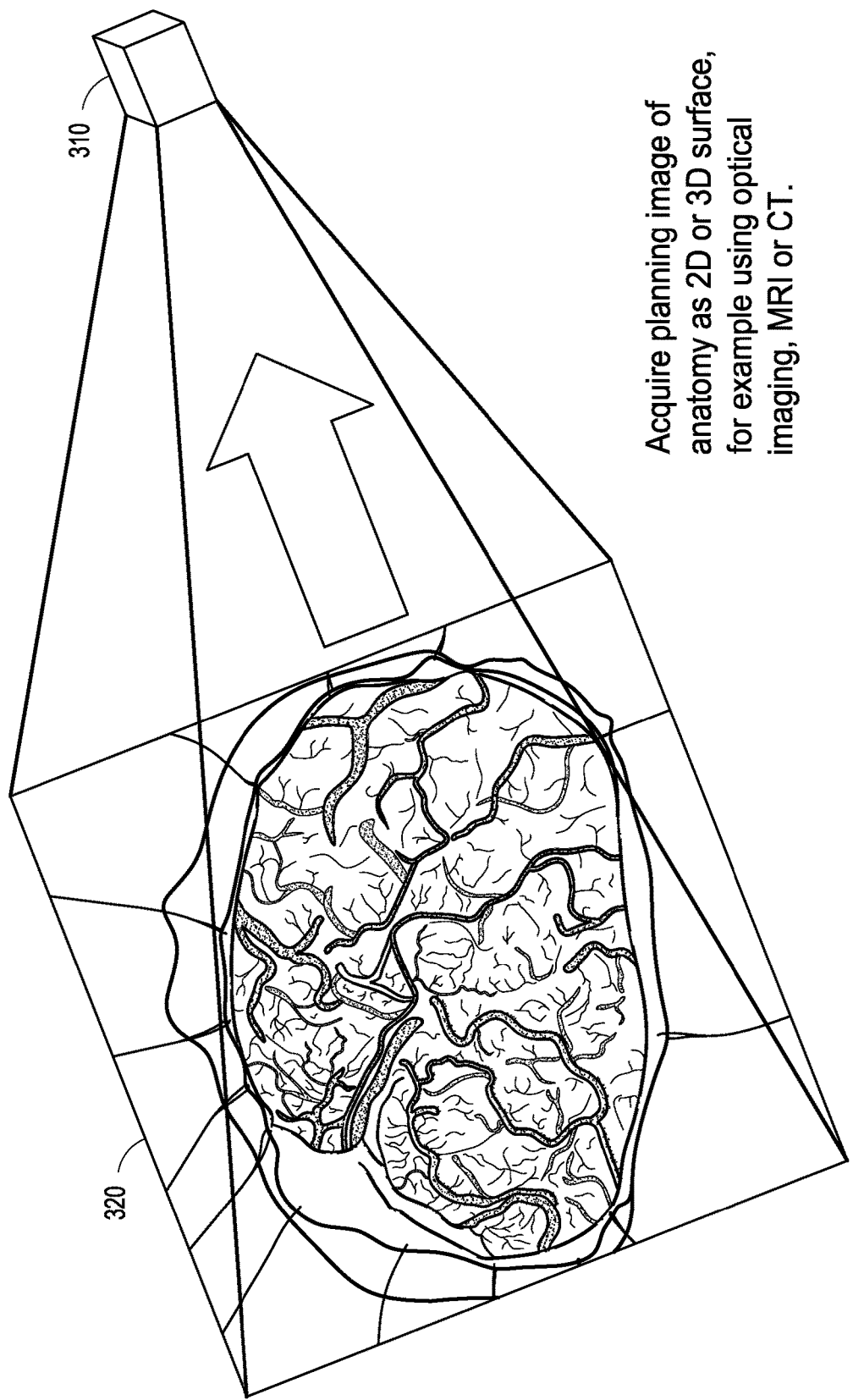
FIG. 3 shows an example of an imaging device 310 acquiring a digital image of the anatomy that will be used as a planning image.

Beginning at block 205, a planning image (or images) is acquired. FIG. 3 illustrates a conceptual diagram of an imaging system 310 (e.g., any of those devices discussed herein that may obtain a planning image) acquiring a planning image of anatomy 320. The planning image may be a two dimensional image, for example obtained with a digital camera, or may be a 3D image or 3D surface, for example a 3D surface obtained using data acquired by various modalities such as magnetic resonance imaging, computed tomography, ultrasound, or 3D optical imaging. Examples of structures from which 3D planning images may be acquired include surgical cavities, the internal surface of a bronchus or portion of the gastrointestinal tract, the brain, the skin, and perineum.

Planning images may be obtained preoperatively, for example using techniques such as magnetic resonance imaging (MRI), computed tomography (CT), photography or endoscopy, or planning images may be obtained at the time of surgery, for example using digital photography, 3D optical imaging, ultrasonography, or intraoperative MRI or CT.

Moving to block 210, a treatment plan is created utilizing the implant planning system and virtual implants, as will be described in more detail below, such as with reference to FIGS. 4A-6A.

In block 215, physical implants may be optionally ordered based on the treatment plan created in block 210. This may be done in an automated fashion, for example via transmission of the configuration, number, type, and strengths of the implants within the treatment plan. In some cases, physical implants or implant components may have long lives and a stock of implants may be available to the user. In other cases, physical implants or implant components (e.g., the carrier material, such as collagen, and/or the radioactive component, such as a seed) may have short lives, and need to be ordered in a short timeframe prior to implementation. In particular, a physical implant with a long life may comprise components having a useable time period of greater than 3 months (or some other time, such as 1 month, 6 months, a year, etc.). For example, an expiration date, or date by which it is best to use a manufactured physical implant, may indicate a useful life of the physical implant. Physical implants with short lives may have expiration dates, best used by dates, or shelf life periods, that encourage use of such physical implants within a shorter timeframe from manufacturing of the physical implant, such as in less than 1 week (or some other time, such as 1 day, 3 days, 2 weeks, 1 month, etc.).

In some embodiments, the physical implants may be ordered based on an estimate of what the treatment plan will consist of, and then a plan may be created after the implants have arrived. In one embodiment, where the plan is developed immediately prior to implantation, the planning software may display to the user an inventory of available physical implants that are available for use in the plan (e.g., inventory that is on-site or available in a necessary time frame in order to complete the surgery).

In block 220, the plan is implemented using the implant placement guide system, such as by displaying the locations, types, strengths, and/or configuration of physical implants simultaneously with imaging of the anatomy at the time of implantation to guide the surgeon, or other user, in placing the implants, as will be describe below.

In block 225, the surgeon, other user, and/or an automated (e.g., robotic) placement system, places the physical implants according to the plan and using guidance from the implant placement guide system.

Example Planning System Operations

Figure 4A:
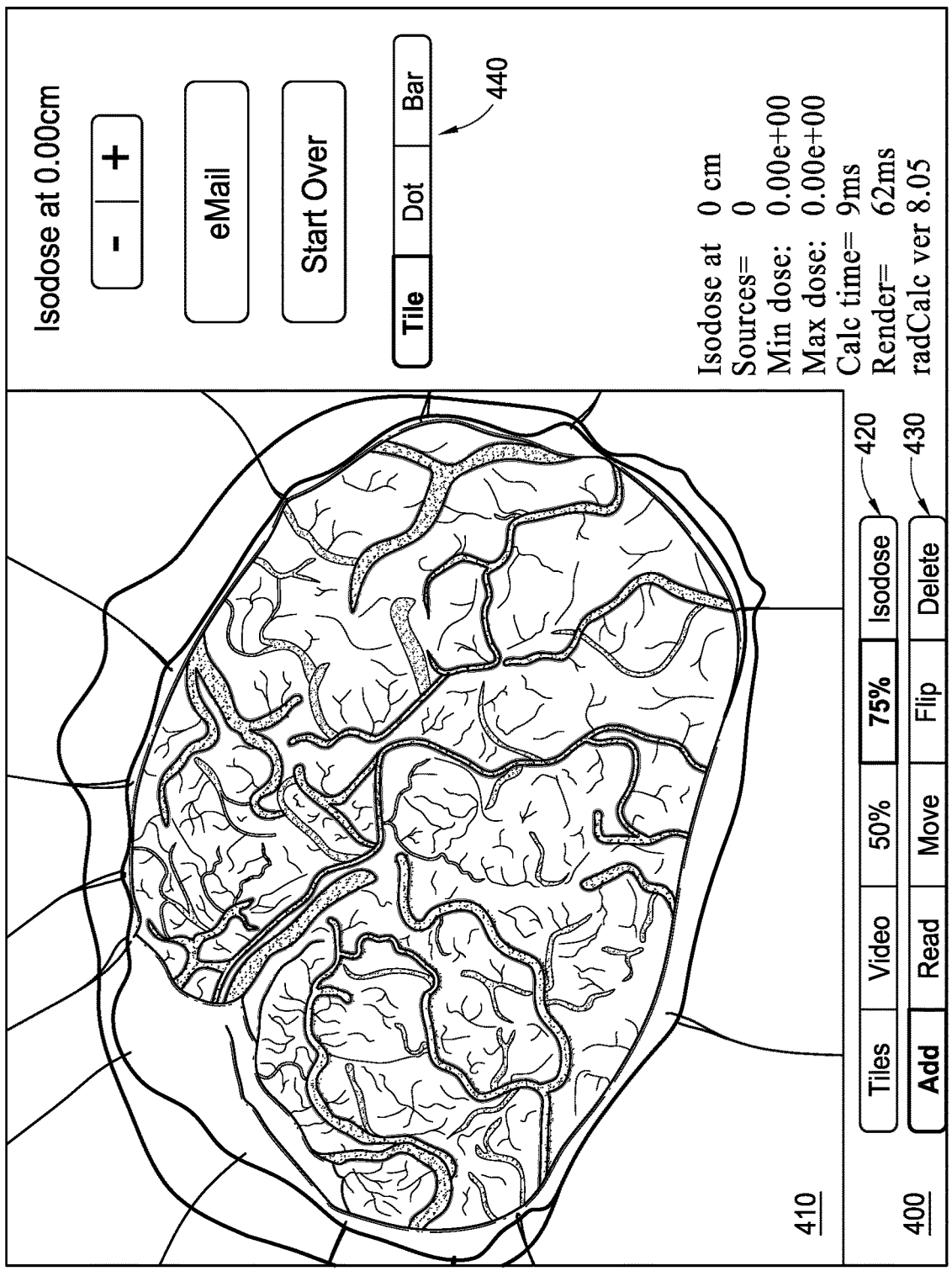
FIG. 4A illustrates an example of a graphical user interface 400 that may be generated by the implant planning system, such as may be implemented on the computing device 150.

FIG. 4A illustrates an example planning system user interface 400 that may be generated by an implant planning system in some embodiments. The user interface 400 may be partially or entirely generated on a server device, for example, and viewable on a user device such as via a thin client connection, in some embodiments. In other embodiments, the user interface 400 may be partially or entirely generated on the user computing device, such as a radiologist, oncologist, surgeon, and/or other computing devices. In some embodiments, the user interface 400 includes sharing functionality that allows multiple users to concurrently create a treatment plan, such as by allowing an oncologist and surgeon to concurrently view the user interface, and a dynamically updated treatment plan including virtual implants, in order to interactively develop an appropriate treatment plan for a patient. Thus, the computer device(s) that generate, process, and/or update information received from one or more users in the planning system user interface may vary from one implementation to another, and all such variations are within the scope of this specification. For ease of illustration, the planning software is primarily discussed herein as being generated by an implant planning system.

Certain interactions and operations performed with reference to planning software are described below with regard to inputs provided via a touch screen, where the user may touch a finger (or fingers, stylus, or other physical implement) to a position on the touch screen to provide input. In other embodiments, the user inputs may be received from any other suitable input device, such as a cursor/mouse, keyboard, a 3D input system such as a Leap motion controller, or voice control, for example.

In the example of FIG. 4A, the user interface 400 includes a display frame 410 which displays an example planning image, such as an image acquired using the imaging device 310 of FIG. 3, on which the user may place virtual implants.

Figure 4B:
FIGS. 4B-4D show various stages of development a treatment plan using the planning system software and planning software user interface.
Figure 4C:
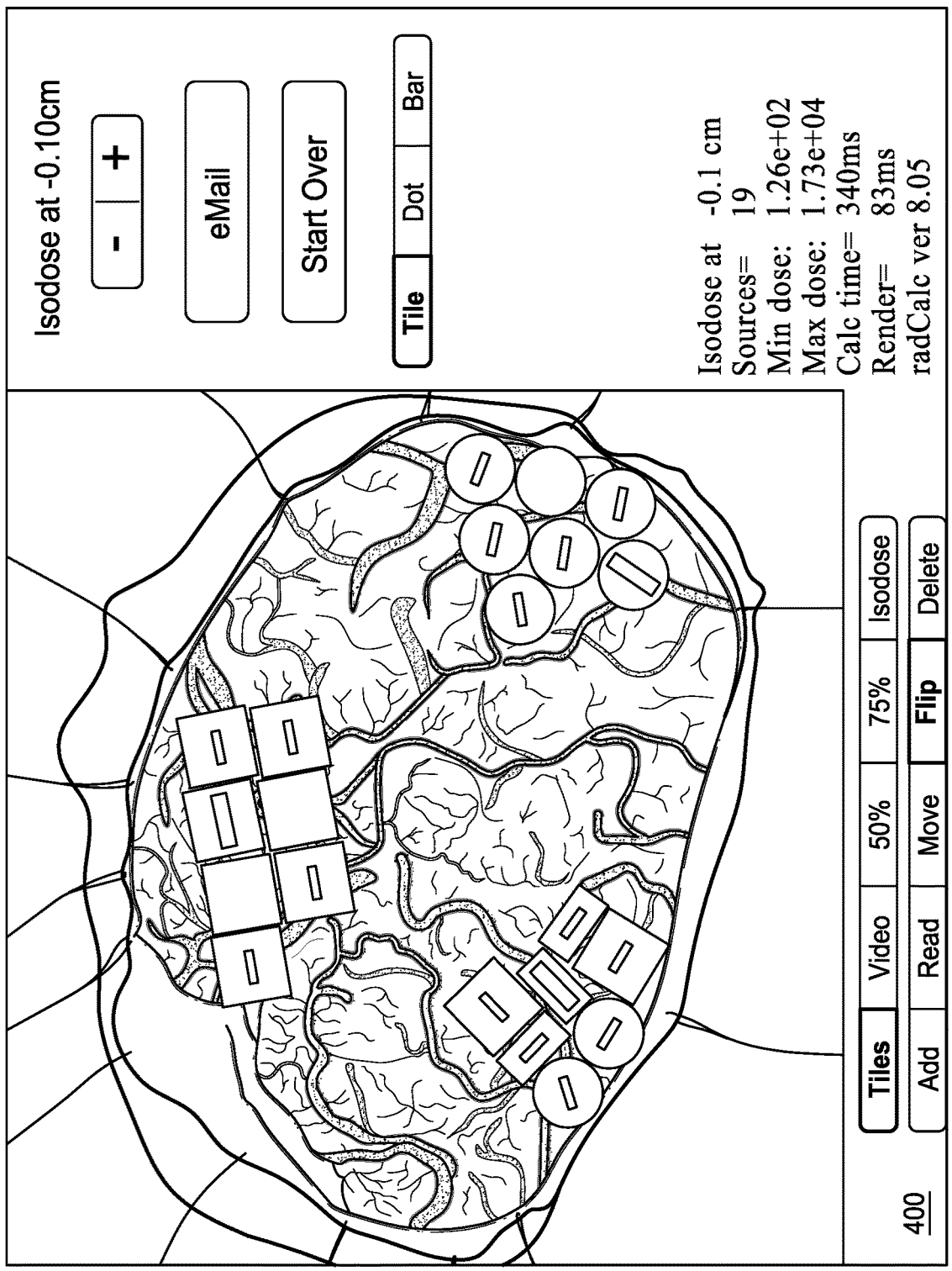
Figure 4D:
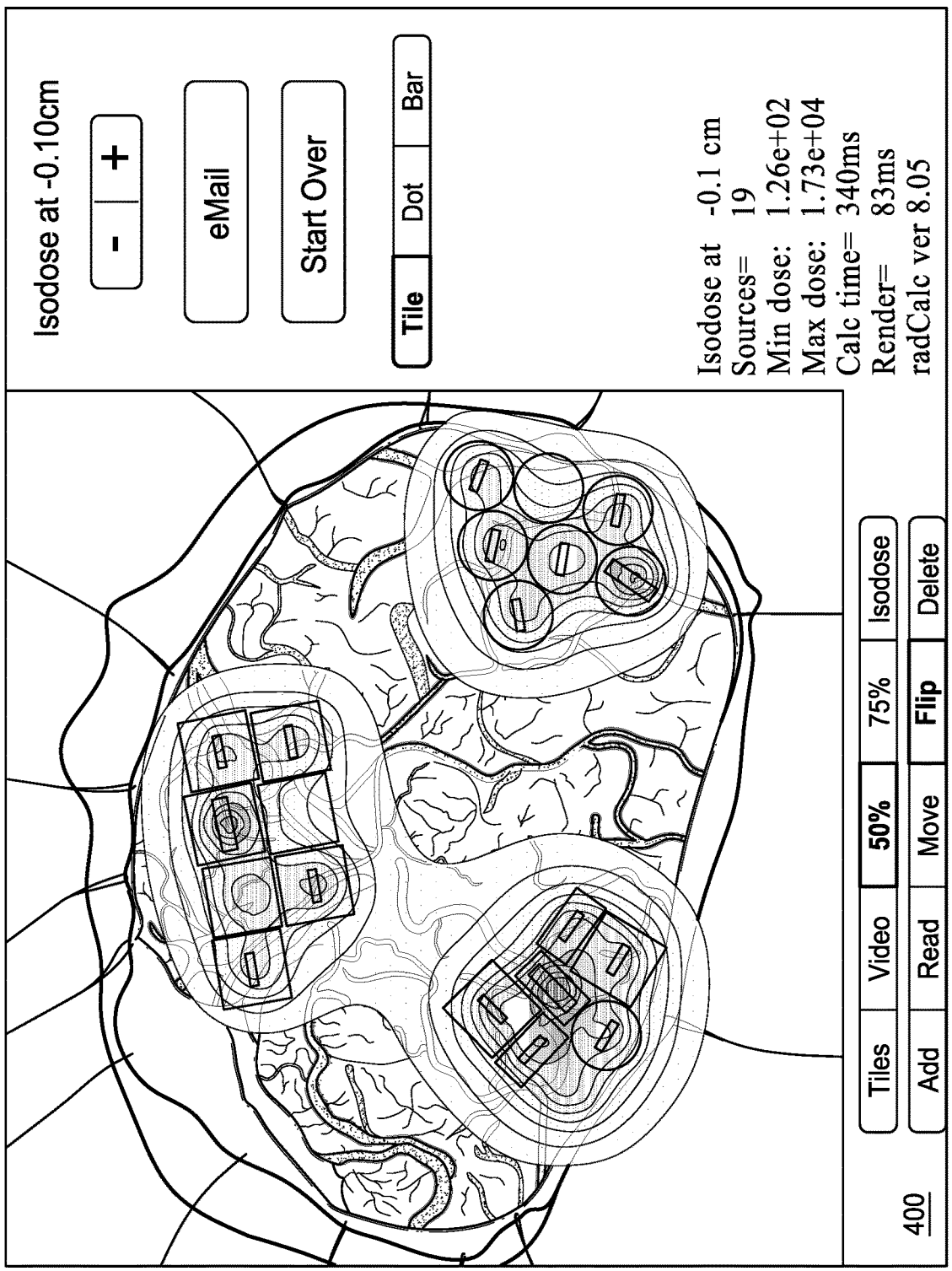

FIGS. 4B-4D illustrate respective bars of buttons 420, 430, and 440. In this implementation, each of the bars of buttons includes multiple buttons configured such that the buttons within a particular bar act as radio buttons where only a single button may be selected at a time and selection of a button automatically deselects other buttons in the same bar of buttons. In other embodiments, other types or arrangement of buttons may be used to accomplish the various functions described below. Similarly, other user interface controls may be used in other embodiments, such as sliders, check boxes, pull down menus, etc.

FIG. 4B displays button bar 420 from user interface 400 that may be used to select various ways that information may be displayed in display frame 410. In this example, options for display include the following:

- Tiles: Display the virtual implants placed by the user superimposed on or otherwise simultaneously with the planning image, for example as illustrated in FIG. 4C. In one embodiment, with the virtual tiles depicted in the display frame, subsequent selection of the Tiles button removes the virtual tiles from the display frame, such that display of the tiles may be toggled with this button. In the example of FIG. 4C, the user has selected the "Tiles" button to simultaneously display the planning image and virtual implants (the plan). In this example, the virtual implants are displayed as opaque so that the underlying planning image may be simultaneously visualized. In various embodiments, the virtual implants may be graphically positioned on top of or beneath the planning images. One, both or neither of the planning image and virtual implants may be displayed as semitransparent in other embodiments and/or in response to user input selecting an opacity level.
- Video: Display the virtual implants placed by the user superimposed on or otherwise simultaneously with a live image of the anatomy (e.g., the treatment surface), for example as described with reference to FIG. 10.
- 50%: Display the virtual implants and associated calculated isodose plan with 50% transparency, superimposed on the planning image, as in the example of FIG. 4D.
- 75%: Display the virtual implants and associated calculated isodose plan with 75% opacity, superimposed on the planning image, as in the example of FIG. 4E. In other embodiments, other transparency levels may be included in a similar user interface control. Similarly, in one embodiment the user may customize the transparency levels that are available and/or select a custom transparency level through a different user interface control, such as a slider that incrementally adjusts the transparency. In some embodiments, transparency of the virtual implants may be selectable, rather than opacity. For example, an opacity of 25% may be set in order to achieve a similar effect as setting transparency to 75%.
- Isodose: Displays the calculated isodose plan superimposed on the planning image, as in the example of FIG. 4F. In this embodiment, the isodose plan is displayed with no transparency and without display of the Tiles. In other embodiments, transparency level of the isodose plan and/or tiles may by adjusted to any levels to depict various combination of those display elements. The calculated isodose lines may be automatically determined by the planning system, or selected by a user, as predetermined values (e.g., an isodose line at each x cGy from zero to a maximum calculated dosage (at any point in the treatment plan) or to provide a particular quantity of y isodose lines across a particular range, such as y isodose lines at even intervals between zero and a maximum calculated dosage. In other embodiments, values associated with isodose lines may be determined in other manners, such as percentages relative to a dose point maximum.

Figure 4E:
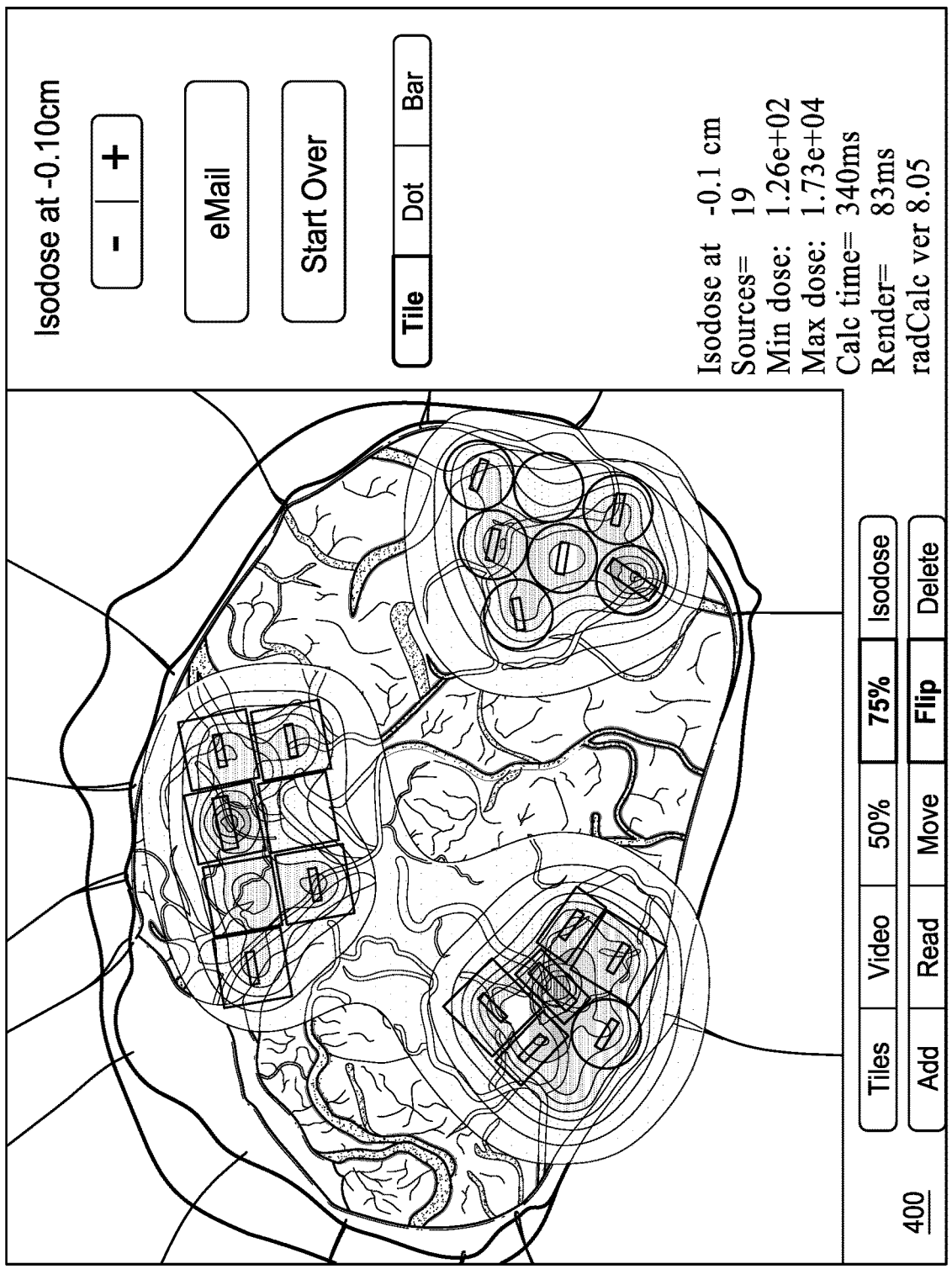
FIG. 4E is similar to FIG. 4D, but the user has pressed the "75%" button to cause the system to display the isodose plan and virtual implants with 75% opacity.
Figure 4F:
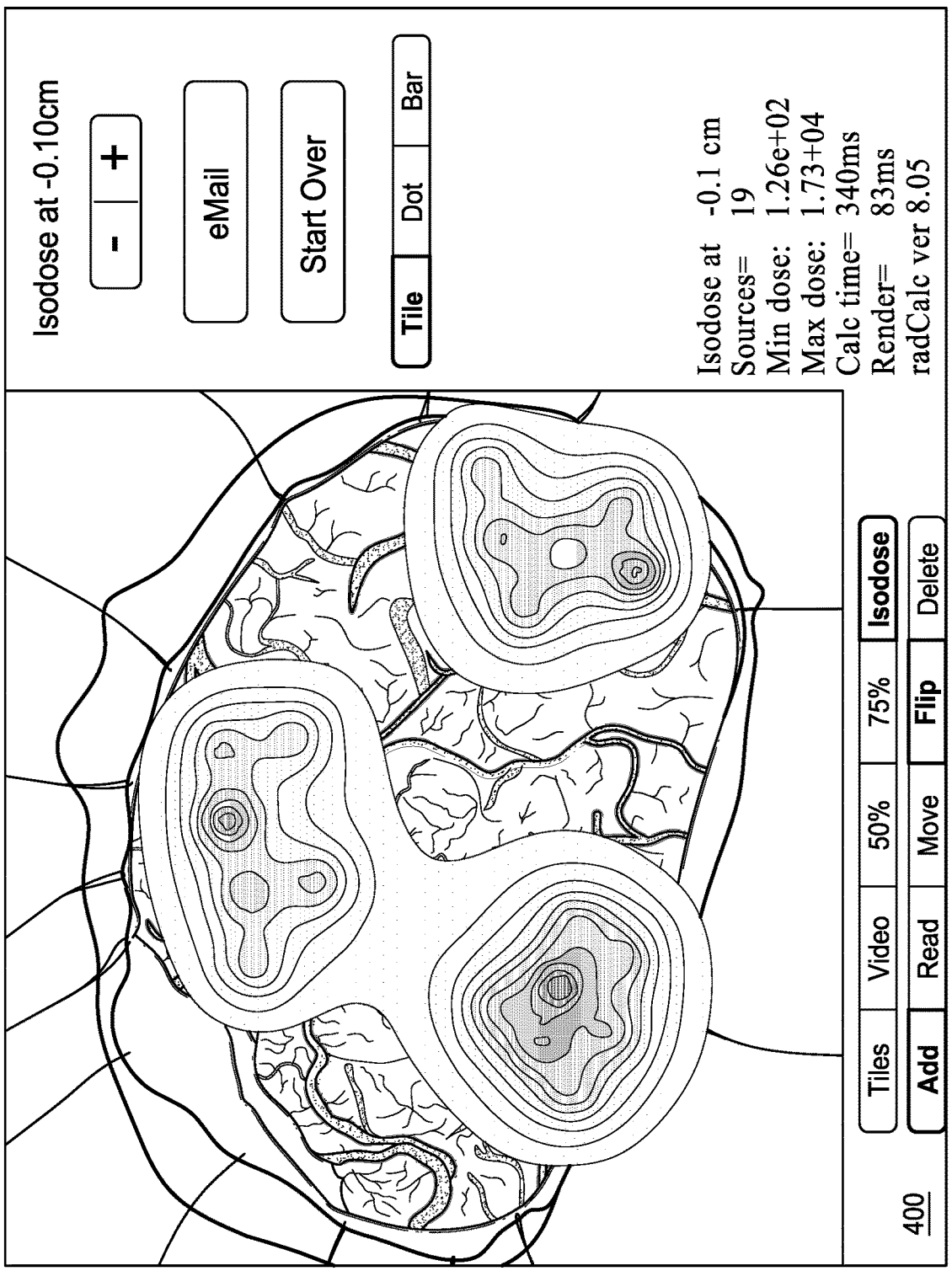
FIG. 4F is similar to FIG. 4E but the user has pressed the "Isodose" button, to cause display of the isodose plan without transparency and without display of the virtual implants.

With reference to FIG. 4D, an isodose plan for the current combination and placement of implants is displayed at a 50% transparency atop the planning image. Thus, the isodose plan is displayed in a semitransparent manner so the user may simultaneously visualize the isodose plan, the virtual implants, and the underlying planning image. With reference to FIG. 4E, the user has pressed the "75%" button to cause the system to display the isodose plan and virtual implants with 75% opacity, and in the example of FIG. 4F, the user has pressed the "Isodose" button to cause the isodose plan to be displayed at 0% transparency (or 100% opacity). In various embodiments, the isodose plan, implants, and planning image may be shown with various degrees of transparency and in various combinations, and the various graphics may be ordered in different ways.

Example Algorithms for Isodose Curve Calculations

In some embodiments, the dosimetry algorithm used to generate isodose curves comprises calculating the radiation dose at each 3D position in a plane or curved surface that is z cm from the z position of the planning image. In this embodiment, the dose at each point is the sum of the dose from each implant, where the radiation from each implant is proportional to the strength of the radiation source for the implant divided by the distance from the implant to the point squared, times an equation that accounts for absorption of radiation and radiation scatter by intervening and adjacent tissue. The displayed graphic is in the form of an isodose plan including multiple isodose curves, where fill patterns between adjacent isodose curves (which may be replaced by corresponding colors or other graphical indicia in other embodiments) represents a different range of radiation delivered.

In another embodiment, implants could emit therapeutic agents and/or a catalyst that invokes or enhances therapeutic activity of another therapeutic agent or the tissue itself, other than radiation, such as chemotherapeutic agents, and other types of calculations could be utilized to show the user the expected delivery of the agent to the tissue. As with radiation implants, the user can use an interface system such as this to decide on the type, configuration, strength, and locations of chemical emitting implants to achieve the desired therapeutic effect, while minimizing the effect on adjacent normal tissue. Additionally, in some embodiments, the planning system may be configured to calculate an isodose plan for radiation treatment in conjunction with a therapeutic plan (that might look similar to the isodose plans discussed herein) indicating expected therapeutic level of other agents delivered to a treatment area, such as by therapeutic virtual implants, and display such plans in combination in order to allow planning of multiple modalities of treating a tumor site (or other site).

In some embodiments, the implant planning system provides an inverse planning component wherein the computer system automatically determines a treatment plan comprising multiple virtual implants. Such a treatment plan may be generated based on a provided prescribed dosage and a treatment area indicated on the planning image, such as by automatically determining a combination of virtual implants that best delivers the prescribed dosage to the treatment area. The planning system may automatically generate the treatment plan based on one or more user selected parameters that impact which virtual carriers are selected to achieve the prescribed dosage. For example, the parameters may allow the user to provide a desired balance between sparing of nearby tissue and delivering the prescribed dosage in a uniform manner. Additionally, the planning software and/or a user may indicate areas of tissue (either on the treatment surface or below the treatment surface) to which radiation should be avoided as much as possible (e.g. organs that are very sensitive to radiation) and/or other areas that are not as critical to spare radioactive damage. Thus, based on such factors, the implant planning system could generate different configurations, such as sizes, orientations, positions, etc., of virtual implants for a particular prescribed dosage and treatment area to achieve different treatment priorities (e.g., as indicated in the parameters). In some embodiments, the implant planning system may initially provide a treatment plan using the inverse planning component, or may provide multiple treatment plans using variations of treatment priorities/parameters for each developed treatment plan, and allow the user to further manipulate the treatment plan, if needed, using the systems and methods described below.

Virtual Implant Manipulation

Figure 5A:
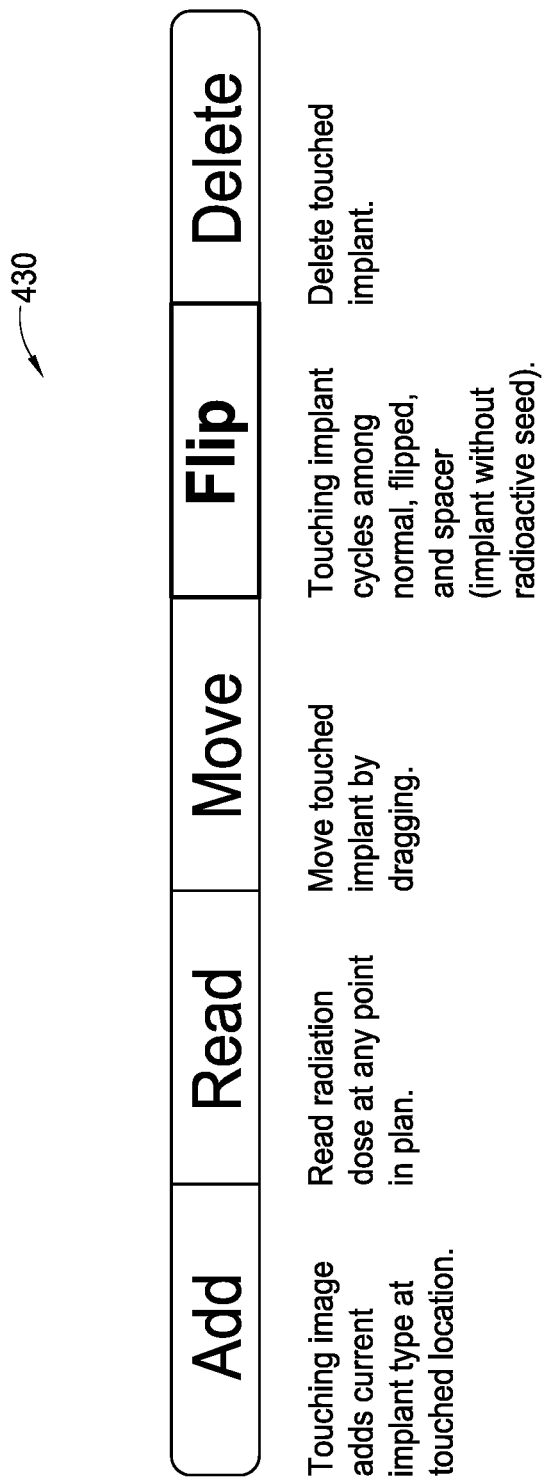
FIGS. 5A-5C illustrates additional interface elements that may be included in certain user interfaces generated by the implant planning system.

FIG. 5A displays button bar 430 from user interface 400 (FIG. 4A) that may be used to select various operations that will occur when the user interacts with a planning image displayed in display frame 410 and/or a virtual implant displayed in display frame 410.

Add: Adds a virtual implant of the currently selected implant type, as described with reference to FIG. 5B, at the position the user indicates on the planning image using, such as by tapping a location on the planning image using a touch screen or clicking a mouse with the cursor positioned on the planning image.

Read: Displays an arrow or other indicator at the position the user touches and displays the calculated dose at that 3D location, with the z position (depth) of the location displayed in the upper right region of the GUI. In some embodiments, the calculated dose may be displayed as a relative dose (e.g., a percentage of a maximum dosage calculated for any location within the patient anatomy) and/or an absolute dose (e.g., the absolute cGy at the selected 3D location).

Move: When this operation is active, the user may touch and drag a virtual implant as if it were a real object. Virtual objects act as physical objects in the user interface in that they interact with each other so that a virtual object that collides with others will push those other virtual objects.

Flip: Implant types may have a variety of states, e.g., default, flipped, and empty (a spacer), as described with reference to FIG. 5B. When Flip is selected, touching an implant causes it to change to its next state and recycles to the default state once the last available state is reached, e.g., a virtual implant may cycle through default, flipped, spacer, and then back to default when a virtual implant is touched or otherwise selected and the "Flip" mode is active.

Delete: When this operation is active, touching a virtual implant causes it to be deleted.

Figure 5B:
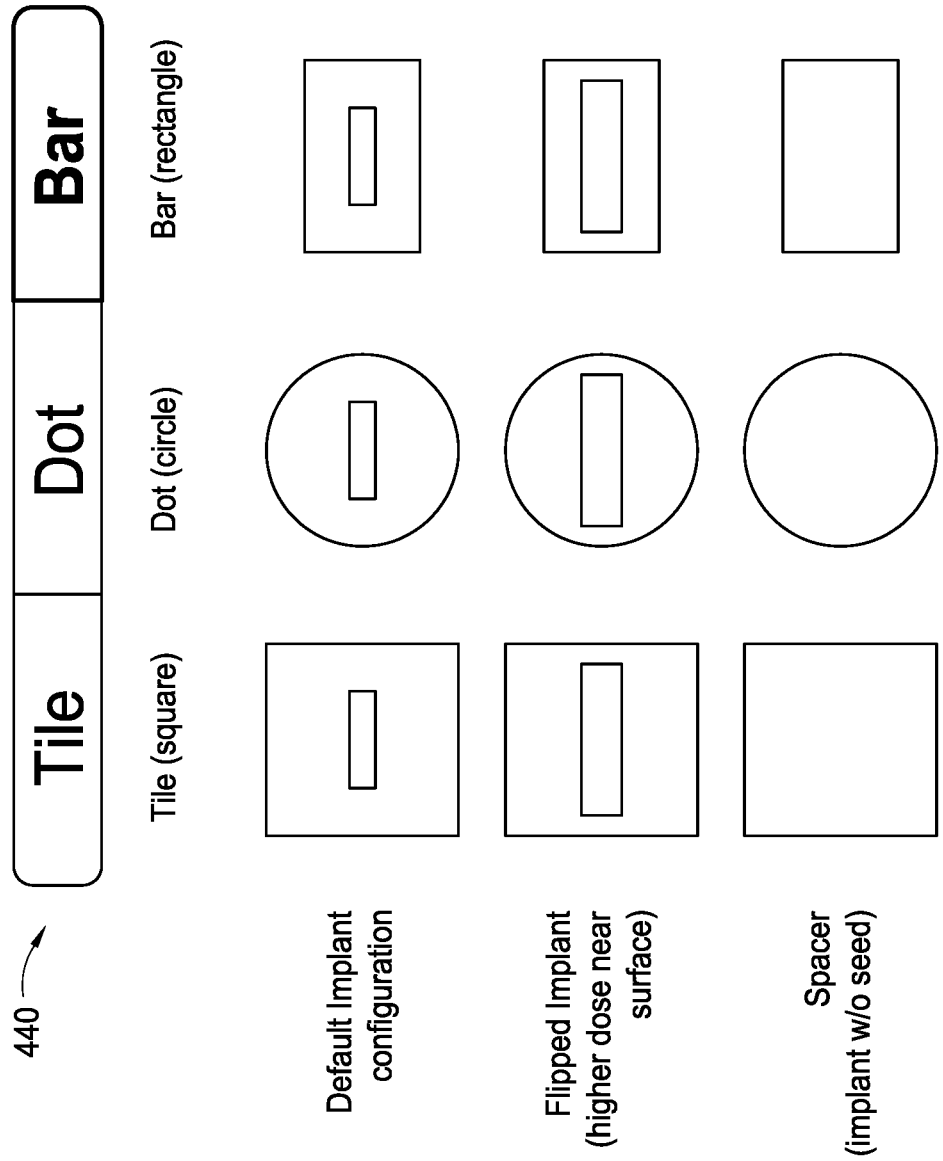

FIG. 5B illustrates button bar 440 showing types of implants available in the example interface 400. Implants may have various configurations, and three configurations (tile, dot, and bar) are shown for each implant in a column below the respective tile, dot, and bar buttons on button bar 442, along with example graphic representations of each implant in each of its configurations. In other embodiments more or fewer implants may be available, with various other configurations. In some embodiments, additional user interface controls may be available to allow further customization of virtual carriers that are included in the treatment plan. For example, a control that customizes seed strength for a carrier may be included in some embodiments of the planning user interface. In one embodiment, such a control may be implements as a pop-up slider that appears when a seed shape (e.g., tile or dot) is selected, wherein the slider includes a selector that is movable between a range of seed strengths that area available (and/or creatable). Thus, the user may customize each seed, if desired, using such controls, and/or may use a default seed strength by releasing the seed shape button (e.g., the tile or dot button) rather than sliding to a particular seed strength after touching the button. In other embodiments, any other characteristic of carriers may be selected in a similar manner.

In the example shown, the default configuration of each implant contains a radioactive seed that is positioned 4 mm superior to its inferior service (not illustrated in this top view schematic). This is indicated by the virtual implants in the first row of example graphic representations in FIG. 5B, labeled as "default implant configuration." A rectangle in the center of each virtual implant represents a radioactive seed within these virtual implants.

In the example shown, implants also have a "flipped" configuration, the second row example graphical representation in FIG. 5B, labeled as "flipped implant," in which the radioactive seed is positioned 2 mm above its inferior surface (in the particular example virtual implant discussed herein; other placements of seeds within carriers is expected and are similarly usable in default and flipped formations). As the virtual implants are placed on the virtual anatomic surface, this configuration places the radioactive seeds closer to the anatomy, and therefore they deliver a higher dose, as indicated by the larger rectangle graphic representing seeds in the virtual implants.

Implants may also have an "empty" configuration, as indicated in the third row, where each implant has no internal seed. The virtual implants may act as spacers in this configuration, and indicate the position of a physical spacer in a treatment plan.

Figure 5C:
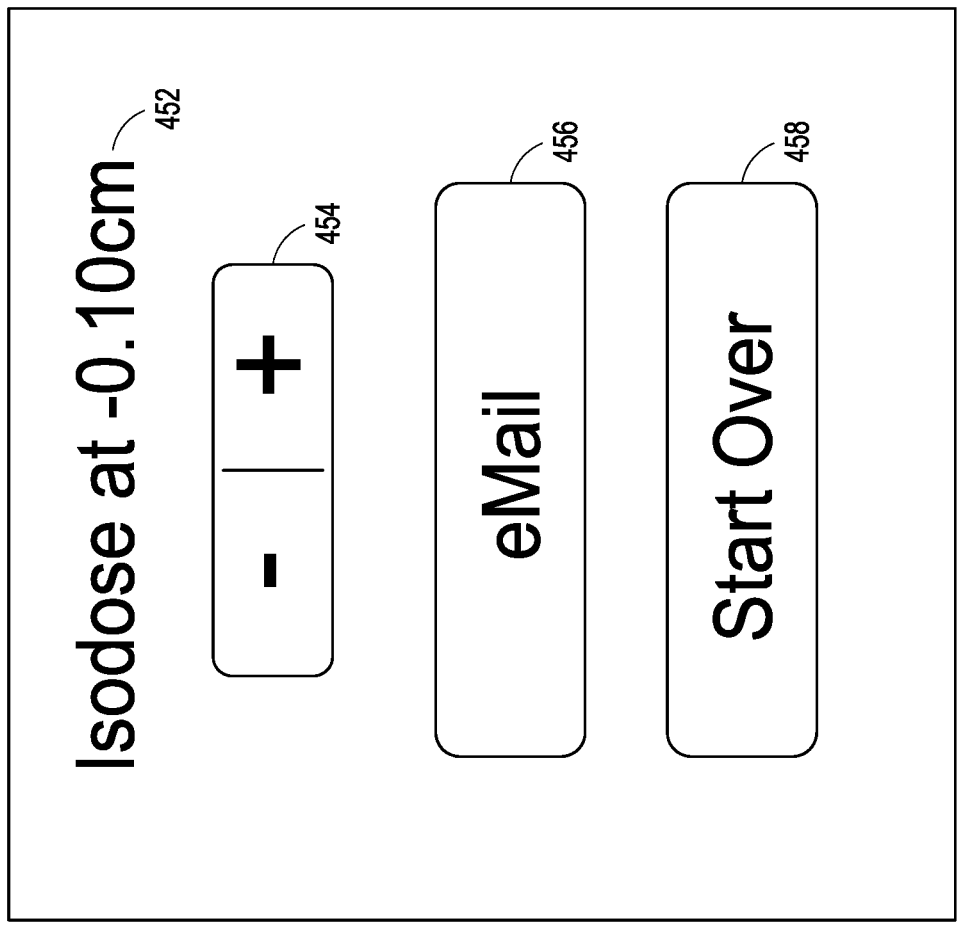

Any other configuration, spacing, offset of seeds within implants, etc., may be used in conjunction with implant planning system discussed herein. FIG. 5C illustrates additional interface elements that may be included in certain user interfaces generated by the implant planning system, such as the interface 400 of FIG. 4A. In this example, isodose depth 452 indicates the z position, or depth relative to the treatment surface within the planning image, at which the dose is calculated for isodose curves and read function (for a particular three dimensional location within or outside of the patient anatomy). In the example of FIG. 5C, the z position is −0.10 cm relative to the treatment surface, where a negative position indicates a position that is inferior to the treatment surface.

In one embodiment, when the planning image is a plane, the dose calculation is also a plane positioned at the indicated z position. However, when the planning image is a 3D image associated with a 3D treatment surface and/or 3d treatment area, the isodose depth indicates a depth with reference to the actual treatment surface locations. Thus, the isodose depth relative to a top surface of a 3D volume, for example, may vary as the depth of the treatment surface varies.

In other embodiments, other geometries may be used to determine the locations that a dose is calculated at a z distance from a 3D surface. For example, in another embodiment where the planning image is a 3D surface, each dose calculation (and the resulting isodose curves) may be calculated at a 3D point that is z cm from the treatment surface along a vector that is normal (perpendicular) to the 3D surface at the point of interest. In another embodiment, dose calculations (and resulting isodose curve calculations) may be performed along flat planes, for example where the orientation and position of the plane at z=0 is chosen by the user or automatically chosen by the system as a best fit to the 3D curved surface.

In this example, button 454 allows the z position to be adjusted. For example, pressing the "+" may increase the z position by 0.1 cm and pressing the "−" may decrease the z position by 0.1 cm. In one embodiment, the z position may be graphically represented in the display frame, for example by varying the appearance of the displayed isodose plan, for example by changing the depth of a shadow arising from the isodose curves or by varying the transparency of the isodose fills as a function of z depth. In other embodiments, other types of user interface controls may be used to change the z position, such as a slider bar.

In this example, an "eMail" button 456 may be used to transit information about the currently displayed treatment plan to other systems or individuals. For example, in one embodiment the "eMail" button could have a different label, e.g., "Order", and communicate the needed implants to Ordering System 142, such as by transmitting part or all of the treatment plan to an implant provider.

In this example, a "Start Over" button 458 allows the user to clear the current plan and start over, such as by removing all virtual implants that are currently part of the treatment plan.

Figure 5D:
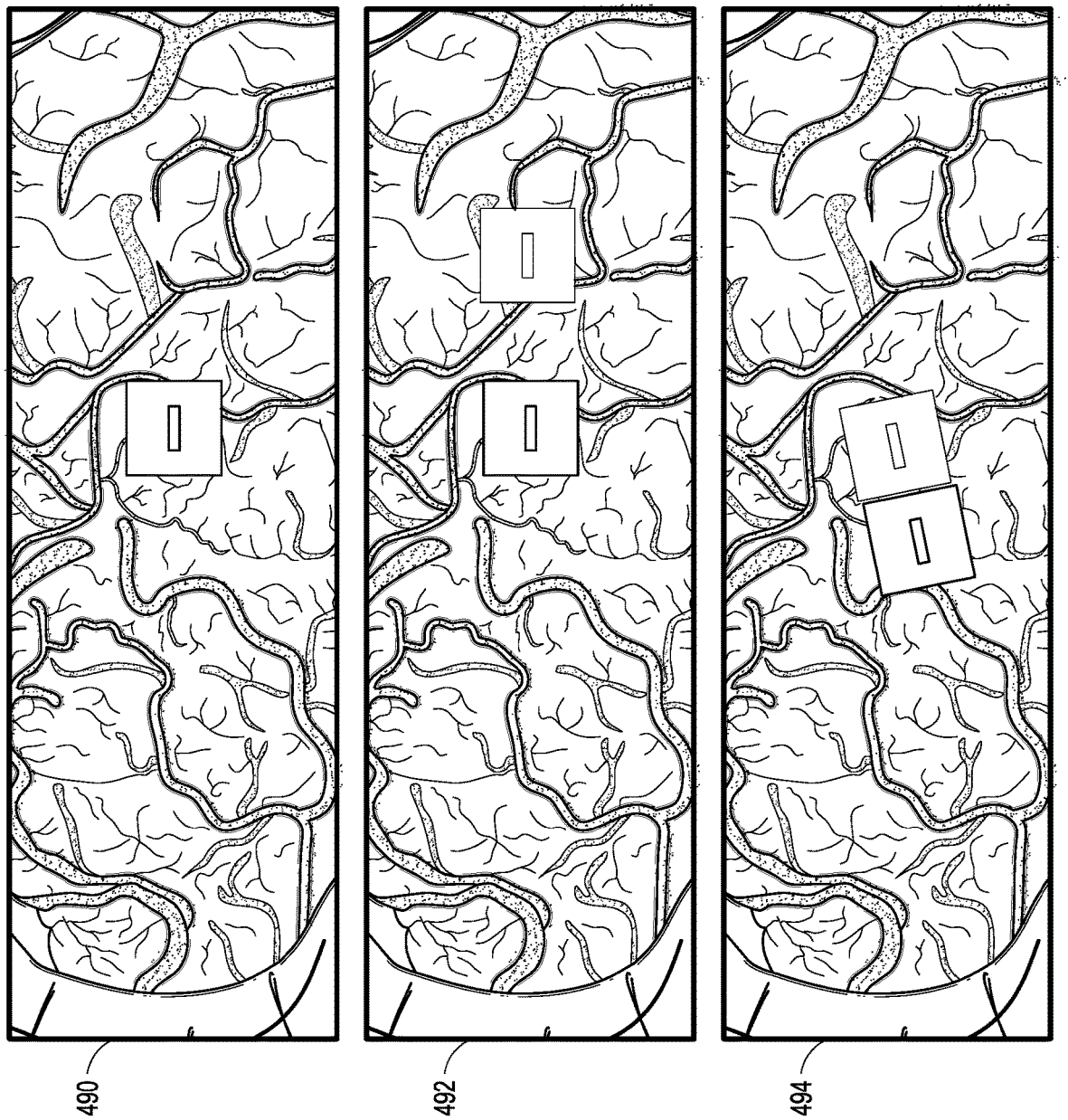
FIG. 5D illustrates an example of the Add and Move operations.

FIG. 5D illustrates a portion of a planning image at three different stages 490, 492, and 494 of a treatment planning process. Beginning at stage 490, the planning software is in Add mode, such as by the user selecting the Add button from button bar 430. While in Add mode, the user has touched a position on the planning image and a virtual implant has been placed (e.g., a square tile with a default seed position overlaid on an image of a patient's brain). Next, while remaining in Add mode, at stage 492 the user has touched a second position and a second virtual implant has been added, in this example shown with greater transparency. In one embodiment, the user may vary the transparency of individual implants. In another embodiment, transparency may be used to graphically represent a particular characteristic of implants, e.g., implants with higher seed strengths could be displayed with reduced levels of transparency. In another embodiment, different seed strengths within implants could be represented with another visual indicator, such as alteration in color.

Next at stage 494, the user has selected Move mode, such as by selecting the Move button from button bar 430 of FIG. 5A. While in Move mode, the user has touched and dragged the second implant, and as it is dragged and collides with the first placed implant (at stage 490), that first placed implant is moved as the virtual implants act as if they were physical objects. Thus, in this embodiment the virtual implants are assigned interaction properties to imitate how physical objects would interact with one another in the real world, such as by pushing one another in response to impact of other implants. In other embodiments, the interactivity of implants may be adjusted, such as based on user preference, so implants may actually be stacked on top of one another or placed next to one another without pushing an adjacent implant.

Figure 5E:
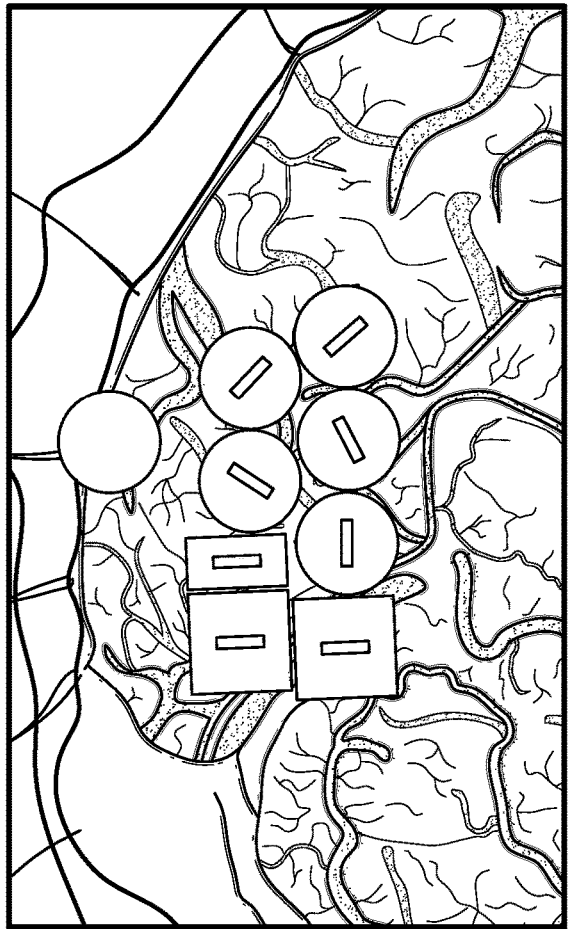
FIG. 5E illustrates another example of how virtual implants act like physical objects with respect to collisions.
Figure 5E:
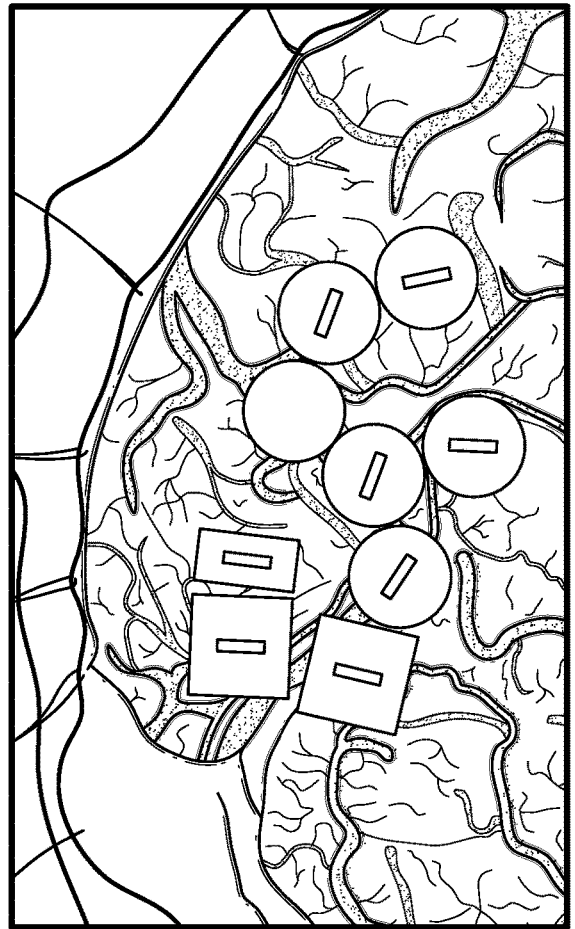

FIG. 5E illustrates another portion of a planning image at two different stages 496 and 498 of a treatment planning process. At stage 496, the user has added a group of eight virtual implants, each with a radioactive seed, of various types. Above the group is a circular implant that is empty, representing a dot spacer without a radioactive seed.

At stage 498, the user has dragged the dot spacer inferiorly and, by doing so, has re-arranged the virtual implants. In this particular example, the dot spacer collided with other virtual implants, moving them inferiorly, and the implants that the dot spacer pushed down collided with other implants, which were moved as a result. Thus, the position of multiple implants can be adjusted in response to interactions with a single implant that is moved by the user. In one embodiment, the user may simultaneously touch multiple implants with different fingers and move them independently.

In another embodiment, virtual implants may be locked so that they do not move when other virtual implants collide with them. When virtual implants are added to a plan, they may be locked in place or mobile, depending on a default setting or user preference.

Locked (immobile) vs. unlocked (mobile) may have differing visual appearances. For example, locked virtual implants may have a lock icon superimposed on them or another visual indicator. In another embodiment, locked vs. unlocked implants may have some other visual difference, for example different colors or different degrees of transparency.

Composite Virtual Implants

Figure 5F:
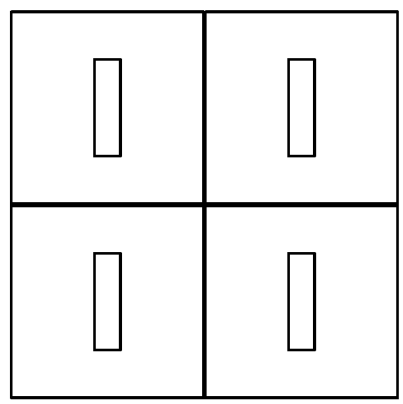
FIG. 5F illustrates another example button bar that includes a composite tile button.

FIG. 5F illustrates another example button bar that includes a composite tile button, a "2×2" button in this example. In some embodiments, "composite tiles" may be selected from available carriers and/or composites tiles may be created by the user. In general, a composite tile (or "composite carrier" or "composite virtual implant" more generally) is a group of tiles (or other virtual implants) that may be moved concurrently. With reference to the example of FIG. 5F, with the "2×2" button selected, a new composite tile 520 is created in the treatment plan. In other embodiments, any other combination of virtual implants may be selected for inclusion in a composite virtual implant. For example, a composite virtual carrier may be created in any arrangement (e.g., 2×2, 2×3, etc.), and include virtual carriers of any shape (e.g., squares, rectangles, hexagons, circles, etc.) and having any characteristics (e.g., all the same seed strength, a pre-set seed strength for central tiles with a lower seed strength for perimeter tiles, etc.).

In some embodiments, the composite virtual implant button (or other user interface control) comprises a drop-down user interface that allows the user to select dimensions of the composite virtual implant that is desired, as well as possibly the specific types of virtual implants to be included, spacing between virtual implants, characteristics of composite virtual implants (e.g., concurrent movement, separation, etc.), and/or any other characteristics of a composite virtual implant. For example, a default concurrent movement characteristic may indicate that all virtual carriers of a composite virtual carrier are moved concurrently when any one virtual carrier is move. A separation characteristic may indicate, however, that certain actions performed on one or more virtual carriers of a composite virtual carrier will cause those one or more virtual carriers to be separated from the composite virtual carrier (and then perform the certain actions). In other embodiments, these characteristics may have different defaults, may be user defined, and/or may be selected on-the-fly by a user as composite virtual implants are created and/or manipulated.

In some embodiments, composite virtual carriers may be created in other manners. For example, in some embodiments multiple tiles may be selected (e.g., by selecting multiple tiles while holding down the shift button on the keyboard) and then a "create composite" button (or similar user interface element or keyboard shortcut) may be selected (not shown in current figures) in order to create a composite virtual carrier including each of the selected tiles. In this way, composite tiles including various types, quantities, orientations, radiation levels, etc. of virtual implants may be associated as a composite virtual carrier and manipulated concurrently.

Figure 5G:
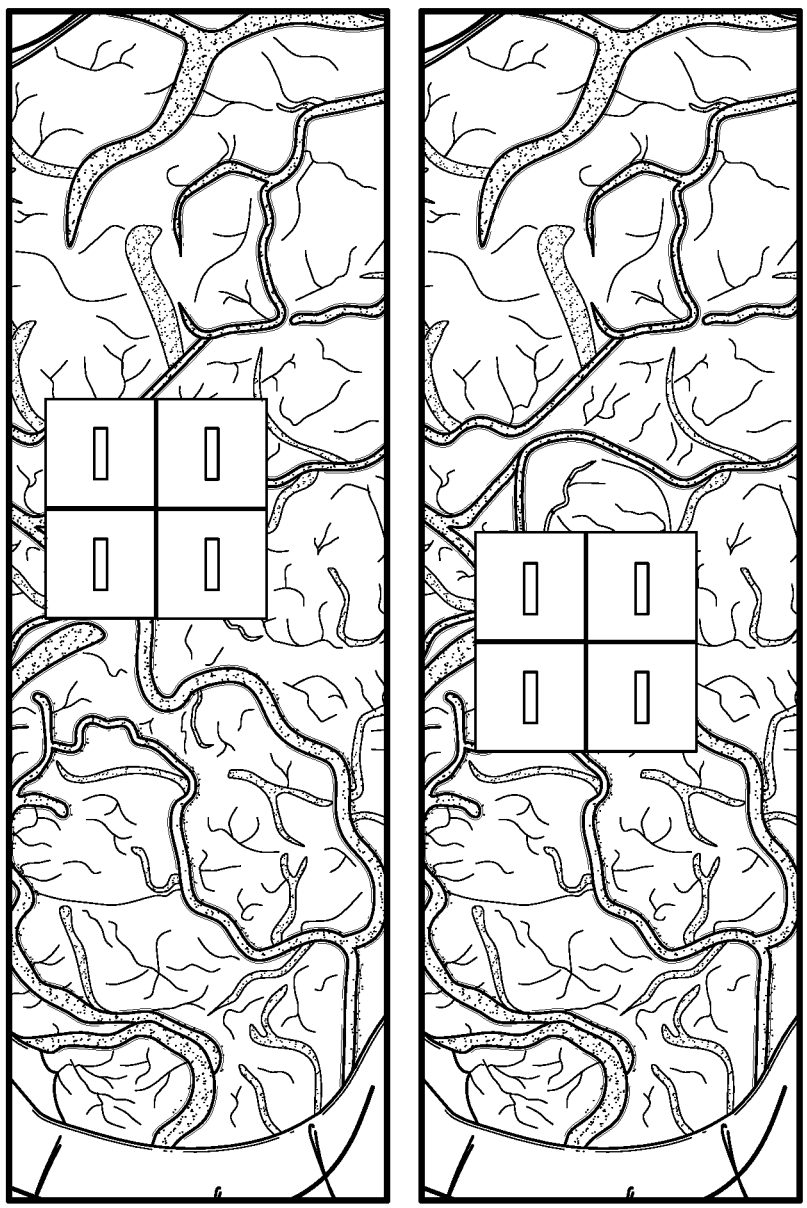
FIG. 5G illustrates placement of a composite tile and movement of the composite tile.

FIG. 5G illustrates placement of a composite tile and movement of the composite tile as a single unit. For example, the composite tile in the upper image may be moved to the left by selection of any region of the composite. In this way, movement of a group of tiles (or other virtual carriers) may be easily accomplished without impacting other characteristics of the virtual implants.

Figure 5H:
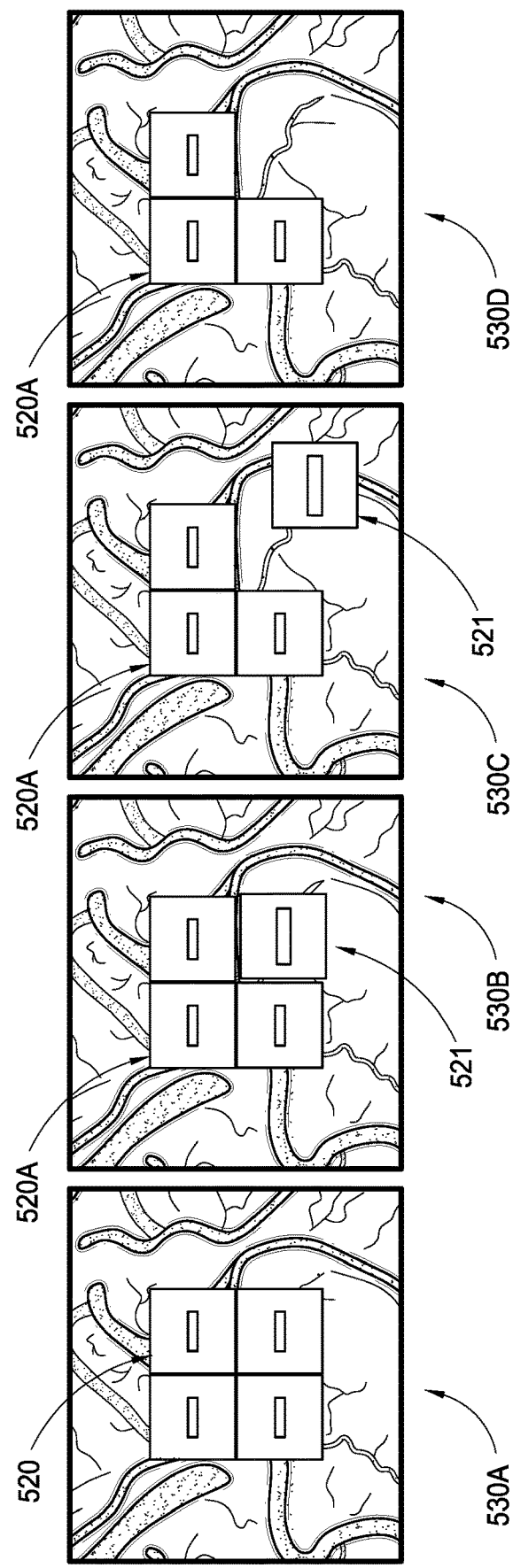
FIG. 5H illustrates a process of disconnecting a virtual implant from a composite tile by flipping the virtual implant.

FIG. 5H illustrates a process of disconnecting a virtual implant from a composite tile by flipping the virtual implant. As shown at state 530A, the composite tile 520 has been placed on the planning image. At state 530B, one of the tiles 521 of the composite tile 520 has been selected for flipping (e.g., by selecting the flip button and then selecting tile 521). In one embodiment, this operation may result in separation of the composite tile into its separate components, such as into the 4 separate tiles, or only separating the one selected/flipped tile and creating a new composite tile including the remaining 3 tiles.

As shown in the example of FIG. 5A, the flipping action applied to tile 521 has caused tile 521 to flip (indicated by the larger seed representation in tile 521) and tile 521 to be separated from the remainder of the composite tile, now labeled composite tile 520A to indicate a different composite tile including only three tiles. With tile 521 separated from the composite tile 520A, it may now be separately moved, as shown at state 530C, removed from the treatment plan, as shown at state 530D, and/or otherwise manipulated separate from the composite tile 520A.

In other embodiments, a flip (or other) operation may be configured to apply to each virtual implant of a composite virtual implant so that, for example, selection of one virtual implant of a three virtual implant composite carrier for flipping would cause all three of the virtual implant to flip. In some embodiments, the user has both functionalities available and can select which functionality to use when working with a composite virtual implant, such as by a user interface control or shortcut key (e.g., holding down on shift while selecting a virtual implant separates the virtual implant from the composite carrier and causes only the separated virtual implant to receive the selected action, such as flipping, while holding down on Control while selecting a virtual implant causes all virtual implants in the composite to receiving the selected action).

Example Dose Readings

Figure 6A:
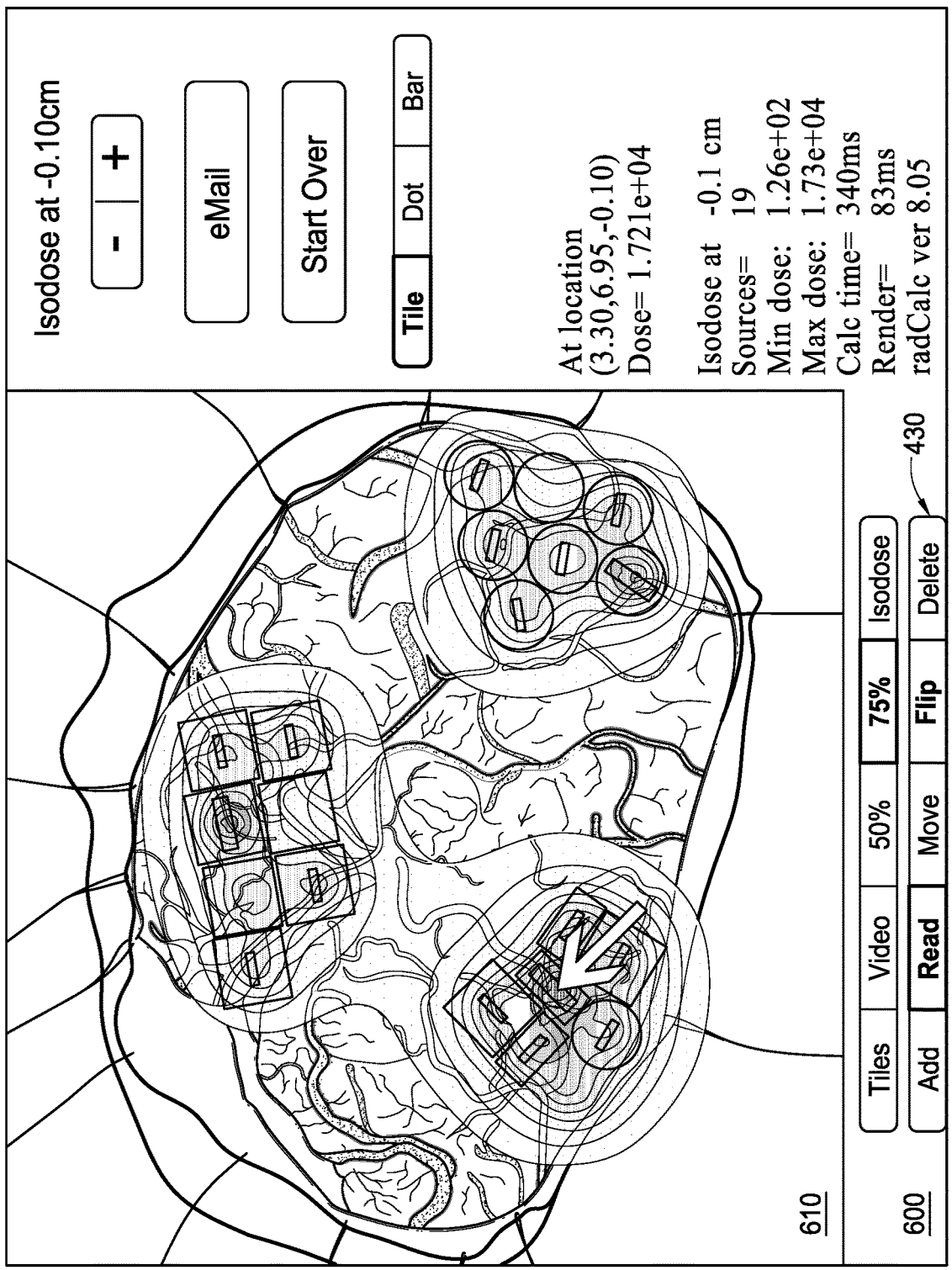
FIG. 6A illustrates a number of virtual implants that the user has placed on the planning image, illustrated as multiple square, rectangular, and circular graphics, representing various types and configurations of virtual implants.
Figure 6B:
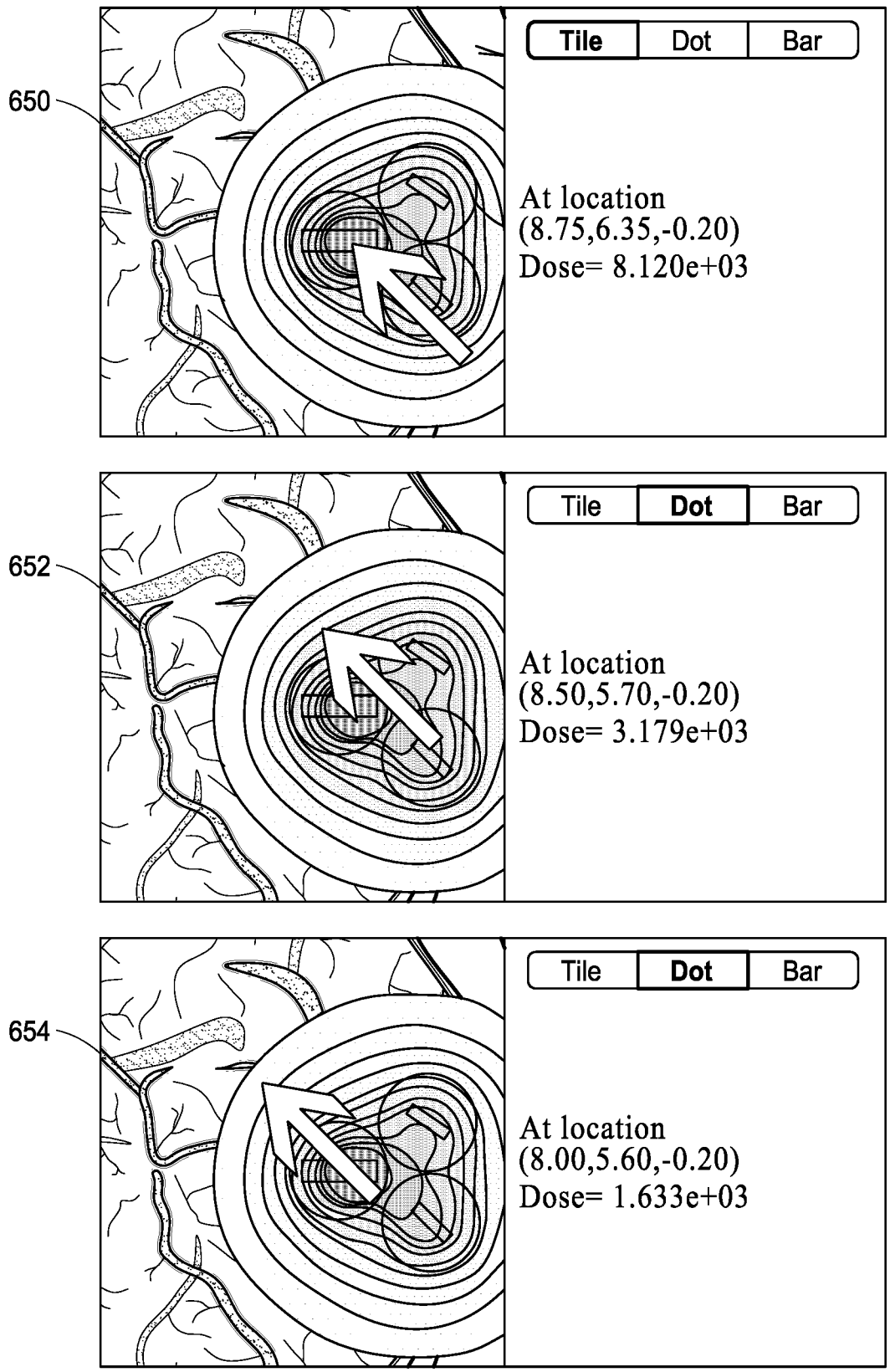
FIG. 6B illustrates measurement of dose at different positions.

FIGS. 6A and 6B illustrate a planning user interface 600 depicting an example planning image in a display frame 610. In this example, the "Read" function of button bar 430 has been selected. As described herein, the calculated 3D dose that results from the virtual implants may be configured to automatically and continuously calculate as the user manipulates virtual tiles. In addition to a graphical display, for example in the form of an isodose plan, the user may obtain a numeric value at any 3D position by tapping a location in display frame 610 to choose the (x,y) coordinates to report. As discussed elsewhere, the calculated dosage at a particular selected position may be provided in various formats (which may be automatically selected by the planning system or by the user), such as to provide relative and/or absolute dose readings. The z position, or depth, may be chosen via the "+|–" buttons of the user interface or a similar method, with the z position displayed in the upper right corner of the user interface, such as isodose depth 452 of FIG. 5C.

In the example of FIG. 6A, an arrow has been displayed in response to the user tapping a position in the display frame 610 (with the Read mode activate), which indicates a position to be read. The numeric value of the dose at the selected location may then be reported to the right of the display frame, starting with "At location:" and may include the 3D coordinates of the position chosen as well as the dose, in this example 1.721e+04. In other embodiments, different symbols may be displayed to indicate a selected area for providing dose data, or no indicator may be displayed in some embodiments. In some embodiments, dose information may be displayed near or atop the selected treatment surface position, such as near the arrow illustrated in FIG. 6A.

FIG. 6B illustrates a portion of a planning image at three different stages 650, 652, and 654 of a treatment planning process. These three stages illustrate examples of readings in different positions. In this example, dose decreases with increasing distance from the implants, in this case the virtual radioactive implants. In particular, at stage 650 a dosage calculation for a particular area of treatment plan in a region of the isodose plan having a visual indicator associated with a high dose range (for example, indicated by a color, e.g., red, and/or pattern of between isodose curves, for example) is provided. At the particular selected area at stage 650, the calculated dose is indicated as 8.120e+03. At stage 652, in response to the user selecting a position that is approximately 7 mm from the more central reading shown at stage 650, the isodose plan has a different visual indicator (for example, a different color, e.g., intermediate shade of blue, and/or pattern) indicating a lower dose value, and the calculated dose for that particular location (in this example) is 3.179e+03. Next, at stage 654, at a position that is even further from the more central reading shown at stage 650, the isodose plan has another visual indicator (for example, a different color, e.g., dark blue, and/or pattern) to indicate an even lower dose value, indicated in this example as 1.633e+03.

In some embodiments, the implant planning system allows selection of a virtual shielding material for placement on the planning image and inclusion in a developed treatment plan. In such an embodiment, the virtual shielding material emulates properties of a physical shielding material such that radiation dosages illustrated in isodose plans are affected by placement and movement of the virtual shielding material. In this way, a user may place a particular virtual shielding material (e.g., multiple sizes, materials, shapes, and/or configurations of shielding material may be available) beside and/or above one or more carriers in a treatment plan and the isodose depth may be adjusted so that radiation levels above the carrier configuration are indicated. For example, an isodose depth of +2 cm may cause the planning software to generate an isodose plan illustrating any (stray) radiation above the patient's anatomy, such as above bandaging that is placed over a physical carrier configuration and that may introduce an increased radiation risk to the patient and or persons that come near the patient. Thus, isodose curve calculation at these levels, and based on configurable use of different types and placements of shielding materials, may contribute to a treatment plan having an optimized efficacy.

Implant Placement Guide System

As discussed below, an implant placement guide system may be used to guide a surgeon in placing physical implants based on a treatment plan, such as an implant plan developed using the implant planning software discussed above. Once a user creates a treatment plan using virtual implants (such as using the implant planning system discuss above and/or some other system), there is a need for a system that is efficient, accurate and intuitive to guide the surgeon in placing physical implants according to the plan.

Figure 8:
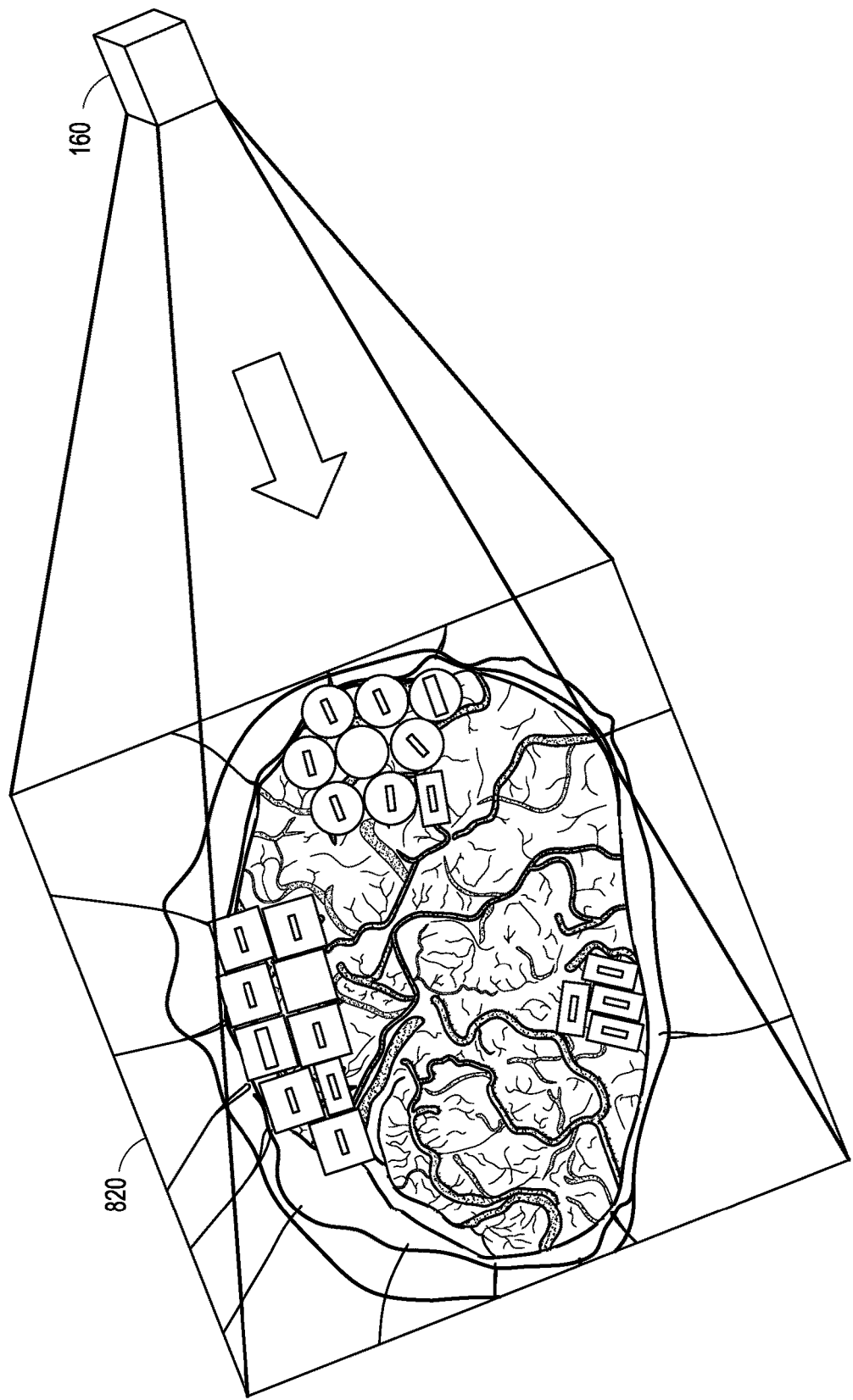
FIG. 8 illustrates an embodiment where a digital projector 160 projects the plan, in this example as the black and white virtual implants, on to the patient's body 820, in this example a patient's brain during surgery.

In one embodiment, a treatment plan is projected on to the patient anatomy (e.g. that physical treatment surface of the patient), for example using a computer display in the form of a projector that can project visual information on the body, such as a surgical cavity (e.g., the surface of the brain). The information projected on the treatment surface (e.g., the brain surface) can show the surgeon the type, configuration, and/or location of each physical implant that needs to be placed in or on the treatment surface. FIG. 8 illustrates, for example, an embodiment where a digital projector 160 projects the treatment plan, in this example as the black and white virtual implants, on to the patient's body 820 (e.g., a treatment surface of the patient that is exposed in a surgical setting and is prepared for receiving physical implants). In this example, the treatment plan is projected onto a patient's brain during surgery.

Figure 9:
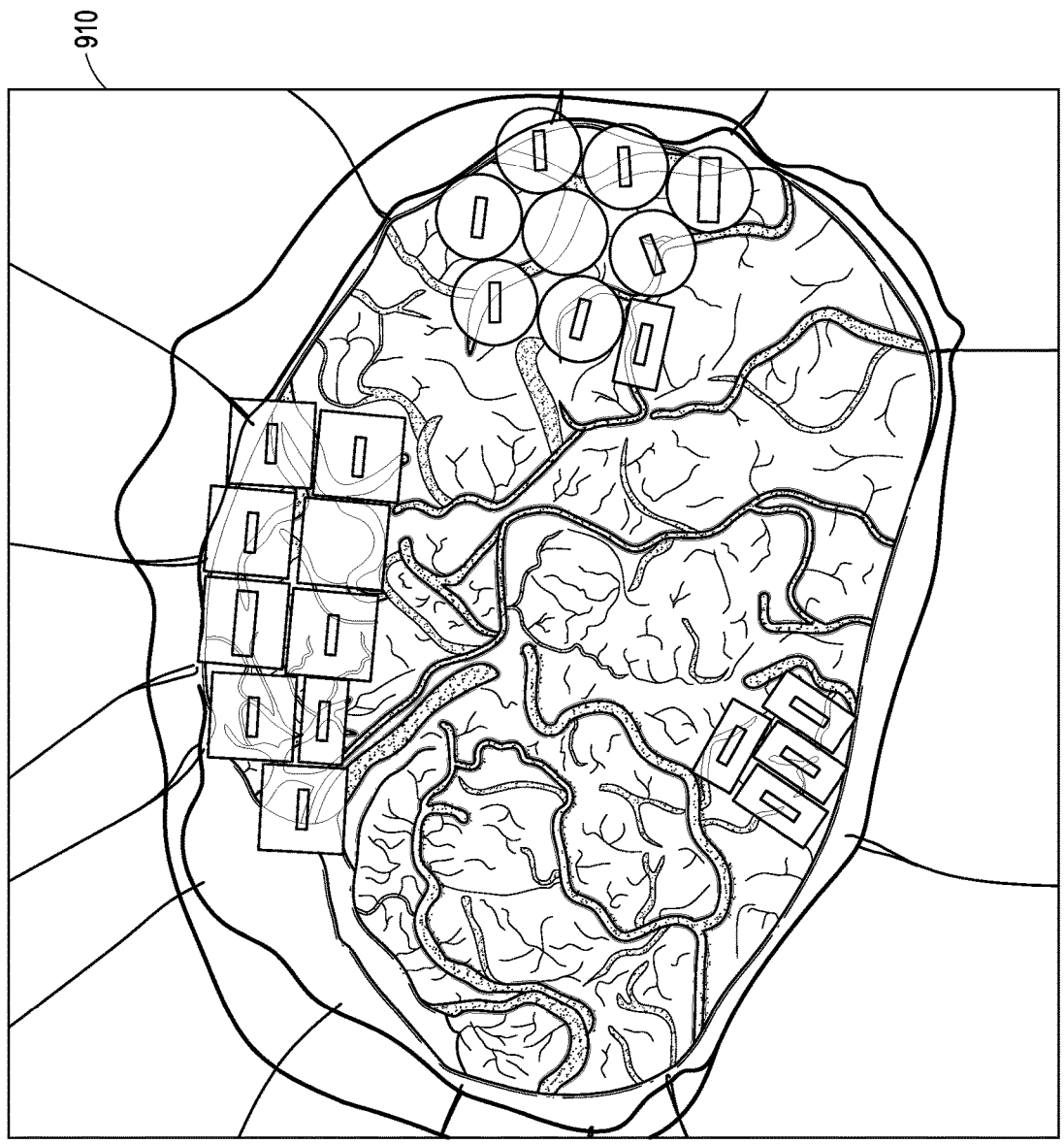
FIG. 9 illustrates an example of virtual implants being simultaneously displayed with the patient's anatomy to guide the surgeon in placing physical implants at the time of surgery.

In another embodiment, a live image of the anatomy (e.g., the treatment surface of the patient), such as a surgical cavity, is acquired using an imaging device, such as a digital video camera, and the treatment plan, including one or more virtual implants, and a live image of the anatomy are simultaneously displayed, for example by graphically superimposing the virtual implants on the live image, so that the surgeon can simultaneously and in real-time visualize the plan, surgical bed, his instruments, and the physical implants he is placing. In the example of FIG. 9, a treatment plan including multiple virtual implants and the patient's anatomy (e.g., from a live video feed from a camera in the surgical room) are displayed simultaneously, such as on a display device positioned in a surgical room, to guide the surgeon in placing physical implants at the time of surgery.

In some embodiments, a treatment plan may be implemented in other manners, such as by 3D printing of physical implants (corresponding to virtual implants in the treatment plan) either local to the treatment planning system (e.g., at the hospital where the treatment plan is developed and the implant placement will occur) or remotely (e.g., at a remote implant provider site that generates the physical implants and mails the implants to the treatment facility). In such an embodiment, 3D printed physical implants may include slots for inserting radioactive seeds, such as just prior to implantation of the physical implants. In other embodiments, a special-purpose 3D printer may automatically embed radioactive seeds into the printed 3D physical implants, such as by selecting the radioactive seeds from a storage container or magazine and placing on a partially printed physical implant prior to enclosing the seed in the implant by completing the 3D printing. In some embodiments, the physical implants (whether 3D printed or otherwise manufactured) may include connectors, such as slots and extension members, on opposing physical implants that allow generation of a physical implant composite that includes multiple physical implants that are concurrently movable. For example, connectors between each adjacent pair of physical implants may be unique, such that physical implants are connectable only in the pattern shown in the developed treatment plan (including ensuring orientation of certain physical implants that may be flipped with relation to others).

In some embodiments, the implant placement system may include optical sensors (e.g. one or more cameras) that acquire images of the treatment area (e.g., an exposed cavity of human tissue) and automatically registers the acquired images with the planning image on which the treatment plan was generated. With the current patient position registered with the planning image, a robotic placement system may automatically place the physical implants on the treatment surface at the specific positions indicated in the treatment plan. In some embodiments, physical implants may be provided to the robotic system (e.g., such as by the virtual implant provider) in a container wherein the physical implants are in a particular, known, order, such that the robotic system can pick up a first virtual implant (e.g. a top virtual implant in a spring-loaded magazine) and place that physical implant at the location indicated in the treatment plan, and then return to pick up a second physical implant (e.g., that is now at a top of the magazine) and place it at the location determined in the treatment plan, and so on. In other embodiments, the virtual implants may be packaged in other manners that allow robotic and/or manual placement to be more effectively performed.

Registration of Treatment Plan with Physical Anatomy

In order for the treatment plan, including the virtual implants, to be accurately projected or superimposed on the anatomy, the planning image (and plan which is in the same frame of reference) should be registered with the anatomy. For example, the treatment plan and the associated planning image (and/or an image derived from the planning image) may be translated, magnified, rotated, or morphed so that the patient's anatomy and plan match. In this way, the positions, sizes, and orientations of the virtual implants can be accurately represented on the patient's body to guide accurate placement of physical implants. In some embodiments, the planning image is first registered with a live image of the patient's anatomy (e.g., an image of the treatment surface of the patient), and then the planning image (e.g., the combination of implants that comprise the developed treatment plan) may be adjusted in the same manner as the planning image before the treatment plan is implemented. For example, a determined rotation, translation, magnification, etc. calculated in order to register the planning image with a live image of the patient's anatomy may be applied to the treatment plan before the treatment plan is used in the implant placement process.

A number of different methods could be used to register the planning image with anatomy at the time of implantation. In an embodiment where the treatment plan is physically projected on the treatment surface of the patient, the location, magnification, and/or rotation of the projected image may be varied by physically varying the projection system, for example by moving it, or by graphically manipulating the electronic image being projected.

In the case where the treatment plan is electronically superimposed on a live image of the treatment surface, the planning image and associated treatment plan and/or the live anatomic image may be manipulated so the two match, for example by adjusting translation, rotation, and/or magnification of one or both.

Figure 7A:
FIG. 7A illustrates a planning image manipulated so that it is a roughly black and white image, for example by removing color and increasing contrast, and then made semitransparent.
Figure 7A:
Figure 7B:
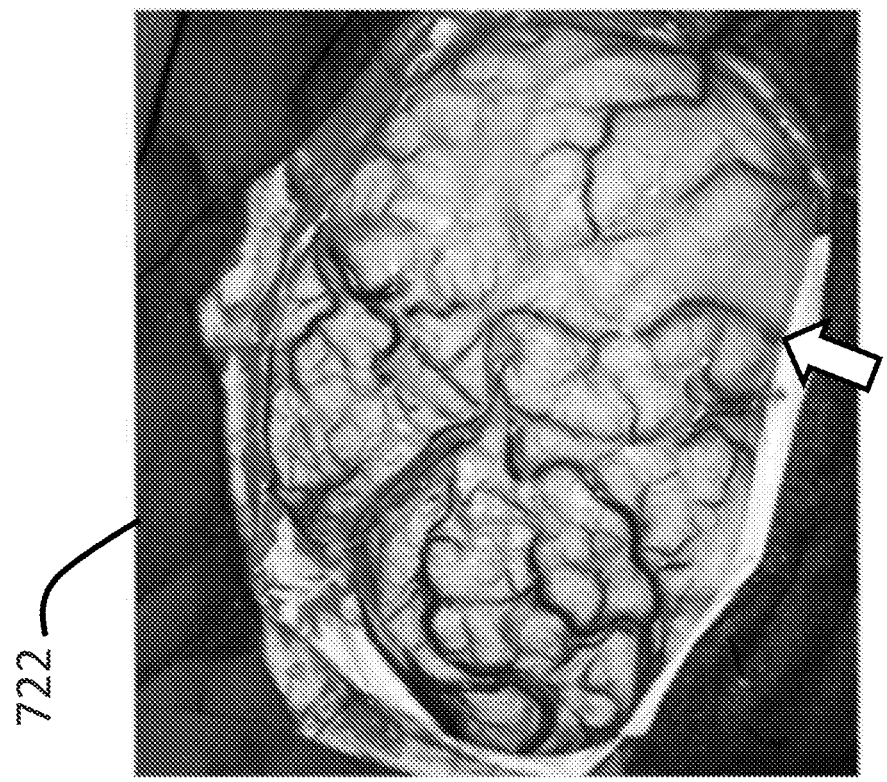
FIG. 7B illustrates the processed planning image superimposed on the anatomy and one can appreciate that the images are not perfectly aligned, as evidenced by the apparent double copy of the vessel indicated by the white arrow.
Figure 7B:
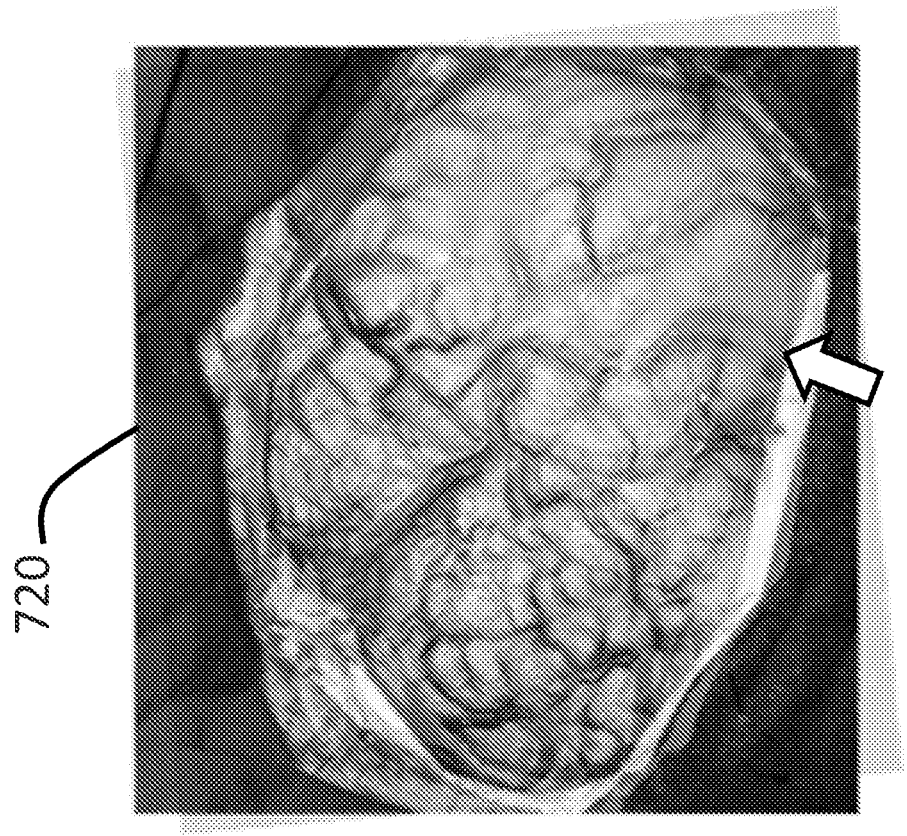

In some embodiments, during the process of aligning the planning image used for the plan and the anatomy at the time of implantation, it may be useful to vary the appearance of one or both images so that it is easier to determine if they are aligned. In the example of FIG. 7A, the planning image 710 is manipulated so that it is a roughly black and white image 712, for example by removing color and increasing contrast, and then made semitransparent. In this way when it is graphically superimposed on the anatomic image, it may be easier to see if the two images superimpose. For example, image 720 of FIG. 7B illustrates the processed planning image 712 superimposed on the anatomy and one can appreciate that the images are not perfectly aligned, as evidenced by the apparent copy of the vessel indicated by the white arrow, and other duplicated anatomical features. In image 722, however, the two images are aligned through rotation and translation so that the anatomical features in each image, such as the vessel indicated by the white arrow, are precisely aligned.

In various embodiments, different graphical methods may be employed to align the planning image (coordinate system of the treatment plan) with the body (anatomy). For example, one image may be subtracted from the other in real time so that user can manually vary translation, rotation, and/or magnification to visually align the two. In other embodiments, the alignment may be performed automatically, for example using cross-correlation, as implemented by Fram (Crepeau, R. N. and E. K. Fram. Reconstruction Of Imperfectly Ordered Zinc-Induced Tubulin Sheets Using Cross-Correlation And Real Space Averaging. *Ultramicroscopy* 6 (1981) 7-18), which is hereby incorporated by reference in its entirety and for all purposes.

In one embodiment, the anatomic image 710 illustrated in FIGS. 7A & 7B may represent a live image of the patient's anatomy, for example obtained with camera 310 of FIG. 3, 2D or 3D Imager 128 of FIG. 1, or Camera 158 of FIG. 1.

Figure 10:
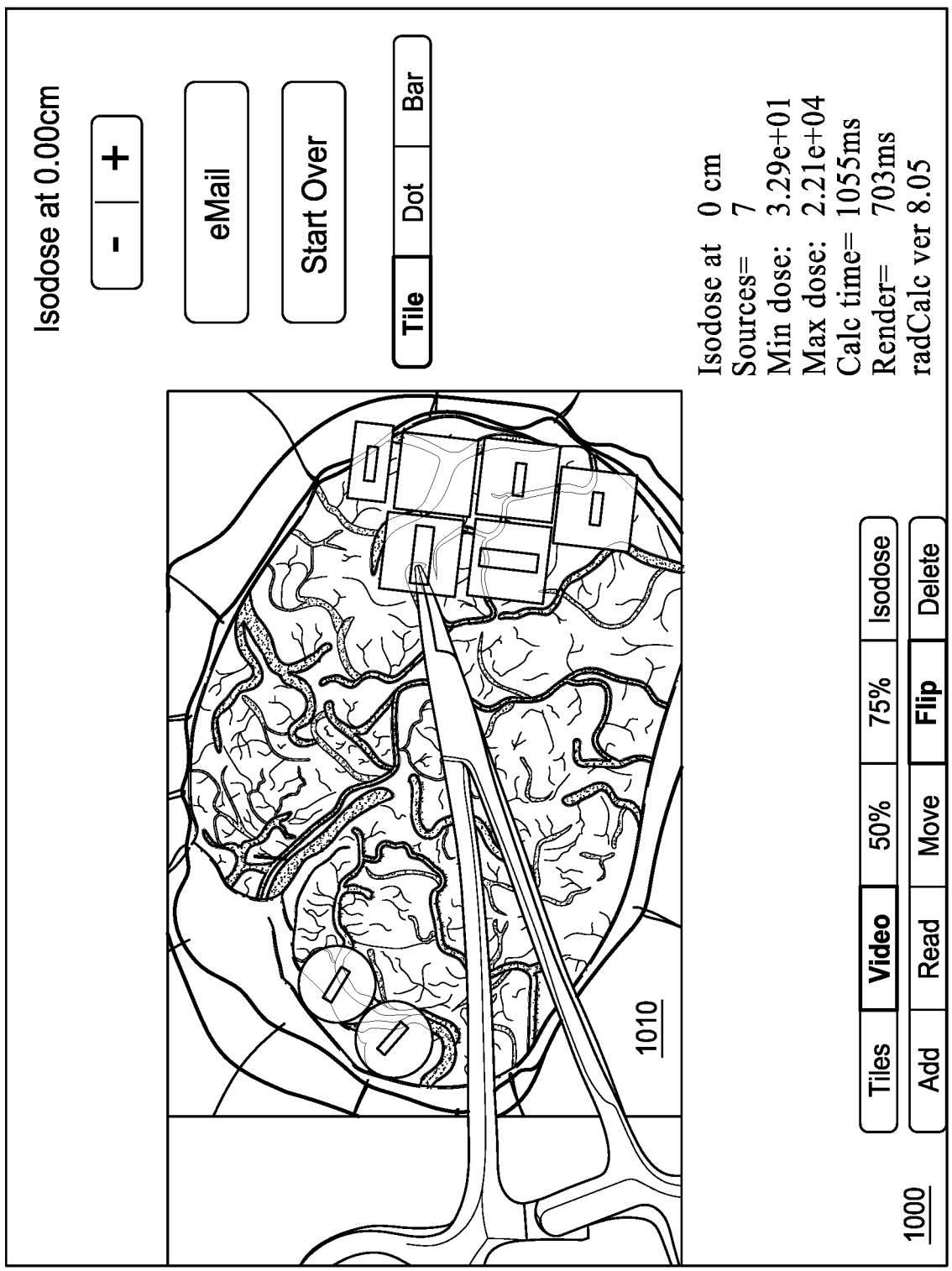
FIG. 10 shows an example of a live video image depicting the anatomy, including a surgical instrument, for example obtained with camera 310 of FIG. 3 or Camera 158 of FIG. 1.

FIG. 10 illustrates a planning system user interface 1000 as may be used as part of an implant placement process. In this example, in response to selection of the "Video" button by the user, the user interface 1000 includes a video window 1010 depicting a live video image (which has replaced the previously displayed planning image) and a graphical superimposition of the developed treatment plan. As shown in this example, the superimposed treatment plan indicates the type, location, and configuration of each of the virtual implants, which allows the surgeon to accurately, efficiently, and intuitively position physical implants corresponding to the indicated virtual implants in the precise locations of the virtual implants by simultaneously visualizing the virtual implants and the treatment surface. Because video window 1010 includes a live video feed in this example, surgical instruments, physical implants, and any other physical objects imaged by the camera are also displayed and may be useful in help the surgeon plan implants while looking solely at the video window.

Figure 11:
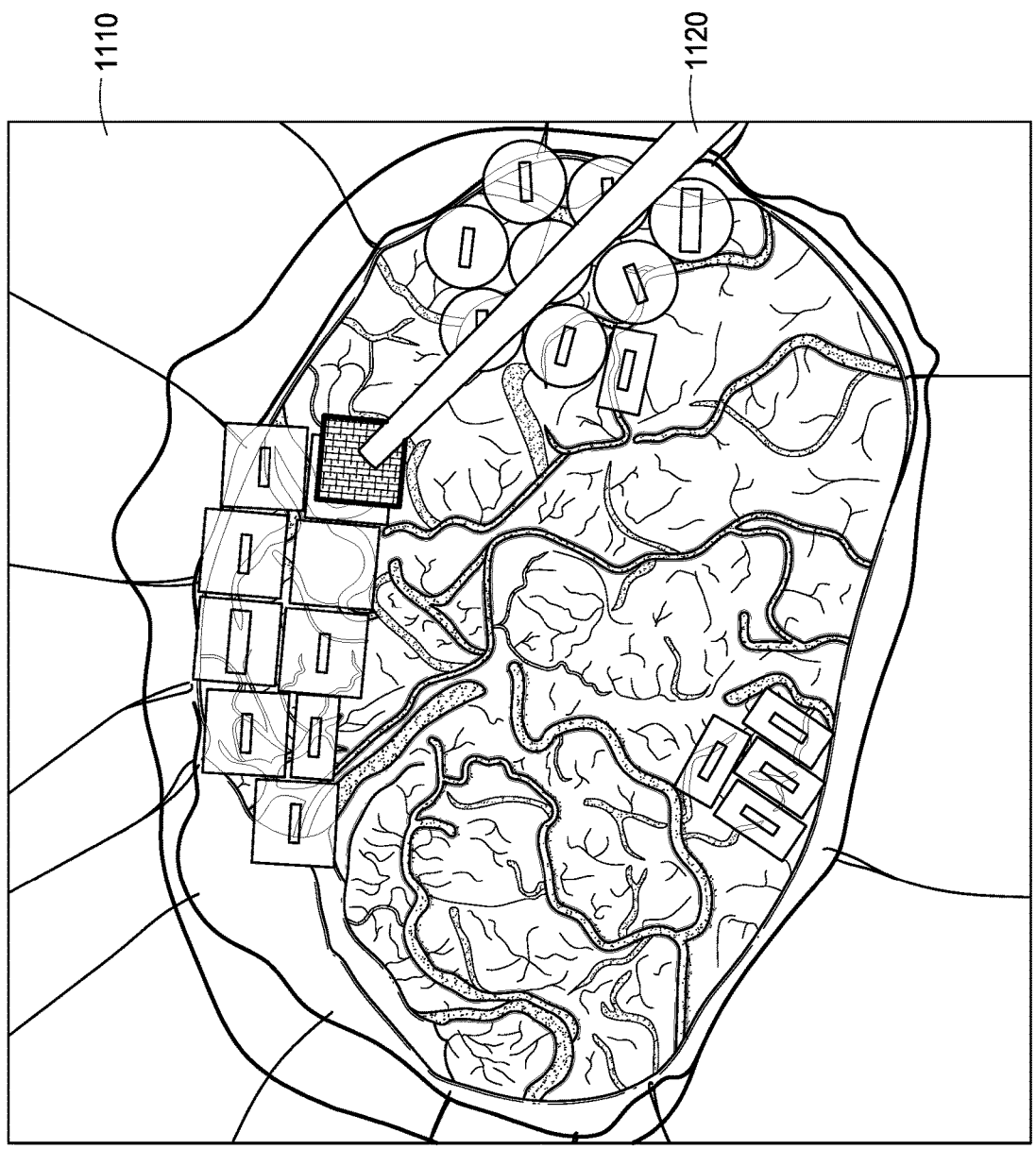
FIG. 11 illustrates a surgical instrument using a gray computer graphic, for example representing an instrument controlled by a surgical robot.

FIG. 11 illustrates another example of imagery that may be displayed in an image/video window, such as window 610 of FIG. 6A of the implant planning (and placement) software. In this embodiment, the "live image" described with reference to FIG. 10 may be a live image or a static image that represents the anatomy at the time of implantation, for example obtained using intraoperative MRI. The real time position of the surgical instrument and/or physical implant being placed may be shown as virtual objects, where the position of the surgical instrument and/or implant is determined using real time position sensing, for example associated with a surgical robot, a real-time stereotactic surgical localizing system, or other real-time position sensing system.

This is illustrated in FIG. 11 where the surgical instrument is shown using a gray computer graphic 1120, for example representing an instrument controlled by a surgical robot or a human surgeon, and the position of the physical implant is shown as a square, textured computer graphic at the end of the instrument.

In the examples illustrated, all the implants in the plan are simultaneously displayed. In other embodiments, implants may be displayed one at a time or in groups, such as groups of adjacent implants (for example, the treatment plan of FIG. 11 might include three groups of adjacent implants). After a surgeon places a physical implant in the position of the displayed virtual implant, the virtual implant may be graphically removed or its appearance otherwise altered and the next virtual implant can be displayed. In some embodiments, an order of appearance of the virtual implants may be prioritized, such as based on default and/or user preferences. For example, in one embodiment the system orders the virtual implants based on an implantation algorithm that determines a most precise, fastest and/or otherwise optimal order in which to place physical implants. In one embodiment, the order generally begins on one side of the treatment surface (e.g., a far side from the surgeon) and moves towards the other side of the treatment service (e.g., a near side to the surgeon). The process can be repeated until all implants are placed.

In one embodiment, the surgeon or a colleague working with the surgeon may indicate that a physical implant has been placed in the position of the currently displayed virtual implant and that the next virtual implant in the plan should be displayed using input such as voice control, mouse, keyboard, touchscreen, or gesture recognition, for example using a video camera or Leap motion controller.

In another embodiment, all virtual implants may be displayed but as the user places a physical implant in the location of a virtual implant, the visual appearance of the virtual implant may change. In one embodiment, the user may indicate that a physical implant has been placed in the location of a specific virtual implant, for example using input systems as above.

In another embodiment, implants may have unique indicators, such as numbers superimposed on them, such that the user may indicate that a virtual implant has been replaced by physical implant using voice input which identifies a virtual implant.

In another embodiment, automatic imaging pattern recognition of a video image of the surgical bed may be used to detect that a physical implant has been placed in the location of the virtual implant, and may indicate placement of the physical implant and/or move on to display a next implant for implantation in any of the manners discussed above.

Additional Optional Features

Figure 12:
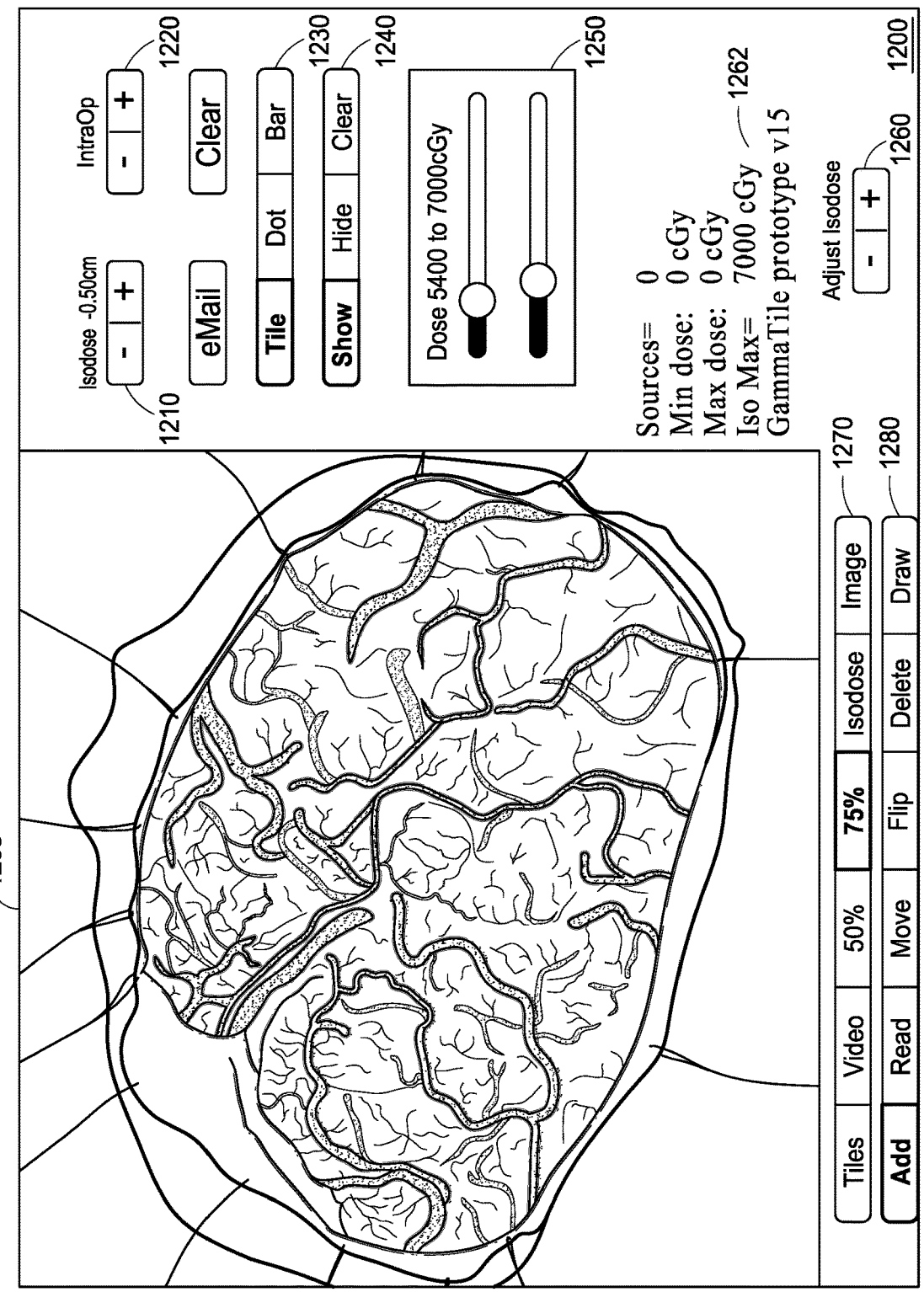
FIG. 12 illustrates an example of a graphical user interface that may be generated by the implant planning system, such as may be implemented on the computing device 150.

FIG. 12 illustrates a GUI 1200 which is similar to GUI 400 in FIG. 4A, but with additional features. Image frame 1205 displays an image. GUI control 1210 allows adjustment of the plane in which the radiation dose is calculated, with the currently selected plane displayed above the control, e.g., the plane is set at −0.50 cm in the example of FIG. 12.

Figure 13A:
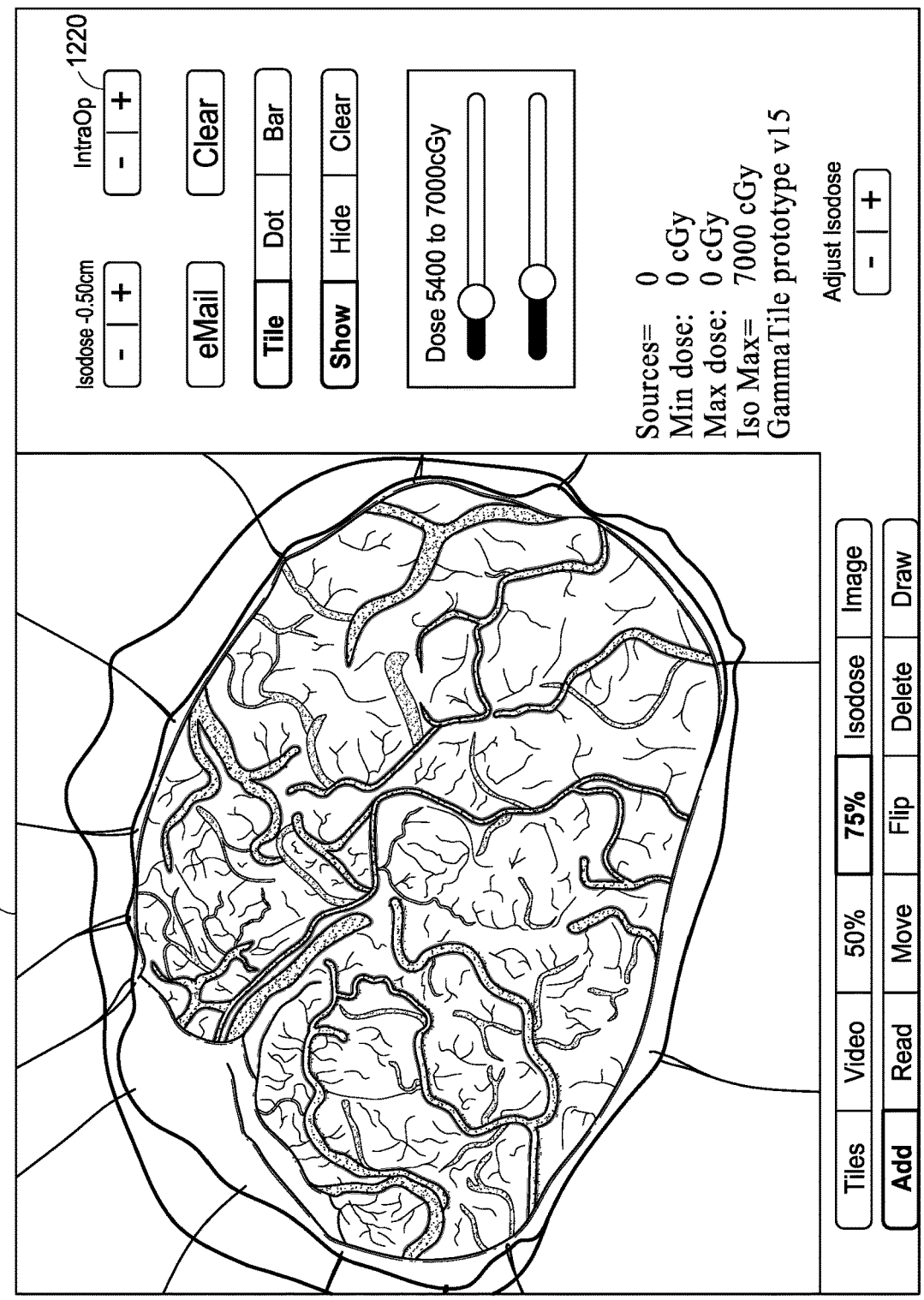
FIGS. 13A and 13B illustrates an example graphical user interface in which various images may be displayed.
Figure 13B:
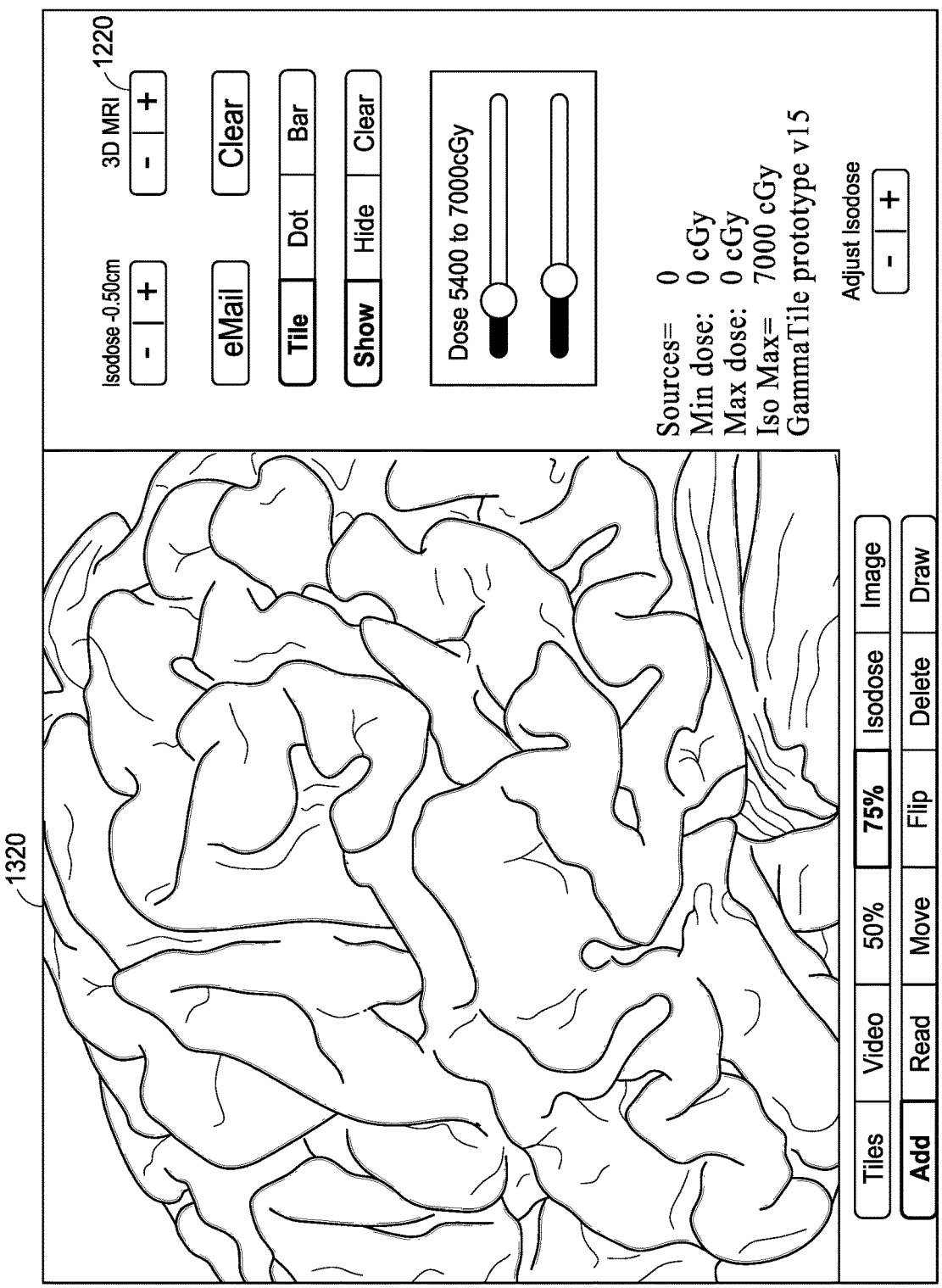

GUI control 1220 may be used to change the image in display frame 1205, for example to another image of anatomy that is in the same frame of reference. A label above control 1220 displays a description of the currently displayed image. For example, FIGS. 13A and 13B illustrates use of a stepper button 1220 (or another other interface element) that has been selected by the user to move between various views of the patient's anatomy that have been registered, e.g., an intraoperative photograph displayed in GUI 1310 of FIG. 13A and the 3D rendering from a preoperative MRI in GUI 1320 of FIG. 13B.

GUI control 1230 includes similar buttons and functionality as is described above with reference to button bar 440 of FIG. 5B.

GUI control 1240 includes buttons that control display and erasure of regions to treat or lesions that may be drawn by the user, as described further below.

Buttons labeled "eMail" and "Clear" have the same or similar functionality as described with reference to buttons 456 and 458 of FIG. 5C, respectively.

GUI control 1250 includes text indicating a range of radiation dose and sliders to control the upper and lower values, as discussed below with reference to FIG. 19, for example.

Figure 14:
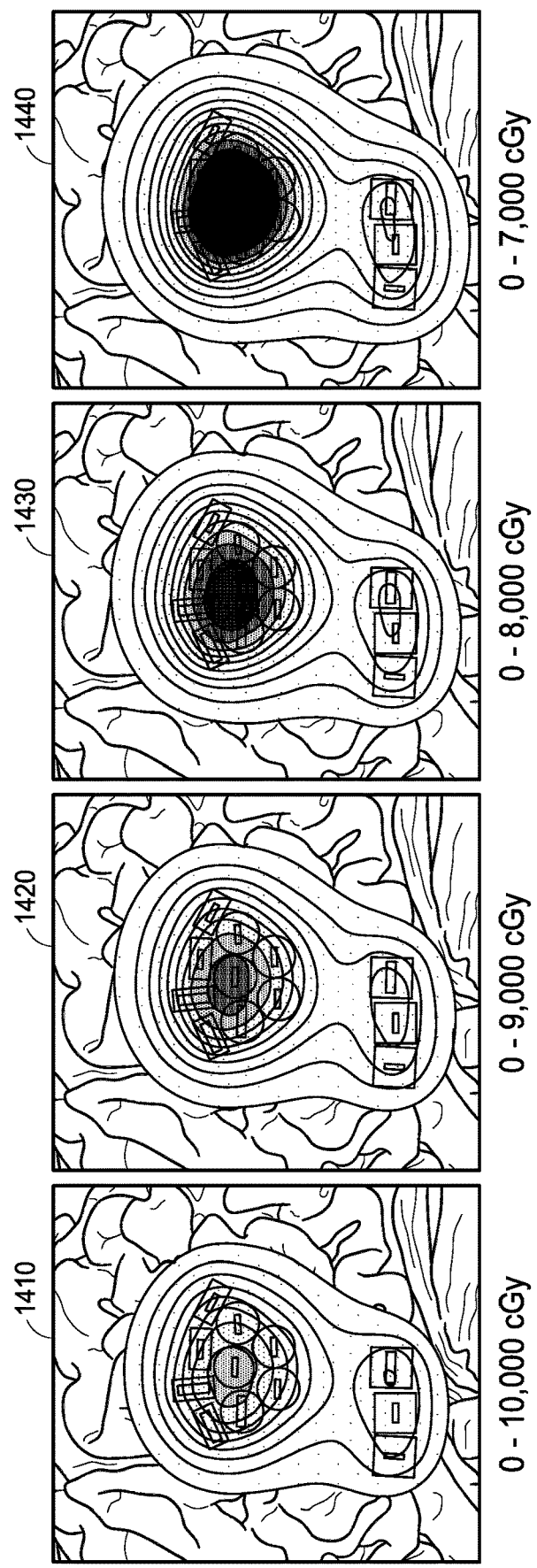
FIG. 14 illustrates display of isodose curves representing radiation dose where the scale of values displayed may be varied.

GUI control 1260 allows the user to control the range of values used to generate isodose curves, with the range extending from 0 (or some other lower boundary) to an upper value controlled by the user with this control and displayed in text 1262. For example, FIG. 14 illustrates an example in which the range of values used in calculating isodose curves (and corresponding colors or patterns that are illustrated in the non-color drawing in FIG. 14 for purposes of clearer publication) are varied. Such adjustments in the isodose range may be implemented using the interface element 1260 (e.g., a stepper) of GUI 1200, for example, to incrementally increase the upper range of values. In this example, the dosage range in image 1410 is illustrated by an isodose plan having a maximum dose of 10,000 cGy, while in image 1420 the maximum is 9000 cGy, in image 1430 it is 8000 cGy, and in image 1440 it is 7000 cGy. Thus, the stepper in this embodiment is configured to decrement (or increment in response to selection of the plus stepper control) the dosage range in increments of 1000 cGy. In some embodiments, the increments applied to the dosage range may be automatically determined from the radiation dose in the current plan, such as to provide predetermined (e.g., 10) levels for isodose curves between a minimum (e.g., 0) and a maximum (e.g., 10,000 cGy) radiation level in a isodose graph.

Button bar 1270 is similar to button bar 420 of FIG. 4B but has an additional "Image" button that allows the user to display the image and lesions and/or regions to be treated drawn in by the user, as well be described below, without superimposition of the tiles or isodose plan while maintaining the treatment plan (e.g., a combination of implants) that has been developed.

Button bar 1280 is similar to button bar 430 of FIG. 4C but has an additional "Draw" button that, when selected, allows the user to draw lesions or regions to be treated on the image in image frame 1205, as will be described below.

Figure 15:
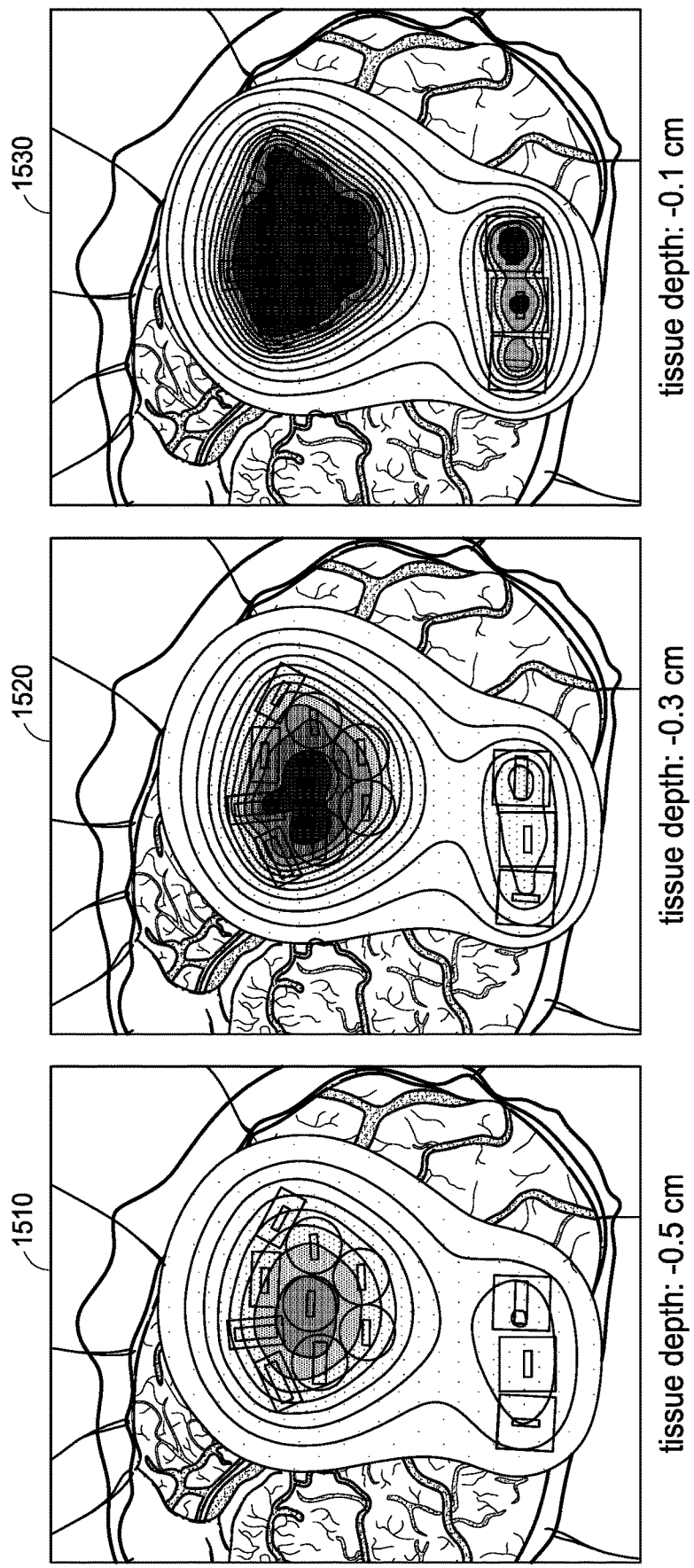
FIG. 15 illustrates display of isodose curves at various depth planes relative to the radiation sources.

In the example of FIG. 15, a group of virtual carriers has been placed and the resulting radiation dose is plotted in an isodose plan including multiple isodose curves and visual indications (e.g., fill patterns or colors) between adjacent isodose curves.

FIG. 15 illustrates the treatment plan at three tissue depths 1510, 1520, and 1530, each having a same isodose curve levels, but at different planes relative to the treatment surface (e.g., brain surface). Specifically, at stage 1510, the radiation distribution at 0.5 cm below the brain surface is shown. As the isodose level changes, such as by the user selecting the GUI control 1210, the isodose curves are updated. In this example, at stage 1520 the isodose level has been adjusted to 0.3 cm below the brain surface and at stage 1530 to 0.1 cm below the brain surface. In this example, seeds in carriers (or other implants) with small icon bars within them are 0.3 cm above the brain surface and the "flipped" tiles (large icon bars) have seeds that are 0.1 cm above the brain surface, and therefore provide a larger dose as they are closer to the brain. Note that the radiation dose increases at tissue depths closer to the brain surface because tissue at those depths is closer to radioactive seeds placed above the brain surface.

Example Lesion Simulation

Figure 16:
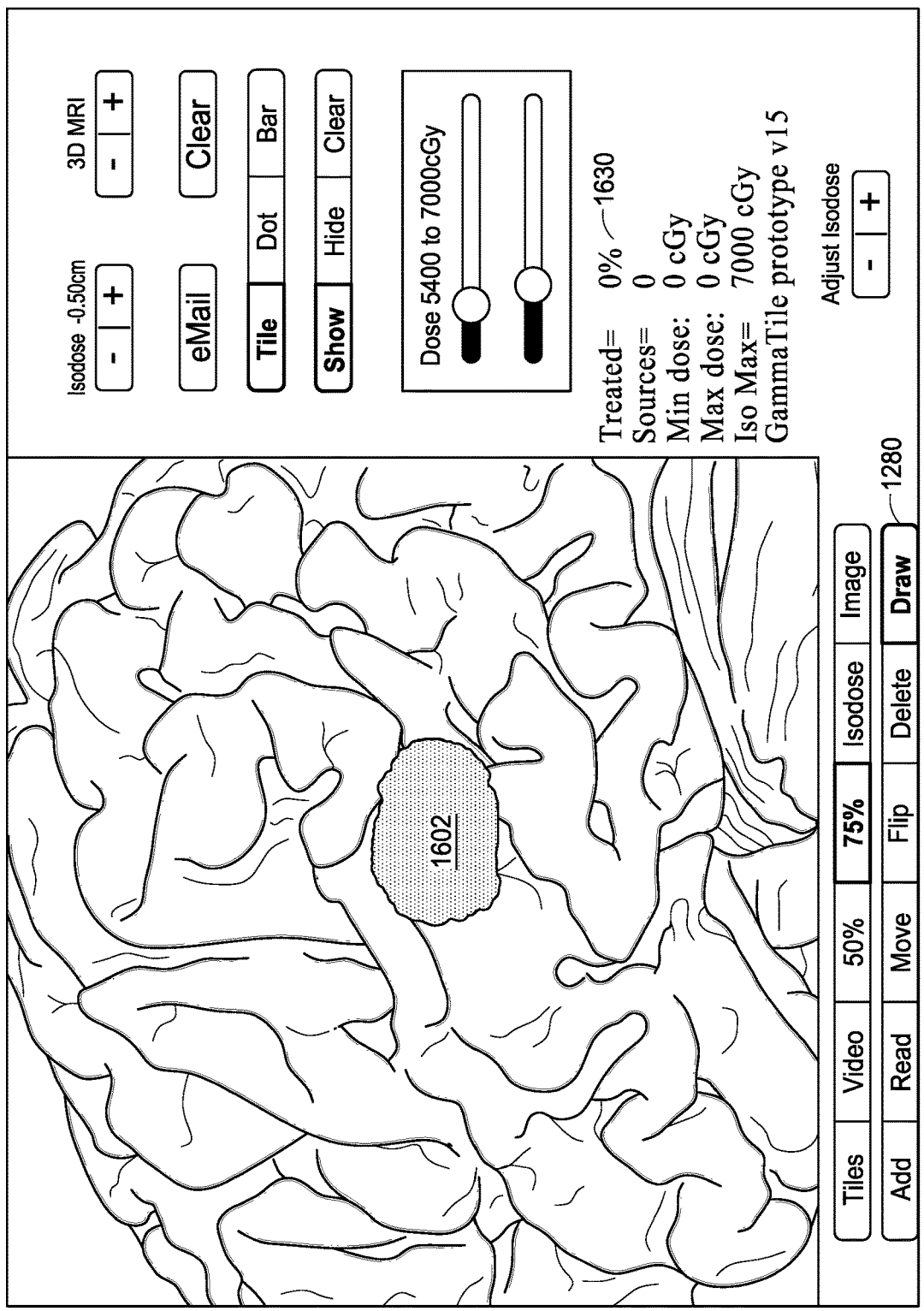
FIG. 16 illustrates a function where the user may interactively draw a lesion or region to be treated.

FIG. 16 illustrates a function where the user may draw a region in the user interface, such as on a planning imaging in the planning system user interface, for example using a mouse or a finger on a touch screen. In this embodiment, this functionality to draw a lesion and/or region to be treated is initiated by the user selecting the "Draw" button of the button bar 1280 which allows the user to draw one or more lesions, e.g., regions to be treated or lesions, onto the patient's anatomy in the planning image. In the example, the user has drawn a treatment region 1602 to be treated in the central portion of the planning image, which may be illustrated in various colors or patterns to indicate user drawn portions of the planning image. For example, in one embodiment the treatment region 1602 is shown in bright yellow color. In this embodiment, a treatment simulation indicator 1630 indicates a quantity of the added treatment region 102 that is receiving a dose above the minimum dose set by the user. For example, in this embodiment the indicator 1630 shows that 0% of the treatment region 1602 would receive a suitable dose of treatment according to the current treatment plan (which doesn't yet include any implants in the example of FIG. 16).

Figure 17A:
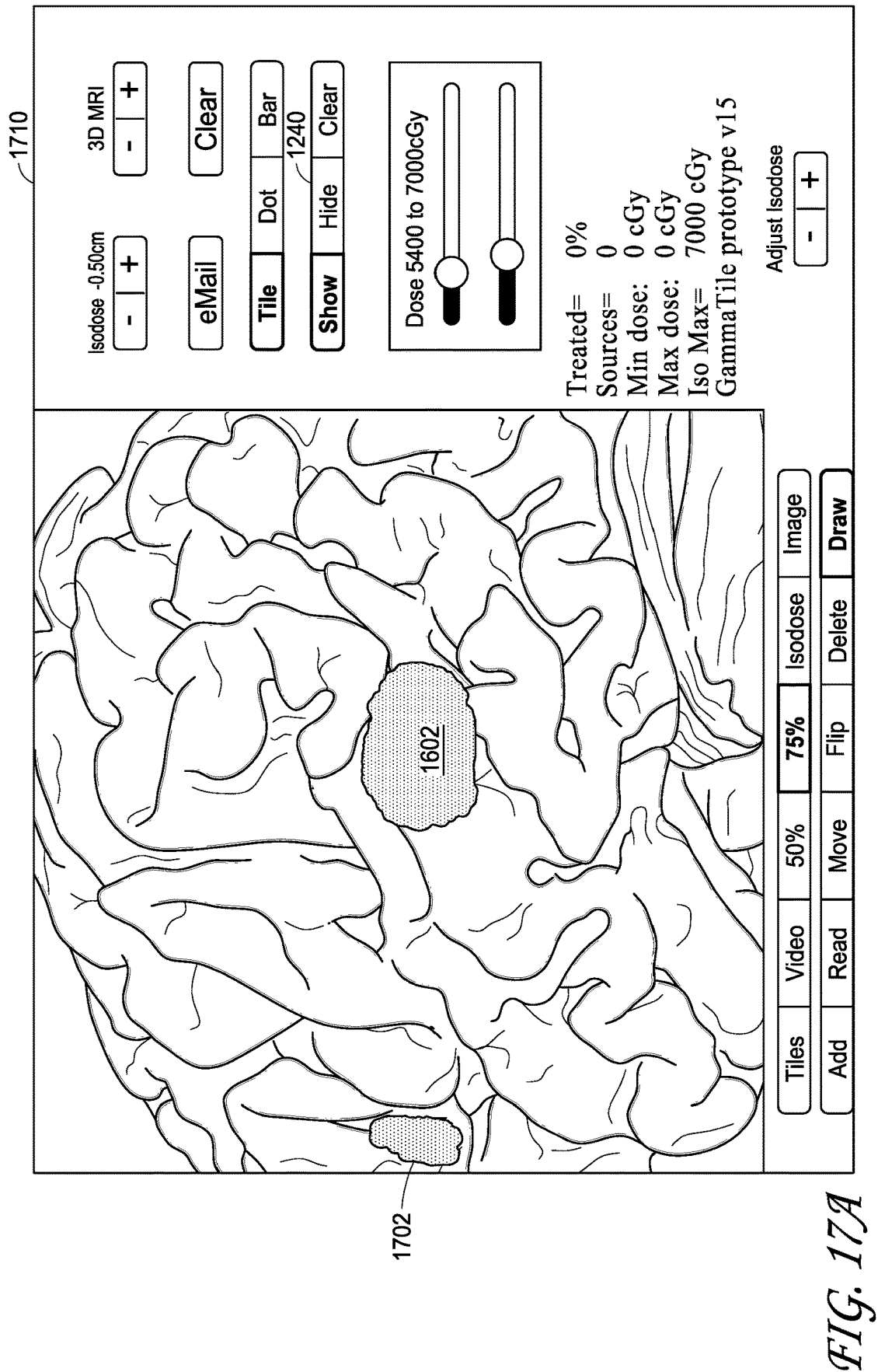
FIGS. 17A and 17B illustrate a graphical user interface where drawn lesions or regions to be treated may be interactively displayed or hidden.
Figure 17B:
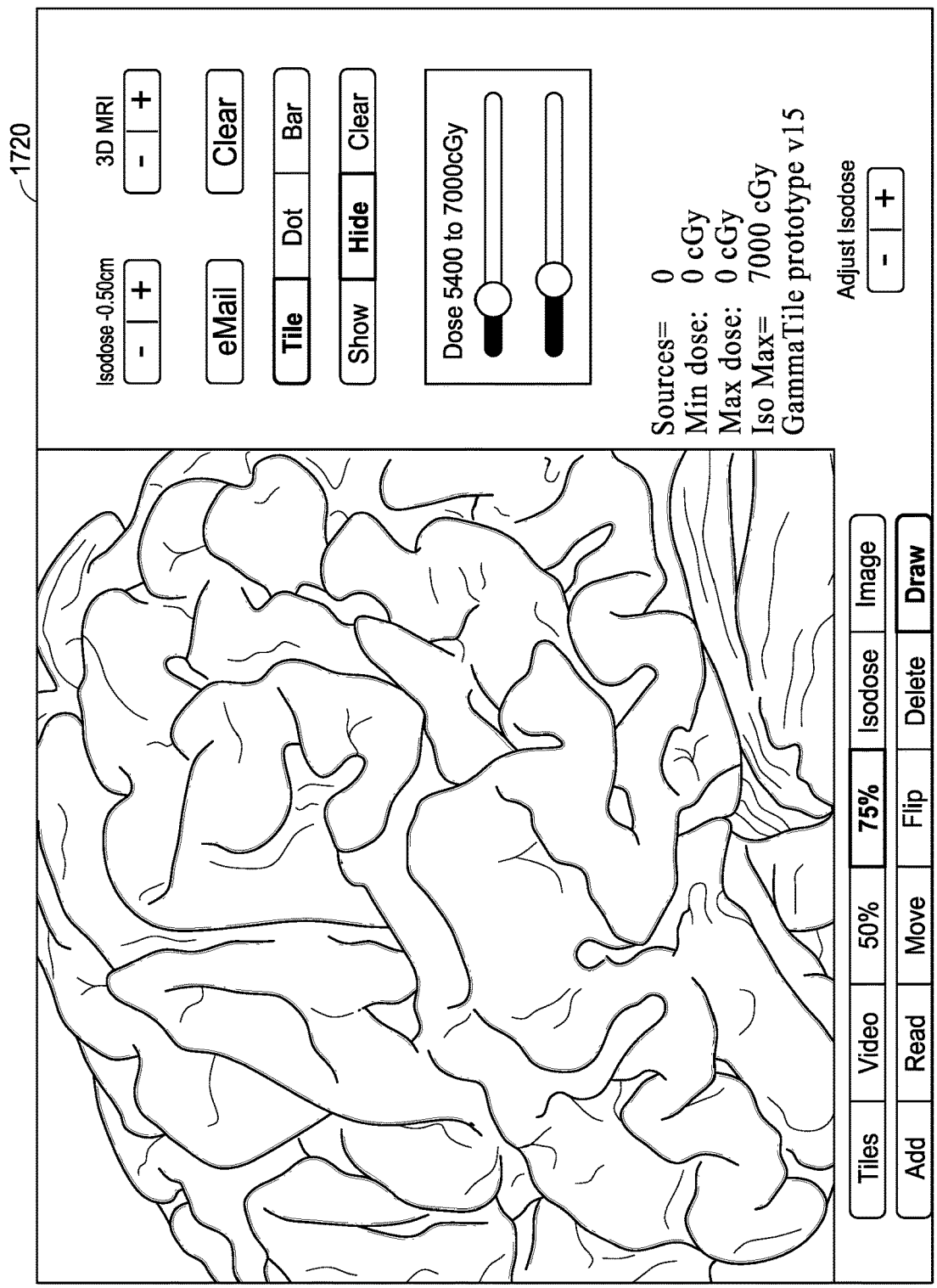
Figure 18A:
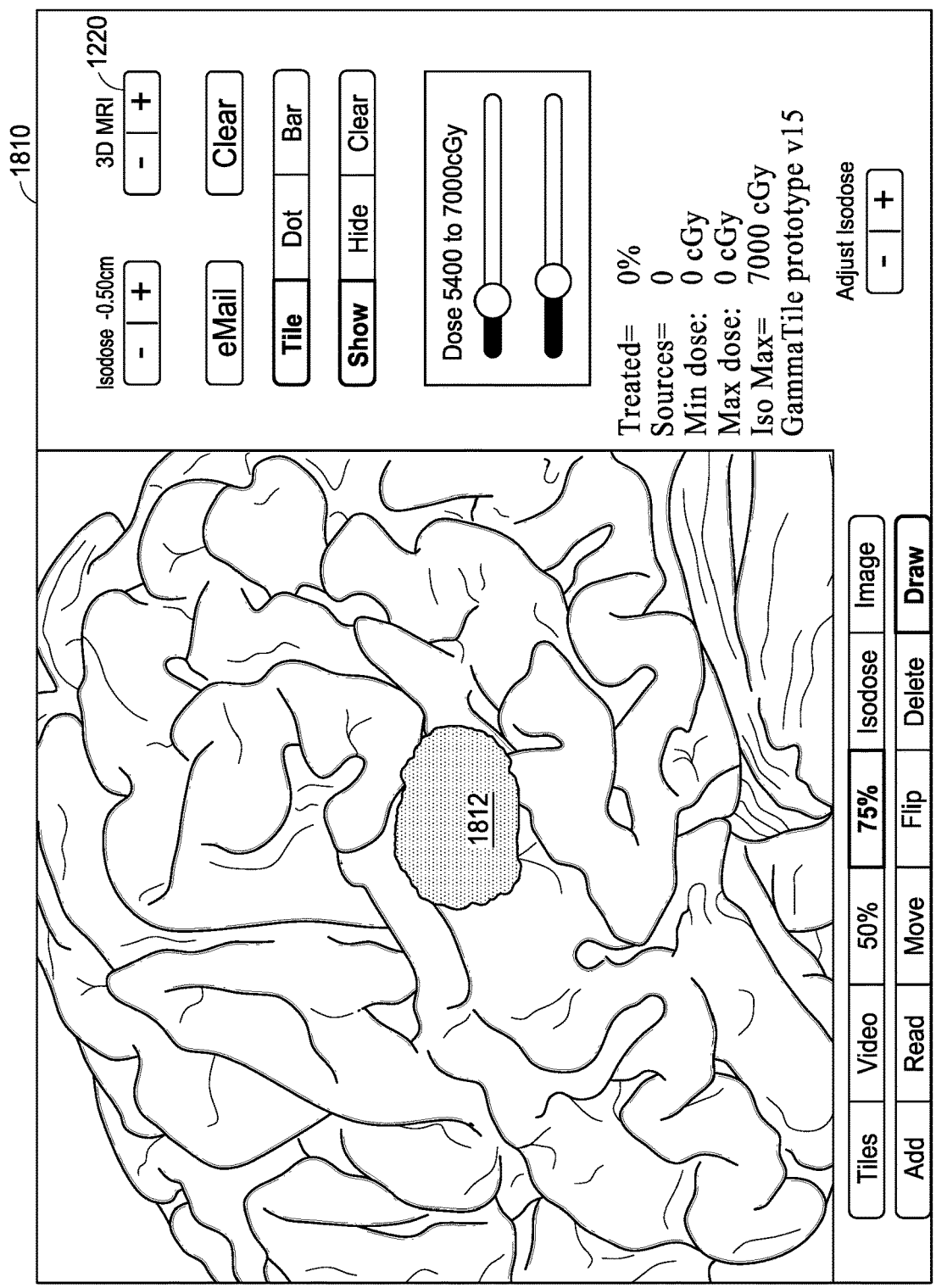
FIGS. 18A, 18B, 18C, and 18D illustrate functionality where lesions or regions to be treated may be drawn on one or more images and displayed on all images.
Figure 18B:
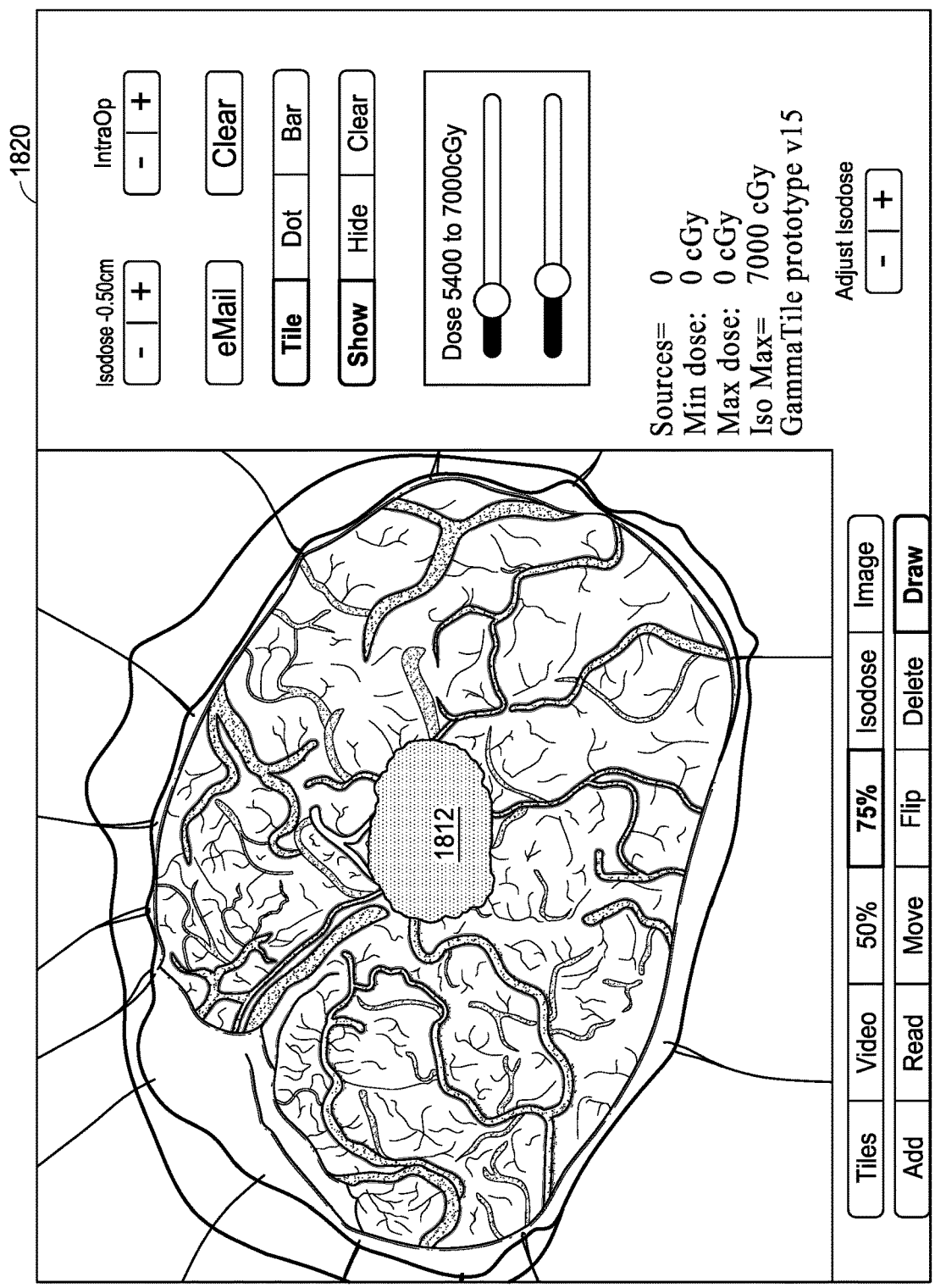
Figure 18C:
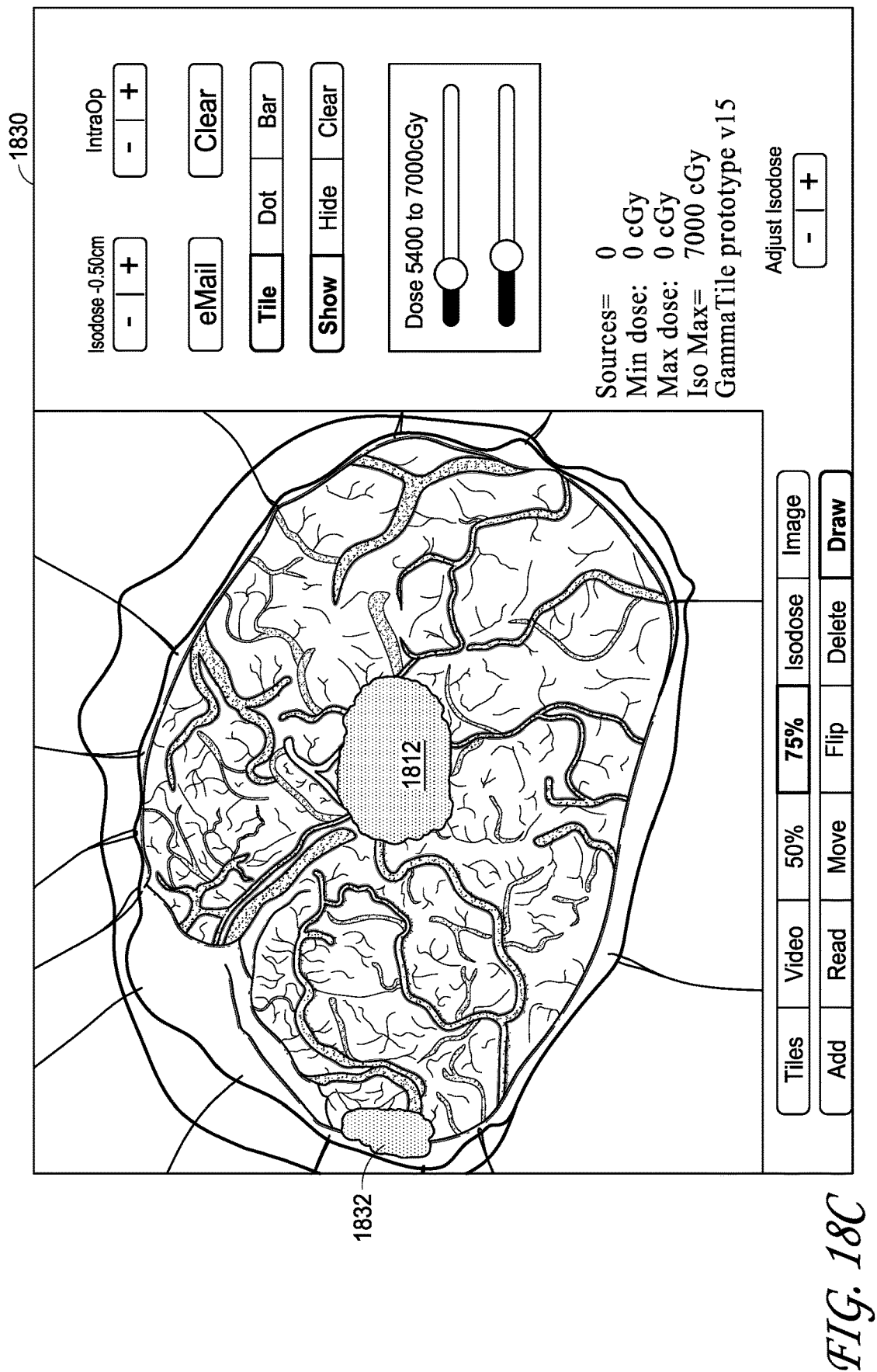
Figure 18D:
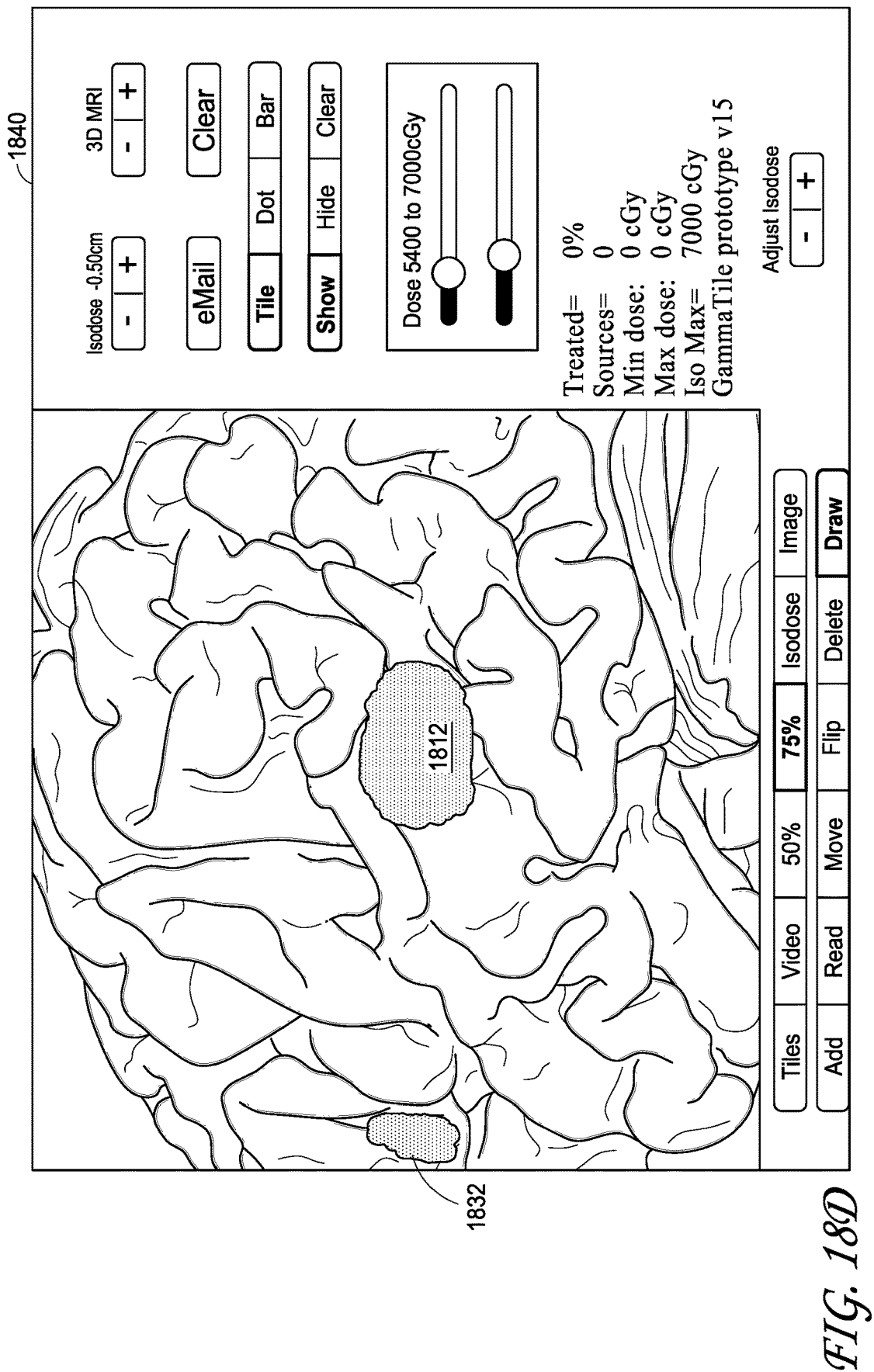

Moving to FIG. 17A, the same planning image and treatment region 1602 from FIG. 16 are shown, but now with an additional treatment region 1702 added in the GUI 1710 of FIG. 17A. Thus, as shown in this figure, the user may draw more than one treatment region. The "Show", "Hide", and "Clear" buttons shown on button bar 1240 may be used to control display of the drawn regions and initiate erasure of the drawn regions. For example, the "Show" button cases the drawn region(s) to be displayed (e.g., as in FIG. 17A), the "Hide" button causes them to be hidden (e.g., as in FIG. 17B), and the "Clear" button causes them to be erased (e.g., such that they will not be re-displayed when the "Show" button is subsequently selected).

FIG. 18 illustrates the placement planning user interface at four stages 1810, 1820, 1830, 1840 during a portion of a lesion simulation process. As discussed herein, multiple images of the patient's anatomy may be available that are in the same frame of reference. In the example of FIG. 18, two images are available, a 3D volume rendering from a preoperative MRI shown in the planning user interface at stage 1810 and an intraoperative photograph or live video image shown in the planning user interface at stage 1820. In this example, with the preoperative MRI image displayed at stage 1810, a first treatment region 1812 has been drawn by the user (which may be displayed in a particular color or texture depending on system and/or user preferences) on the preoperative MRI. In response to the user selecting the control 1220, such as by pressing the "+" button to move through available images in a first direction and the "−" button to move through the available images in a reverse direction, the 3D volume rendering image at stage 1810 is replaced with the intraoperative image at stage 1820, but with the treatment region 1812 remaining on the planning image at stage 1820. Thus, use of multiple planning images in this manner, especially if the images are registered accurately, may enhance the user's ability to place example treatment regions and test various treatment plans on those treatment regions, and may increase efficacy of the developed treatment plan.

In some embodiments, the draw function allows the user to draw regions on any of the images (e.g., either of the registered images shown at stages 1810 or 1820). For further example, moving to stage 1830, the user has drawn a second treatment region 1832 on the intraoperative region, which may represent a lesion observed at surgery that is especially visible on the intraoperative image. Next, at stage 1840, the user has switched back to the original 3D MRI image (e.g., using the control 1220) and both regions 1812 and 1832 remain drawn by the 3D volume rendering image.

Figure 19:
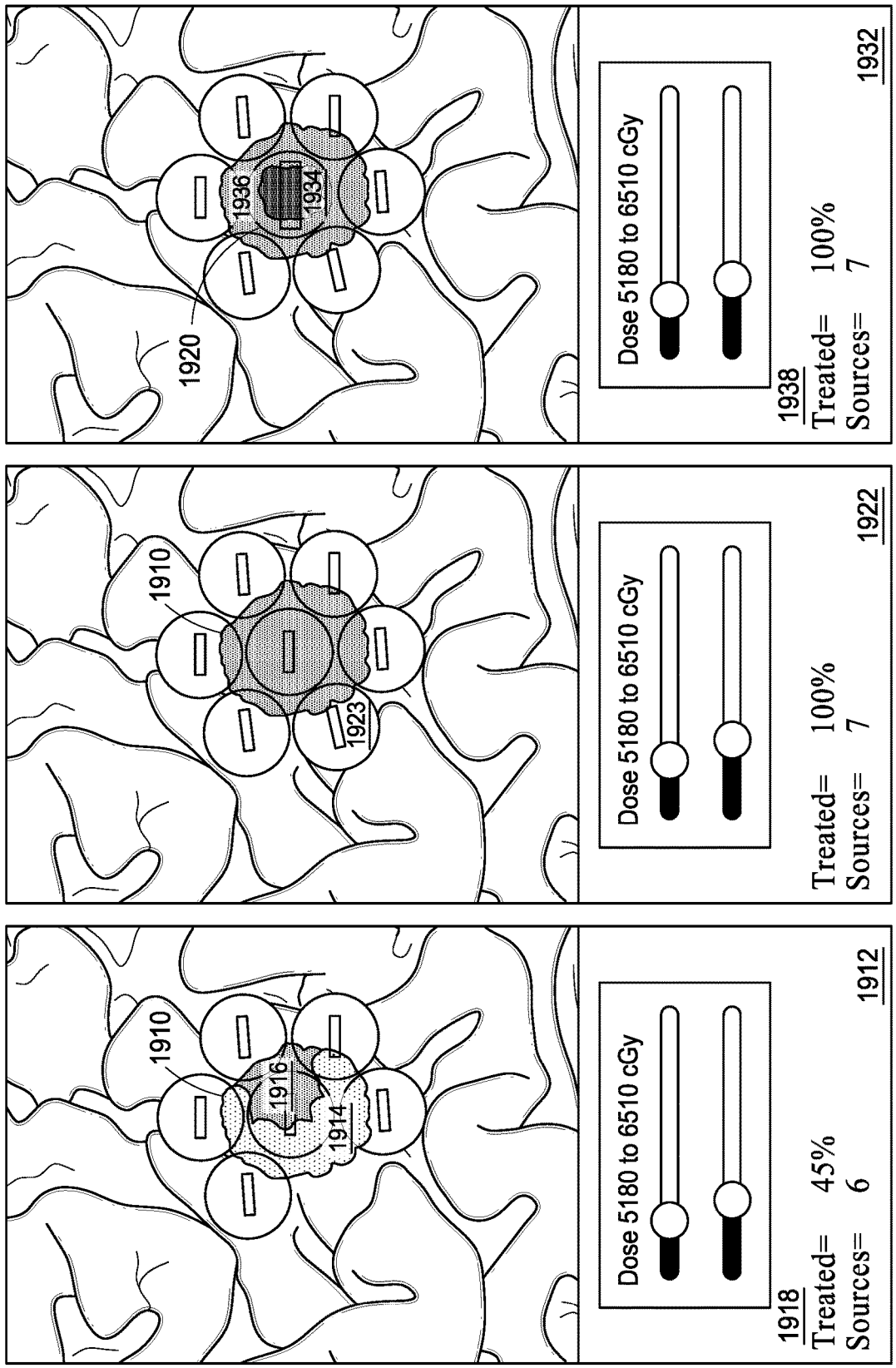
FIG. 19 illustrates a system where a desired range of radiation dose may be selected by the users and various portions of a drawn lesion or region to be treated may be automatically color-coded to illustrate regions that fall below, within, and above the desired dose range.

FIG. 19 illustrates a portion of the planning software user interface at three stages, 1912, 1922, and 1932. In this example, a treatment plan is adjusted through the stages and dosage on the treatment region 1902 are illustrated. As shown in this example, once a lesion or other treatment region is drawn by the user, it may be useful for the user to be shown which portions of the drawn region are adequately treated based on a current treatment plan, and corresponding dosage, that is indicated by the user, such as with reference to a prescribed dose range. In the example of FIG. 19, the treatment region 1910 includes a large number of small subregions and the radiation dose at any desired tissue level is automatically calculated for each subregion. In the example shown, the pattern (or color in other embodiments) of each subregion is automatically chosen based on a relationship between the radiation dose to that region and the prescribed dose range. In the example shown, subregions receiving a radiation dose below the prescribed range of 5180-6510 cGy at 5 mm below the brain surface are shown in a lighter pattern 1914 (e.g., yellow in a color embodiment), those within the prescribed range in a more dense pattern 1916 (e.g., green in a color embodiment), and those above the prescribed range in an even more dense pattern 1936 (e.g., red in a color embodiment).

In the example of FIG. 19, at stage 1912 the treatment region 1910 is shown with superimposed virtual implants (comprising radiation seeds in this embodiment). Based on the radiation dose delivered by the seeds, some subregions of the drawn region are displayed in green (subregion 1916), indicating that they fall within the prescribed dose range while other regions are displayed in yellow (subregion 1914), indicating that they fall below the prescribed dose range. In addition, the total fraction of the drawn region that falls within or above the dose range is automatically calculated and reported to the user, e.g. "Treated: 45%" as shown as treatment coverage information 1918.

Moving to stage 1922, an additional implant 1923 has been added to the plan and now the system is automatically showing the entire treatment region 1910 as green and reporting that 100% of the region is treated.

Next, at stage 1932, a centrally located implant 1920 has been flipped, placing the seed within it closer to the tissue, as indicated by the larger bar icon within the implant 1920. The radiation dose has been automatically recalculated and the subregions re-rendered to show central subregions 1934 in red, indicating that the dose falls above the prescribed range, and the outer subregions 1936 as green, indicating that the dose falls within the prescribed range. The associated % treated remains 100% at stage 1920, as shown in the treatment coverage information 1938, as all of the subregions fall within or above the prescribed range. In another embodiment, the % of the total region that is above the treatment range may be reported also, or alternatively.

Figure 20:
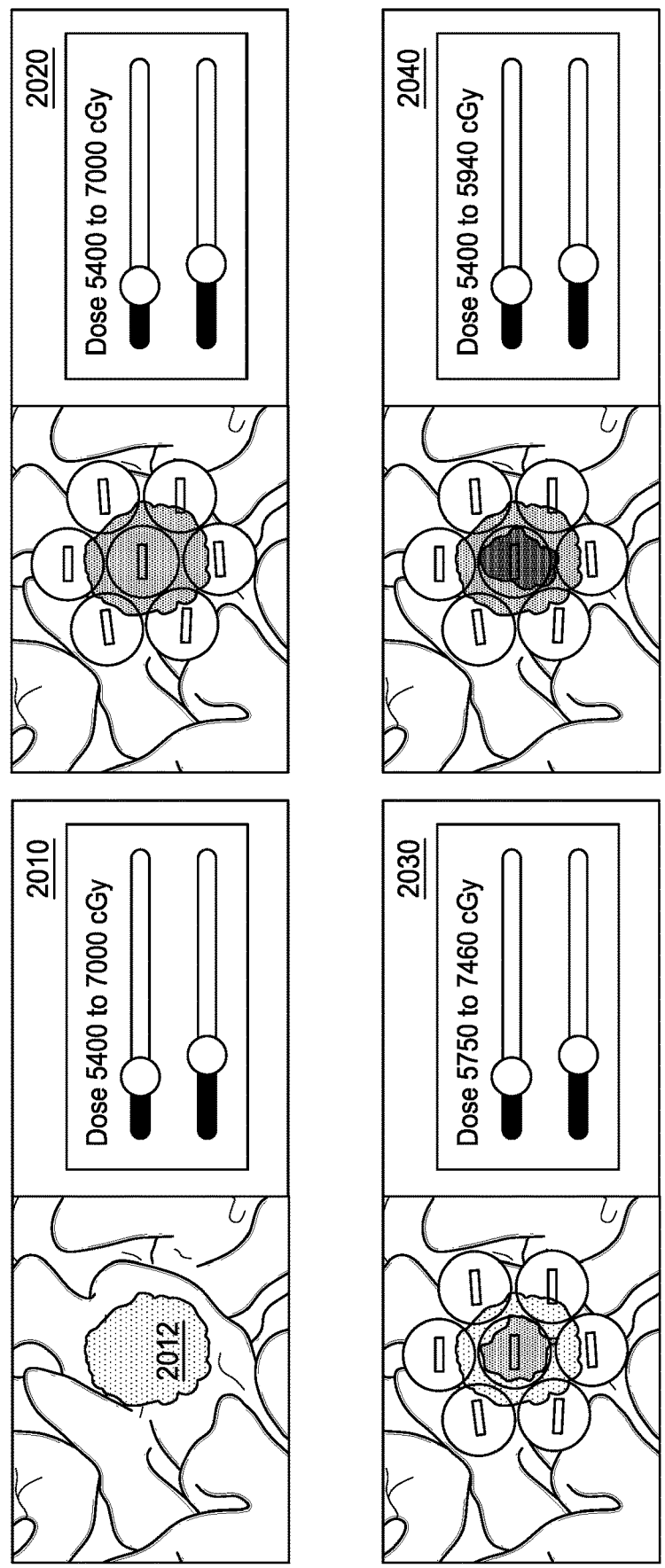
FIG. 20 illustrates interactive adjustment of the prescribed dose range with automatic analysis and color coding of the region to be treated to show which components fall below, within, and above the treatment range.

FIG. 20 illustrates a portion of a planner user interface at four stages 2010, 2020, 2030 and 2040. These example user interfaces illustrate an embodiment wherein the user may interactively change the upper and lower values of the prescribed treatment range, for example using graphical user interface components such as sliders. In the planner user interface illustrated, the lower and upper values of the treatment dose range are reported, e.g., "Dose 5400 to 7000 cGy" and there are associated sliders that the user may user to adjust these values, e.g., an upper slider may adjust the upper value and a lower slider may adjust the lower value, or the opposite. At stage 2010, a treatment region has been drawn by the user, but no implants (e.g., carriers with seeds) are present. In one embodiment, subregions (of the treatment region 2012) below the treatment range are displayed in yellow (illustrated as a sparse dotted pattern in this example), subregions within the treatment range in green (illustrated as a more dense dotted pattern in this example), and subregions above the treatment range in red (illustrated as an even more dense dotted pattern in this example). In other embodiments, different colors schemes, patterns, or visual indicators may be used. At stage 2010, because there are no implants present (and, thus, no seeds), the treatment region is displayed entirely in yellow to indicate all subregions fall below the treatment range.

Moving to stage 2020, the user has added seven virtual carriers (tiles in this example) over the treatment region, each with a seed. Based on the plane being evaluated and the treatment range indicated, the entire treatment region 2012 now falls within the treatment range and is therefore automatically displayed as green.

Next, at stage 2030, the lower value of the treatment range has been increased to 5750 (from the lower limit of 5400 illustrated at stage 2020) and now the peripheral portions of the treatment region are outside of the updated treatment rang and, thus, are displayed as yellow since the dose reaching those subregions falls below the value of 5750 cGy, the lower end of the prescribed dose range.

At stage 2040, the lower end of the dose range has been reset to 5400 cGy, but the upper end of the dose range has been lowered from 7000 cGy to 5940 cGy. With these changes in the dose range, the peripheral subregions are displayed in green, indicating that the dose they receive falls within the treatment range, but the middle portion of the region is now displayed as red, indicating it is receiving a dose above the prescribed range.

The appearance of subregions at stages 2030 and 2040 is explained by the fact that the central portion of the region is receiving a higher dose than the peripheral regions based on the arrangement of the seeds and overlapping radiation from the seeds, which is further discussed with reference to FIG. 21.

Figure 21:
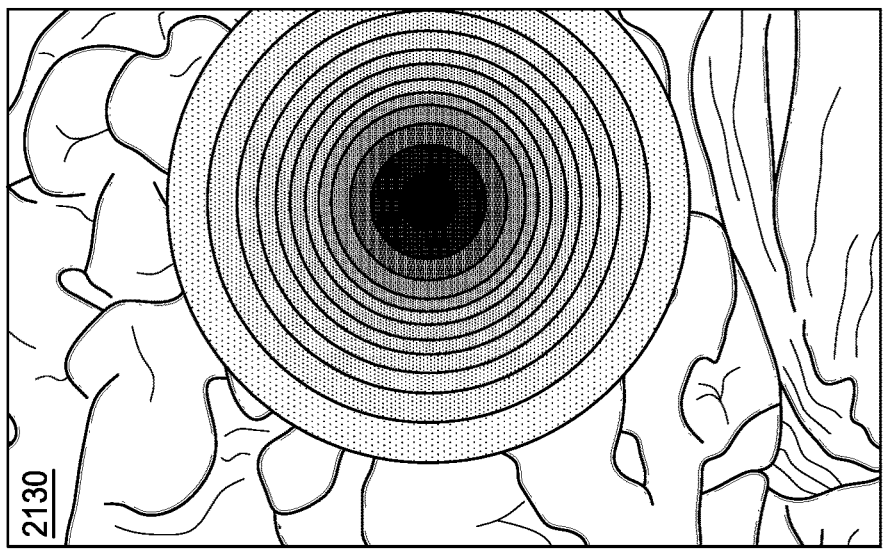
FIG. 21 illustrates display of the treatment region and various superimposition of an isodose plan.
Figure 21:
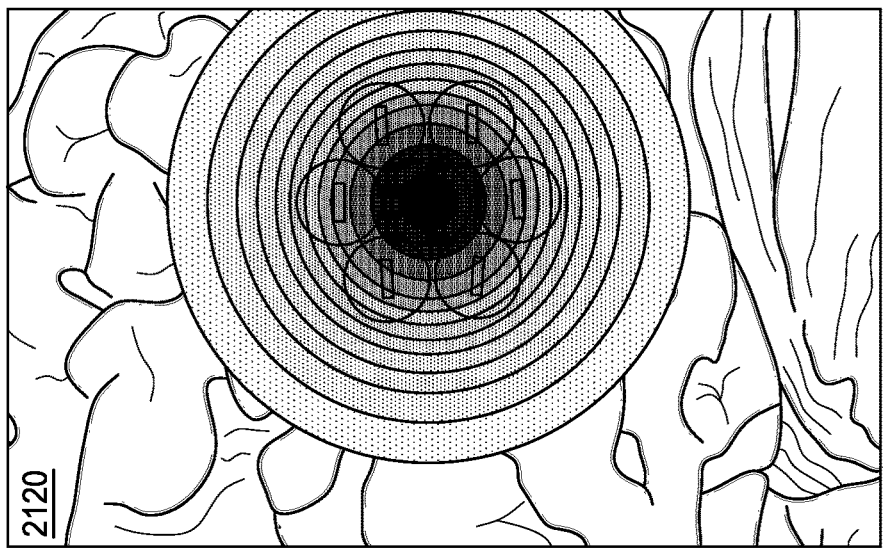
Figure 21:
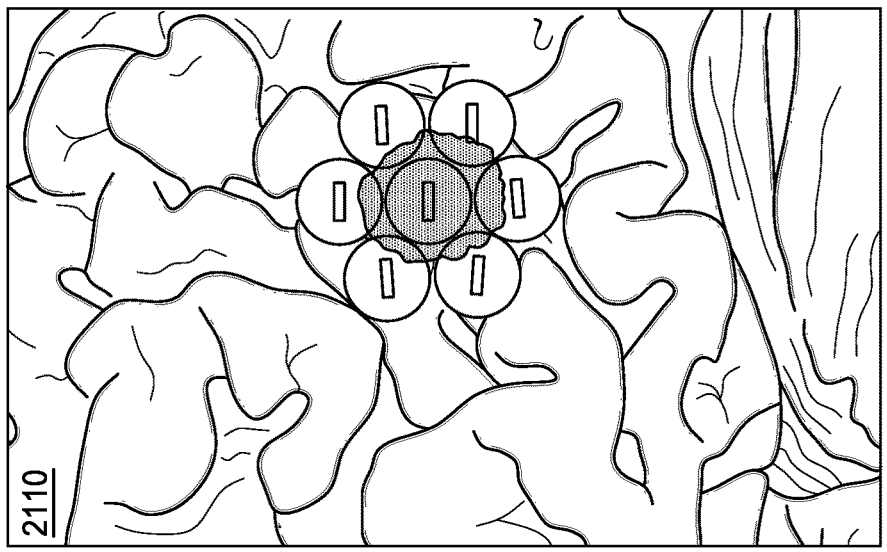

FIG. 21 illustrates different display modes for a given treatment region that has been drawn on a planning image and a particular treatment plan (including an arrangement of multiple implants). In user interface 2110, the treatment region and implants from stage 2020 of FIG. 20 are shown. In user interface 2120, the isodose plan associated with the treatment plan includes semitransparent fill patterns (and having varying display characteristics, such as colors, gradients, or fill patterns), and in user interface 2130 the isodose plan includes solid fill patterns, without (or overlapping) display of the treatment region and carriers. In these examples, higher radiation doses are show as more dense patterns between isodose curves. Thus, the highest dose for this configuration of carriers is in the central portion of the carrier arrangement where radiation from multiple seeds overlaps, and the dose decreases as distance from the center of the carrier arrangement increases. Of course, depending on the configuration of the carriers, as well as the characteristics of the carriers (e.g., seed placement and strength), the radiation dosage pattern may take on various forms such as non-uniform arrangements that are shown in other embodiments herein. In some embodiments, buttons or other controls that allow the user to switch between the display modes illustrated in FIG. 21, or other similar display modes, such as of different transparencies, may be provided in the planning software user interface (or via keyboard shortcuts, voice commands, etc.).

Figure 22:
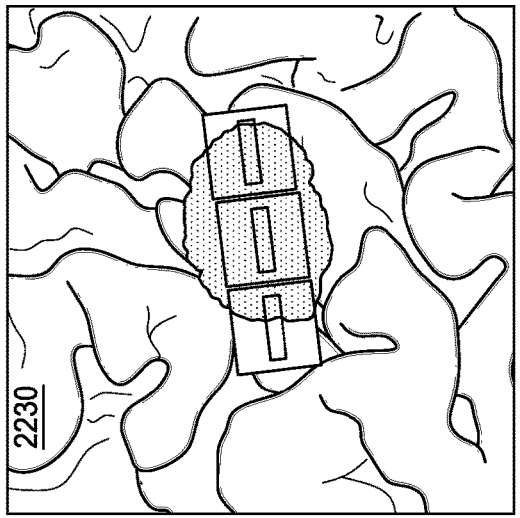
FIG. 22 illustrates a region to be treated with several different seed configurations and the resulting display of the treatment region.
Figure 22:
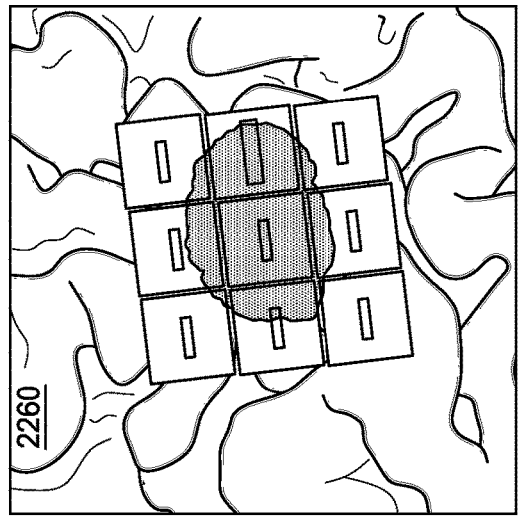
Figure 22:
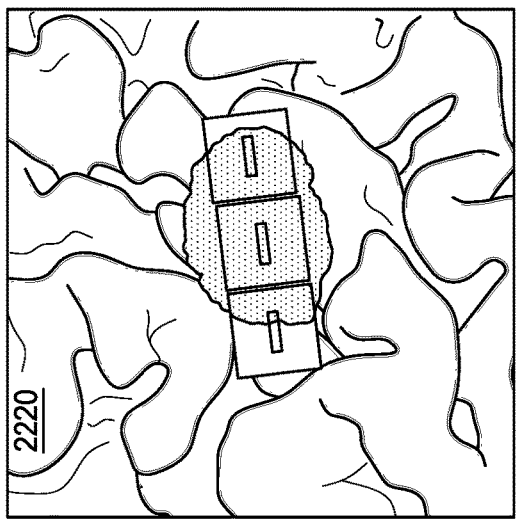
Figure 22:
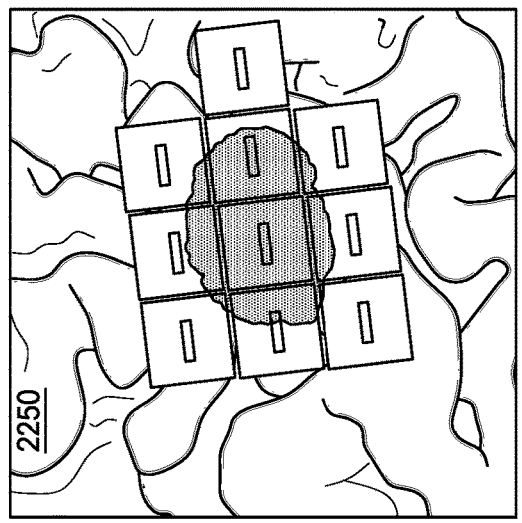
Figure 22:
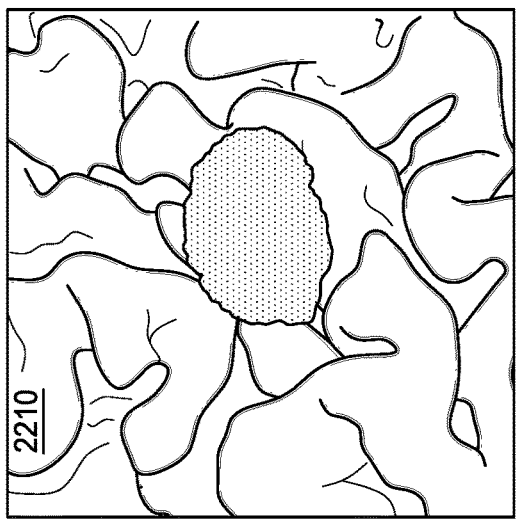
Figure 22:
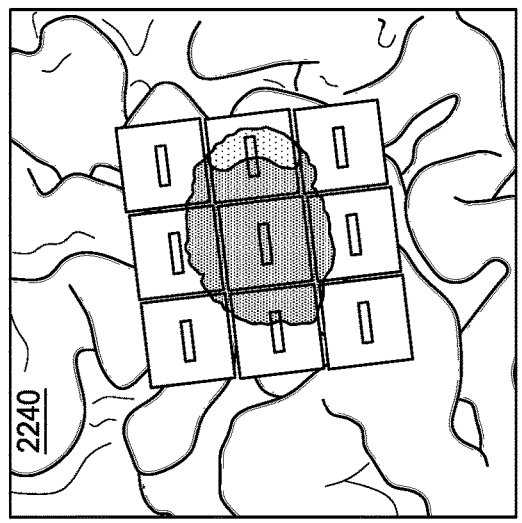

FIG. 22 illustrates a portion of software planning user interface as a treatment region is created, a treatment plan is generated, and indications of dosages to subregions of the treatment region are automatically displayed and updated as the carrier configuration changes.

At stage 2210, a treatment region is drawn by the user with no associated carriers. As in prior examples, the pattern in this treatment region (or some color, e.g., yellow, or other visual indicator) indicates that radiation reaching the various subregions of the treatment region falls below the prescription range. At stage 2220, the user has added three carriers, each with a seed, to the treatment plan. As shown by the lack of change in the pattern (or color in other embodiments) of the treatment region, the radiation dose from the three virtual implants is insufficient to reach the prescribed dose range.

Next, at stage 2230 the three virtual carriers have been flipped (indicate by the larger bar icons), which puts the seeds closer to the brain (or other treatment surface) and increases the dose to the underlying brain. Despite that, the radiation dose to the treatment region is still insufficient to reach the prescribed dose range and the region pattern remains unchanged.

At stage 2240, six additional carriers, each having a seed, are added so that there are now nine seeds, all in a non-flipped configuration. Most of the treatment region (all but the far right margin of the treatment region) has now changed to a more dense pattern (or green color in another embodiment), indicating that those subregions fall within the prescription range. A small portion of subregions on the right margin of the treatment region remain unchanged from the pattern at stages 2210-2230, indicating that those subregions still are below the prescription range.

At stage 2250, a tenth carrier, having a seed, has been added on the right and the previously undertreated right margin subregions are now updated to indicate they are within the prescribed dose range, causing the entire treatment region to have a common pattern (or color in another embodiment).

At stage 2260, which may be an alternative to stage 2250, rather than adding a tenth seed to the arrangement of seeds shown in 2240, a seed on the right overlying the undertreated right margin region has been flipped to increase the underlying dose so that the entire treatment region is now within the treatment range and shown with the pattern indicating all subregions are within the treatment range (e.g., green in a color embodiment).

Example System Architecture

As noted above, FIG. 1 illustrates an example computing device 150 that may perform some or all of the functions discussed herein with reference to the implant planning system and/or the implant placement guide system. In some implementations, these systems may each include one or more separate computing device with components similar to those in computing device 150. The computing device 150 may include, for example, a single computing device, a computer server, or a combination of one or more computing devices and/or computer servers. Depending on the embodiment, the components illustrated in the computing device 150 may be distributed amongst multiple devices, such as via a local area or other network connection. In other embodiments the computing device 150 may include fewer and/or additional components than are illustrated in FIG. 1.

In the embodiment of FIG. 1, the various devices are in communication via a network 190, which may include any combination of communication networks, such as one or more of the Internet, LANs, WANs, MANs, etc., for example.

The computing device 150 includes one or more central processing units ("CPU") 152, which may each include one or more conventional or proprietary microprocessor(s). The computing device 150 may further include one or more memories/storage 153, such as random access memory ("RAM"), for temporary storage of information, read only memory ("ROM") for permanent storage of information, and/or a mass storage device, such as a hard drive, diskette, or optical media storage device. The memory/storage 153 may store software code, or instructions, for execution by the processor 152 in order to cause the computing device to perform certain operations, such as described herein.

The methods described and claimed herein may be performed by any suitable computing device, such as the computing device 150. The methods may be executed on the computing devices in response to execution of software instructions or other executable code read from a tangible computer readable medium. A computer readable medium is a data storage device that can store data that is readable by a computer system. Examples of computer readable mediums include read-only memory, random-access memory, other volatile or non-volatile memory devices, CD-ROMs, magnetic tape, flash drives, and optical data storage devices.

The exemplary computing device 150 may include one or more input devices 156 and interfaces, such as a keyboard, trackball, mouse, drawing tablet, joystick, game controller, touchscreen (e.g., capacitive or resistive touchscreen), touchpad, accelerometer, and/or printer, for example. The computing device may also include one or more displays 155 (also referred to herein as a display screen), which may also be one of the I/O devices in the case of a touchscreen, for example. Display devices may include LCD, OLED, or other thin screen display surfaces, a monitor, television, projector, or any other device that visually depicts user interfaces and data to viewers. The computing device 150 may also include one or more multimedia devices, such as camera 158, speakers, video cards, graphics accelerators, and microphones, for example.

In the embodiment of FIG. 1, interfaces 157 provide a communication interface to various external devices via the network 190.

In the embodiment of FIG. 1, the computing device 150 also includes one or more modules 151. In general, the word "module," as used herein, refers to logic embodied in hardware or firmware, or to a collection of software instructions, possibly having entry and exit points, written in any programming language, such as, for example, Java, Python, Perl, Lua, C, C++, C #, etc. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software modules configured for execution on computing devices may be provided on a computer readable medium, such as a compact disc, digital video disc, flash drive, or any other tangible medium. Such software code may be stored, partially or fully, on a memory device of the executing computing device, such as the computing device 150, for execution by the computing device. It will be further appreciated that hardware modules may be comprised of connected logic units, such as gates and flip-flops, and/or may be comprised of programmable units, such as programmable gate arrays or processors. The modules described herein are typically implemented as software modules, but may be represented in hardware or firmware. Generally, the modules described herein refer to logical modules that may be combined with other modules or divided into sub-modules despite their physical organization or storage. Modules may include an implant planning system module that performs the functions discussed herein with reference to the implant planning system and an implant placement guide module that performs the functions discussed herein with reference to the implant placement guide system, whether on a single computing device 150 or multiple computing devices 150.

ADDITIONAL EMBODIMENTS

The various features and processes described above may be used independently of one another, or may be combined in various ways. All possible combinations and sub-combinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the systems and methods can be practiced in many ways. As is also stated above, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

What is claimed is:

1. A treatment system comprising:
   one or more physical implants each comprising one or more radioactive seeds embedded in a biocompatible material, wherein the one or more physical implants are configured to be placed on an exposed treatment surface of a surgically-created cavity in mammalian tissue and configured to hold the radioactive seeds in precise locations relative to the exposed treatment surface of the mammalian tissue;
   one or more sensors configured to provide sensor data usable to determine positions of the one or more physical implants placed during a surgical procedure;
   an optical camera configured to obtain images of the exposed treatment surface of a patient during the surgical procedure; and
   a hardware computer processor in communication with a non-transitory computer readable medium having software instructions stored thereon, the software instructions executable by the hardware computer processor to cause a computing system to perform operations comprising:
   calculate a radiation isodose plan indicative of an expected radiation dosage expected to result from placement of the one or more physical implants on the exposed treatment surface;
   based on the sensor data from the one or more sensors, determine, during the surgical procedure, positions of each of the one or more physical implants;
   during the surgical procedure, generate a user interface viewable by a user, the user interface depicting:
   at least a portion of the exposed treatment surface of the patient, based on at least the images obtained from the optical camera during the surgical procedure;
   one or more virtual implants superimposed on the depiction of the at least the portion of the exposed treatment surface;
   representations of at least one of the one or more physical implants; and
   the radiation isodose plan superimposed on the depiction of the at least the portion of the exposed treatment surface and the representations of the at least one of the one or more physical implants;
   in response to determining, based on the sensor data, that a position of a first physical implant of the one or more physical implants corresponds with a position of a first virtual implant of the one or more virtual implants superimposed on the depiction of the at least the portion of the exposed treatment surface, automatically update the depiction of the first virtual implant to indicate proper placement of the first physical implant; and
   cause a display device to display the user interface.

2. The treatment system of claim 1, further comprising:
   based on a user-provided dosage, automatically calculating a treatment plan including a combination of physical implants configured to deliver the dosage to a treatment area in the mammalian tissue of the patient.

3. The computing system of claim 2, wherein the automatic calculation is further based on a user-provided indicator of a tissue sparing parameter or a dose uniformity parameter.

4. The treatment system of claim 3, further comprising: automatically calculating a second treatment plan including a second combination of physical implants configured to deliver the dosage to the treatment area of the patient, based on a different tissue sparing parameter or different dose uniformity parameter.

5. The treatment system of claim 2, wherein the automatic calculation is further based on one or more user-provided exclusion areas of the treatment area of the patient.

6. The treatment system of claim 2, wherein the treatment plan further includes sizes, orientations, and/or positions of the physical implants.

7. The treatment system of claim 1, wherein the radiation isodose plan has a transparency of less than one hundred percent.

8. The treatment system of claim 1, wherein said automatically updating the depiction of the first virtual implant comprises removing the virtual implant from the user interface.

9. The treatment system of claim 1, wherein said automatically updating the depiction of the first virtual implant comprises altering an appearance of the first virtual implant in the user interface.

10. The treatment system of claim 1, wherein a first physical implant of the at least one of the one or more physical implants comprises a plurality of radioactive seeds, and wherein calculating the radiation isodose plan is based, at least in part, on characteristics of a first virtual implant associated with the first physical implant including a radiation emitted from the first physical implant by the plurality of seeds.

11. The treatment system of claim 1, wherein calculating the radiation isodose plan is based, at least in part, on characteristics of the one or more virtual implants, wherein the characteristics include positions of seeds embedded in the one or more physical implants corresponding to the one or more virtual implants or a direction that radiation is emitted from the one or more physical implants corresponding to the one or more virtual implants.

12. The treatment system of claim 1, wherein the software instructions are further executable by the hardware computer processor to cause the computing system to:
calculate an order in which to place the one or more physical implants in one or more determined positions on the exposed treatment surface of the patient during the surgical procedure.

13. A treatment system comprising:
one or more physical implants each comprising one or more radioactive seeds embedded in a biocompatible material, wherein the one or more physical implants are configured to be placed on an exposed treatment surface of a surgically-created cavity in mammalian tissue and configured to hold the radioactive seeds in precise locations relative to the exposed treatment surface of the mammalian tissue;
one or more sensors configured to: provide sensor data usable to determine positions of the one or more physical implants placed during a surgical procedure;
an optical camera configured to obtain images of the exposed treatment surface of a patient during the surgical procedure; and
a hardware computer processor in communication with a non-transitory computer readable medium having software instructions stored thereon, the software instructions executable by the hardware computer processor to cause a computing system to perform operations comprising:
calculate a radiation isodose plan indicative of an expected radiation dosage expected to result from placement of the one or more physical implants on the exposed treatment surface;
based on the sensor data, determine, during the surgical procedure, positions of each of the one or more physical implants;
during the surgical procedure, generate a user interface viewable by a user, the user interface depicting:
at least a portion of the exposed treatment surface of the patient, based on at least the images obtained from the optical camera during the surgical procedure;
one or more virtual implants superimposed on the depiction of the at least the portion of the exposed treatment surface;
representations of at least one of the one or more physical implants; and
the radiation isodose plan superimposed on the depiction of the at least the portion of the exposed treatment surface and the representations of the at least one of the one or more physical implants; and
cause a display device to display the user interface.

14. The treatment system of claim 13, wherein the software instructions are further configured to perform a pattern recognition routine on the images from the at least one optical camera, wherein the pattern recognition routine is configured to identify physical implants.

15. The treatment system of claim 13, wherein the software instructions are further configured to detect placement of the physical implants on the exposed treatment surface of the patient.

16. The treatment system of claim 13, wherein the one or more sensors includes a stereotactic surgical localizing system configured to output the sensor data usable to determined positions of the one or more physical implants.

17. The treatment system of claim 13, wherein the sensor data is further usable to determine positions of one or more surgical instruments.

18. The treatment system of claim 17, wherein the user interface further depicts representations of the one or more surgical instruments at their determined positions.

19. The treatment system of claim 13, further comprising:
based on a user-provided dosage, automatically calculating a treatment plan including a combination of physical implants configured to deliver the dosage to a treatment area in the mammalian tissue of the patient.

20. The treatment system of claim 19, wherein the automatic calculation is further based on one or more user-provided exclusion areas of the treatment area of the patient.

21. The treatment system of claim 19, wherein the treatment plan further includes sizes, orientations, and/or positions of the physical implants.

22. The treatment system of claim 19, wherein the automatic calculation is further based on a user-provided indicator of a tissue sparing parameter or a dose uniformity parameter.

23. The treatment system of claim 22, further comprising:
automatically calculating a second treatment plan including a second combination of physical implants configured to deliver the dosage to the treatment area of the patient, based on a different tissue sparing parameter or different dose uniformity parameter.

24. The treatment system of claim 13, wherein the radiation isodose plan has a transparency of less than one hundred percent.

25. A treatment method comprising:
by one or more hardware computer processors in communication with a non-transitory computer readable medium having software instructions stored thereon, executing the software instructions to cause a computing system to perform operations comprising:
accessing sensor data usable to determine positions of the one or more physical implants placed on an exposed treatment surface of a surgically-created cavity of a patient during a surgical procedure, wherein the one or more physical implants each comprise one or more radioactive seeds embedded in a biocompatible material;
receiving, from an optical camera, images of the exposed treatment surface of the patient during the surgical procedure;
calculating a radiation isodose plan indicative of an expected radiation dosage expected to result from placement of the one or more physical implants on the exposed treatment surface;
based on the sensor data, determining, during the surgical procedure, positions of each of the one or more physical implants;
during the surgical procedure, generating a user interface viewable by a user, the user interface depicting:
at least a portion of the exposed treatment surface of the patient, based on at least the images received from the optical camera during the surgical procedure;
one or more virtual implants superimposed on the depiction of the at least the portion of the exposed treatment surface;
representations of at least one of the one or more physical implants; and
the radiation isodose plan superimposed on the depiction of the at least the portion of the exposed treatment surface and the representations of the at least one of the one or more physical implants;
in response to determining, based on the sensor data, that a position of one of the one or more physical implants corresponds with a position of a first virtual implant of the one or more virtual implants superimposed on the depiction of the at least the portion of the exposed treatment surface, automatically update the depiction of the first virtual implant; and
causing a display device to display the user interface.

26. A treatment method comprising:
by one or more hardware computer processors in communication with a non-transitory computer readable medium having software instructions stored thereon, executing the software instructions to cause a computing system to perform operations comprising:
accessing sensor data usable to determine positions of the one or more physical implants placed on an exposed treatment surface of a surgically-created cavity of a patient during a surgical procedure, wherein the one or more physical implants each comprise one or more radioactive seeds embedded in a biocompatible material;
receiving, from an optical camera, images of the exposed treatment surface of the patient during the surgical procedure;
calculating a radiation isodose plan indicative of an expected radiation dosage expected to result from placement of the one or more physical implants on the exposed treatment surface;
based on the sensor data, determining, during the surgical procedure, positions of each of the one or more physical implants;
during the surgical procedure, generating a user interface viewable by a user, the user interface depicting:
at least a portion of the exposed treatment surface of the patient, based on at least the images received from the optical camera during the surgical procedure;
one or more virtual implants superimposed on the depiction of the at least the portion of the exposed treatment surface;
representations of at least one of the one or more physical implants; and
the radiation isodose plan superimposed on the depiction of the at least the portion of the exposed treatment surface and the representations of the at least one of the one or more physical implants; and
causing a display device to display the user interface.

* * * * *